(12) United States Patent
Comanducci et al.

(10) Patent No.: US 8,980,286 B2
(45) Date of Patent: Mar. 17, 2015

(54) MULTIPLE VARIANTS OF MENINGOCOCCAL PROTEIN NBM1870

(75) Inventors: Maurizio Comanducci, Berardenga (IT); Mariagrazia Pizza, Siena (IT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/364,264

(22) Filed: Feb. 1, 2012

(65) Prior Publication Data

US 2012/0148617 A1 Jun. 14, 2012

Related U.S. Application Data

(63) Continuation of application No. 10/536,215, filed as application No. PCT/IB03/06320 on Nov. 21, 2003.

(30) Foreign Application Priority Data

Nov. 22, 2002 (GB) .................................. 0227346.4

(51) Int. Cl.
*A61K 39/095* (2006.01)
*C07K 14/22* (2006.01)

(52) U.S. Cl.
CPC .............. *A61K 39/095* (2013.01); *C07K 14/22* (2013.01)
USPC .................. 424/250.1; 424/190.1; 424/192.1; 424/193.1; 424/256.1

(58) Field of Classification Search
CPC combination set(s) only.
See application file for complete search history.

(56) References Cited

U.S. PATENT DOCUMENTS

| | | | |
|---|---|---|---|
| 6,903,202 B2 | 6/2005 | Guerriero et al. | |
| 7,348,006 B2 | 3/2008 | Contorni et al. | |
| 7,576,176 B1 | 8/2009 | Fraser et al. | |
| 7,785,608 B2 * | 8/2010 | Zlotnick et al. | 424/249.1 |
| 7,862,827 B2 | 1/2011 | Giuliani et al. | |
| 8,101,194 B2 | 1/2012 | Zlotnick et al. | |
| 8,226,960 B2 | 7/2012 | Masignani et al. | |
| 8,273,360 B2 | 9/2012 | Pizza et al. | |
| 8,293,251 B2 | 10/2012 | Scarlato et al. | |
| 8,394,390 B2 | 3/2013 | Galeotti et al. | |
| 8,398,988 B2 | 3/2013 | Contorni et al. | |
| 8,398,999 B2 | 3/2013 | Masignani et al. | |
| 8,524,251 B2 | 9/2013 | Fraser et al. | |
| 8,563,007 B1 | 10/2013 | Zlotnick et al. | |
| 8,574,597 B2 | 11/2013 | Zlotnick | |
| 8,734,812 B1 | 5/2014 | Galeotti et al. | |
| 8,840,907 B2 | 9/2014 | Pizza | |
| 2003/0035806 A1 * | 2/2003 | D'Ambra et al. | 424/184.1 |
| 2003/0068336 A1 | 4/2003 | Ryall | |
| 2004/0092711 A1 | 5/2004 | Arico | |
| 2004/0110670 A1 | 6/2004 | Arico et al. | |
| 2004/0167068 A1 | 8/2004 | Zlotnick et al. | |
| 2005/0222385 A1 | 10/2005 | Pizza | |
| 2006/0008476 A1 * | 1/2006 | Pizza et al. | 424/250.1 |
| 2006/0051840 A1 | 3/2006 | Arico et al. | |
| 2006/0171957 A1 | 8/2006 | Pizza | |
| 2006/0240045 A1 | 10/2006 | Berthet et al. | |
| 2006/0251670 A1 | 11/2006 | Comanducci et al. | |
| 2007/0026021 A1 | 2/2007 | Fraser et al. | |
| 2007/0082014 A1 | 4/2007 | Costantino | |
| 2007/0253984 A1 | 11/2007 | Khandke et al. | |
| 2008/0241180 A1 | 10/2008 | Contorni | |
| 2009/0285845 A1 | 11/2009 | Masignani et al. | |
| 2010/0267931 A1 | 10/2010 | Arico et al. | |
| 2012/0107339 A1 | 5/2012 | Granoff et al. | |
| 2014/0037668 A1 | 2/2014 | Giuliani et al. | |

FOREIGN PATENT DOCUMENTS

| | | |
|---|---|---|
| EP | 0467714 | 1/1992 |
| EP | 1645631 A2 | 4/2006 |
| EP | 1790660 | 5/2007 |
| EP | 2351767 A2 | 8/2011 |
| WO | WO-96/29412 A1 | 9/1996 |
| WO | WO-98/17805 | 4/1998 |
| WO | WO-99/57280 A | 11/1999 |
| WO | WO-00/22430 A2 | 4/2000 |
| WO | WO-00/66791 | 11/2000 |
| WO | WO-01/31019 | 5/2001 |
| WO | WO-01/52885 | 7/2001 |
| WO | WO-01/64920 A | 9/2001 |
| WO | WO-01/64922 A2 | 9/2001 |
| WO | WO-02/058737 A2 | 8/2002 |
| WO | WO-02/080965 A2 | 10/2002 |
| WO | WO-03/007985 A2 | 1/2003 |
| WO | WO-03/009869 A1 | 2/2003 |
| WO | WO-03/010194 A | 2/2003 |
| WO | WO-03/020756 A | 3/2003 |

(Continued)

OTHER PUBLICATIONS

Greenspan et al (Nature Biotechnology 7: 936-937, 1999).*
Chothia et al (The EMBO Journal, 1986, 5/4:823-26).*
Mikayama et al. (Nov. 1993. Proc.Natl.Acad.Sci. USA, vol. 90 : 10056-10060).*
Rudinger et al. (Jun. 1976. Peptide Hormones. Biol.Council. pages 5-7).* 1997-11-17-NM_shotgun.dbs and 1997-12-15-NM.dbs, located at <ftp://ftp.sanger.ac.uk/pub/pathogens/nm/old data/>.

(Continued)

*Primary Examiner* — Jennifer Graser
(74) *Attorney, Agent, or Firm* — Morrison & Foerster LLP

(57) ABSTRACT

Meningococcal protein NMB 1870 has been described in the prior art. The inventors have found that NMB 1870 is an effective antigen for eliciting anti-meningococcal antibody responses, and that it is expressed across all meningococcal serogroups. Forty-two different NMB 1870 sequences have been identified, and these group into three variants. Serum raised against a given variant is bactericidal within the same variant group, but is not active against strains which express one of the other two variants i.e. there is intra-variant cross-protection, but not inter-variant cross-protection. For maximum cross-strain efficacy, therefore, the invention uses mixture comprising different variants of NMB 1870.

41 Claims, 10 Drawing Sheets

(56) References Cited

FOREIGN PATENT DOCUMENTS

| WO | WO-03/063766 | | 8/2003 |
|---|---|---|---|
| WO | WO-03/080678 | A1 | 10/2003 |
| WO | WO-03/094834 | A2 | 11/2003 |
| WO | WO-2004/032958 | A1 | 4/2004 |
| WO | WO-2004/048404 | | 6/2004 |
| WO | WO-2004/065603 | A2 | 8/2004 |
| WO | WO-2004/067030 | A2 | 8/2004 |
| WO | WO-2004/094596 | A2 | 11/2004 |
| WO | WO-2004/103400 | A2 | 12/2004 |
| WO | WO-2006/024954 | A2 | 3/2006 |
| WO | WO-2006/081259 | | 8/2006 |
| WO | WO-2007/060548 | A2 | 5/2007 |
| WO | WO-2007/127665 | A2 | 11/2007 |
| WO | WO-2008/125985 | A2 | 10/2008 |
| WO | WO-2008/149238 | A2 | 12/2008 |
| WO | WO-2009/104097 | A2 | 8/2009 |
| WO | WO-2010/028859 | A1 | 3/2010 |
| WO | WO-2010/046715 | A1 | 4/2010 |

OTHER PUBLICATIONS

Aasel et al. (1998). Abstract from the 11$^{th}$ International Pathogenic *Neisseria* Conference, Nice France, Nov. 1-6, 1998. pp. 37-38.
Beernink et al (Jul. 2006). "Rapid Genetic Grouping of Factor H-Binding Protein (Genome-Derived Neisserial Antigen 1870), a Promising Group B Meningococcal Vaccine Candidate," Clinical and Vaccine Immunology 13(7):758-763.
Beernink et al. (Jun. 2008). "Bactericidal antibody responses, induced by meningococcal recombinant chimeric factor H-binding protein vaccines," Infection and Immunity 76(6):2568-2575.
Beernink et al. (Sep. 2008). "Fine antigenic specificity and cooperative bactericidal activity of monoclonal antibodies directed at the meningococcal vaccine candidate factor h-binding protein," Infection and Immunity 76(9):4232-4240.
Bernfield L. et al. (Sep. 2002). "Identification of a novel vaccine candidate for group B *Neisseria meningitidis*," Thirteenth International Pathogenic *Neisseria* Conference, Norwegian Institute of Public Health, Oslo, Norway, pp. 116 and 124.
Boslego et al. (1991). "Gonorrhea Vaccines," Chapter 17 In *Vaccines and Immunotherapy*, Cryz S.J. (Ed.), Pergamon Press: New York, NY, pp. 211-223.
Bowie, J. (1990). "Deciphering the Message in Protein Sequences: Tolerance to Amino Acid Substitutions," *Science* 247:1306-1310.
Campbell et al. (2002) "Safety, reactogenicity, and immunogenicity of a tetravalent meningococcal polysaccharide-diphtheria toxoid conjugate vaccine given to healthy adults," J. Infectious Diseases 186:1848-1851.
Cannon (1989). "Conserved Lipoproteins of Pathogenic *Neisseria* Species Bearing the H.8 Epitope: Lipid-Modified Azurin and H.8 Outer Membrane Protein," Clinical Microbiology Reviews 2(Suppl.):S1-S4.
Cantini et al. (Mar. 2006). "Solution Structure of the Immunodominant Domain of Protective Antigen GNA 1870 of *Neisseria meningitidis*," *Journal of Biological Chemistry* 281(11):7220-7227.
Centers for Disease Control and Prevention (2012). "Child & Adolescent Past Immunization Schedules—Consolidated Historical Records," Exerpts from website, 7 pages.
Centers for Disease Control and Prevention (Jan. 18, 2002) "Notice to readers: Recommended childhood immunization schedule—United States, 2002," MMWR Weekly 51(02):31-3.
Centers for Disease Control and Prevention (Jan. 21, 2000) "Notice to readers: Recommended childhood immunization schedule—United States, 2000," MMWR Weekly 49(02):35-8,47.
Chippaux et al. (Sep. 3, 2004). "Immunogenicity, safety, and memory of different schedules of *Neisseria meningitidis* A/C-diphtheria toxoid conjugate vaccine in infants in Niger," Vaccine 22(25-26):3303-11.
Cruse et al. (2003). Illustrated Dictionary of Immunology, 2$^{nd}$ Ed. CRC Press, pp. 46, 166, and 382.

Database accession No. NMB1994 (cf. XP2231040) (Tettelin et al.), uploaded Oct. 1, 2000.
Deacon et al. (1982) "A comparative clinical study of Adsorbed Tetanus Vaccine and Adult-type Tetanus-Diphtheria Vaccine," J Hyg Camb 89: 513-519.
Declaration by Dr. Julian Parkhill dated Jun. 12, 2008, submitted in opposition proceedings for EP1645631, 2 pages.
EMEA (May 4, 2010) "CHMP Assessment Report for Menveo™," 58 pages.
Farley J. et al. (Sep. 2002). "Characterization, cloning and expression of different subfamilies of the ORF 2086 gene from *Neisseria meningitidis*," Thirteenth International Pathogenic *Neisseria* Conference, Norwegian Institute of Public Health, Oslo, Norway, p. 124.
Feavers et al. (2009). "Meningococcal protein antigens and vaccines," Vaccine 275:B42-B50.
Fleischmann et al. (1995). "Whole-Genome Random Sequencing and Assembly of *Haemophilus influenzae* Rd," Science 269:496-501.
Fletcher et al. (2004). "Vaccine Potential of the *Neisseria meningitidis* 2086 Lipoprotein," Infection and Immunity 72(4): 2088-2100.
Fontana et al. (2002). A genomic approach Abstract from the 13$^{th}$ International Pathogenic *Neisseria* Conference, Oslo, Norway, Sep. 1-6, 2002. Page 248.
Giuliani et al. (2006). "A universal vaccine for serogroup B meningococcus," PNAS 103(29):10834-10839.
Giuliani et al. (Feb. 2005). "The Region Comprising Amino Acids 100 to 255 of *Neisseria meningitidis* Lipoprotein GNA 1870 Elicits Bactericidal Antibodies," Infection and Immunity 73(2): 1151-1160.
Greenspan et al. (1999). "Defining Epitopes: It's Not as Easy as It Seems," Nature Biotechnology 17:936-937.
Hou et al. (2005) "Protective antibody responses elicited by a meningococcal outer membrane vesicle vaccine with overexpressed genome-derived neisserial antigen 1870," J Infect Dis 192(4):580-90.
Jacobsson et al. (2009). "Prevalence and sequence variations of the genes encoding the five antigens included in the novel 5CVMB vaccine covering group B meningococcal disease" Vaccine. 27:1579-1584.
JCVI-CMR website showing Z2491 Sanger sequence (http://cmr.jcvi.org/tigr-scripts/CMR/shared/Genomes.cgi and links). (2010).
Jiang et al., (2010) "Broad vaccine coverage predicted for a bivalent recombinant factor H binding protein based vaccine to prevent serogroup B meningococcal disease" Vaccine 28:6086-6093.
Koeberling et al. (2007). "Improved immunogenicity of a H44/76 group B outer membrane vesicle vaccine with over-expressed genome-derived Neisserial antigen 1870," Vaccine 25(10):1912-1920.
Lucidarme et al., (Sep. 16, 2009) "Characterization of fHbp, nhba (gna2132), nadA, porA, sequence type (ST), and genomic presence of IS1301 in group B meningococcal ST269 clonal complex isolates from England and Wales" Journal of Clinical Microbiology, 47(11):3577-85.
Lucidarme et al., 2010 "Characterization of fHbp, nhba (gna2132), nadA, porA, and sequence type in group B meningococcal case isolates collected in England and Wales during Jan. 2008 and potential coverage of an investigational group B meningococcal vaccine" Clinical and Vaccine Immunology 17(6):919-929.
Masignani V. (Mar. 17, 2003). "Vaccination against *Neisseria meningitidis* using three variants of the lipoprotein GNA1870," J. Exp. Med. 197(6):789-799.
McVernon et al. (2003) "Effect of infant immunisation with meningococcus serogroup C-CRM(197) conjugate vaccine on diphtheria immunity and reactogenicity in pre-school aged children," Vaccine 21(19-20):2573-2579.
Morley, S. et al. (Dec. 12, 2001). "Vaccine prevention of meningococcal disease, coming soon?" *Vaccine* 20(5-6):666-687.
Murphy et al., (2009) "Sequence diversity of the factor H binding protein vaccine candidate in epidemiologically relevant strains of serogroup B *Neisseria meningitidis*" J Infect Dis 200:379-389.
Nassif (2000). "A Furtive Pathogen Revealed," Science 287: 1767-1768.
Notice of Opposition against European Patent EP 1645631, granted on Oct. 24, 2007. Opposition filed on Jul. 23, 2008. 20 pages.

(56) References Cited

OTHER PUBLICATIONS

Novartis (Oct. 9, 2008) "New Phase II data show Novartis investigational Meningitis B vaccine may also protect infants six months and older," Media Release, 4 pages.
Pajon et al., "Frequency of factor H-binding protein modular groups and susceptibility to cross-reactive bactericidal activity in invasive meningococcal isolates" Vaccine 28 (2010):2122-2129.
Parkhill, J. et al. (Mar. 2000). "Complete DNA Sequence of a Serogroup A Strain of *Neisseria meningitides* Z2491," *Nature* 404:502-505.
Parkhill, "Campylobacter jejuni genome sequence as the Sanger Centre," Post on BIOSCI/Bionet of May 8, 1998.
Patentees' Response to Opposition against European Patent EP 1645631, granted on Oct. 24, 2007. 13 pages.
Notice of Opposition against European Patent EP 1740217, granted on Jun. 15, 2011. Opposition filed by Sanofi Pasteur, Inc. on Mar. 15, 2012, 59 pages.
Notice of Opposition against European Patent EP 1740217, granted on Jun. 15, 2011. Opposition filed by Pfizer Inc. On Mar. 14, 2012, 22 pages.
Pichichero et al. (Jan. 2005) "Comparative trial of the safety and immunogenicity of quadrivalent (A, C, Y, W-135) meningococcal polysaccharide-diphtheria conjugate vaccine versus quadrivalent polysaccharide vaccine in two- to ten-year-old children," Pediatr Infect Dis J. 24(1):57-62.
Pizza et al. (2000). "Identification of Vaccine Candidates Against Serogroup B Meningococcus by Whole-Genome Sequencing," Science 287(5459):1816-1820.
Pizza et al. (2008) "Factor H-binding protein, a unique meningococcal vaccine antigen" Vaccine 26S:I46-8.
Progress through the Sanger Institute FTP server (May 12, 2009), 15 pages.
PSORT analysis of 200 of the sequences disclosed in PCT/US99/09346 (Jan. 1, 2010), 209 pages.
PSORT analysis of SEQ ID Nos. 4 and 6, and of 'Contig295' 300mer (May 8, 2009), 5 pages.
PSORT prediction result for SEQ ID No. 2 (Mar. 30, 2010), 1 page.
Rennels et al. (May 2004) "Dosage escalation, safety and immunogenicity study of four dosages of a tetravalent meninogococcal polysaccharide diphtheria toxoid conjugate vaccine in infants," The Pediatric Infectious Disease Journal 23(5):429-435.
Rennels et al. (Oct. 2002) "Dose escalation, safety and immunogenicity study of a tetravalent meninogococcal polysaccharide diphtheria conjugate vaccine in toddlers," The Pediatric Infectious Disease Journal 21(10):978-979.
Response to Communication, filed in EP Application No. 07075161.5. Oct. 28, 2009.
Rinaudo et al. (2009). "Vaccinology in the genome era", The Journal of Clinical Investigation, 119(9):2515-2525.
Romero et al., "Current status of Meningococcal group B vaccine candidates: capsular or noncapsular?" *Clin. Microbiol. Rev.* 7(4):559-575, 1994.
Sanger Centre's "Projects" website as of Dec. 10, 1997 as retrievable via http://web.archive.org.
Scarselli et al. (Feb. 13, 2009). "Epitope Mapping of a Bactericidal Monoclonal Antibody against the Factor H Binding Protein of *Neisseria meningitides*," Journal of Molecular Biology 386(1):97-108.
Schneider et al. (Apr. 16, 2009) "*Neisseria meningitidis* recruits factor H using protein mimicry of host carbohydrates," Nature 458(7240):890-893.
Sequence for "Putative Lipoprotein [*Neisseria Meningitidis* Z2491]," NCBI Reference Sequence: YP_002342062.1, Mar. 30, 2000.
Serruto et al. (2009). "Genome-based approaches to develop vaccines against bacterial pathogens," Vaccine 27:3245-3250.
Supplemental Submissions in Opposition against European Patent EP 1645631, granted on Oct. 24, 2007. Opposition filed on May 25, 2010. 28 pages.
Supplementary Declaration by Dr. Julian Parkhill, dated May 10, 2010, submitted in opposition proceedings for EP1645631, 4 pages.
Telford et al. (2003). "Genomic and Proteomics in Vaccine Design", in *New Bacterial Vaccines*, edited by Ellis et al. Kleweur Academic/Plenum Publishers, USA. pp. 1-11.
Tettelin et al. (Mar. 10, 2000). "Complete Genome Sequence of *Neisseria meningitidis* Serogroup B Strain MC58," Science 287(5459):1809-1815.
The printed output from the NCBI open reading frame finder (Oct. 20, 2008), 12 pages.
United States Office Action mailed on Feb. 11, 2009, for U.S. Appl. No. 10/181,600, filed Jan. 17, 2001, 5 pages.
United States Office Action mailed on Jul. 24, 2008, for U.S. Appl. No. 10/181,600, filed Jan. 17, 2001, 23 pages.
United States Office Action mailed on Jul. 7, 2009, for U.S. Appl. No. 10/181,600, filed Jan. 17, 2001, 23 pages.
U.S. Appl. No. 60/098,685, "*Neisseria* Spp, Polypeptide, Gene Sequence and Uses Thereof," filed Sep. 1, 1998.
Welsch et al. (2004). "Protective Activity of Monclonal Antibodies to Genome-Derived Neisserial Antigen 1870, a *Neisseria meningitidis* Candidate Vaccine," *The Journal of Immunology* 172: 5606-5615.
Welsch et al. (2007) "A novel mechanism for complement-mediated killing of encapsulated *Neisseria meningitidis* elicited by monoclonal antibodies to factor H-binding protein (genome-derived Neisserial antigen 1870)" Molecular Immunology 44(1-3):256.
Welsch et al. (Apr. 1, 2008). "Complement-dependent synergistic bactericidal activity of antibodies against factor H-binding protein, a sparsely distributed meningococcal vaccine antigen," J Infect Dis 197(7):1053-1061.
Zhu et al. (2005) "Evaluation of recombinant lipidated P2086 protein as a vaccine candidate for group B *Neisseria meningitidis* in a murine nasal challenge model," Infect Immun 73(10):6838-45.
Zollinger (1997). "New and Improved Vaccines Against Meningococcal Disease" in New Generation Vaccines, 2nd Ed., edited by Levine et al., Marcel Dekker, New York. pp. 469-488.
"Appendix I—Percentage identity of seq ID#114, 216 of W003063766 vs sequences of W003063766 calculated using Vector NTI Advance 9.1," submitted with Pfizer's opposition statement against EP 1562983 on Jul. 1, 2014, 3 pages.
"Appendix II—Percentage identity of seq 50-60 of W003063766 vs seqs 224-252 of W003063766," submitted with Pfizer's opposition statement against EP 1562983 on Jul. 1, 2014, 1 pages.
"Appendix III—Percentage identity of seq ID#24, 33, 41 of W02004048404 vs sequences of W003063766 calculated using Vector NTI Advance 9.1," submitted with Pfizer's opposition statement against EP 1562983 on Jul. 1, 2014, 3 pages.
"Appendix IV showing absence of SEQ ID No. 70-72 and presence of SEQ ID No. 73 of the Patent in Seq. 110 and Seq. 212 of D1," submitted with Pfizer's opposition statement against EP 1562983 on Jul. 1, 2014, 4 pages.
Aderson et al. (2010). "Effectiveness of a bivalent factor H binding protein vaccine across *Neisseria meningitidis* serogroups," 17th International Pathogenic *Neisseria* Conference 2010, p. 196.
Ala'Aldeen et al. (2010) "Human antibody response to the meningococcal factor H binding protein (LP2086) during invasive disease, colonization and carriage," Vaccine 28:7667-75.
Ambrose et al. (2006). "Characterization of LP2086 expression in *Neisseria meningitidis*," 15th International Pathogenic *Neisseria* Conference 2006, p. 103.
Anderson et al. (2008). "Functional cross-reactive antibodies are elicited by a group B *Neisseria meningitidis* bivalent recombinant lipidated LP2086 vaccine in cynomolgusmacaques," 16th International Pathogenic *Neisseria* Conference (IPNC) P100, pp. 170-171.
Anderson et al. (2009). "Epidemiology of the serogroup B *Neisseria meningitidis* (MnB) factor H binding protein and implications for vaccine development," European Society for Paediatric Infectious Disease Symposium 2009, p. 505.
Anderson et al. (2009). "Development of a factor H binding protein vaccine for borad protection against invasive *Neisseria meningitidis* serogroup B (MnB) disease," 10th European Meningococcal Disease Society Congress 2009, p. 39.
Anderson et al. (2012). "Potential impact of the bivalent rLP2086 vaccine on *Neisseria meningitidis* invasive disease and carriage isolates in two adolescent populations," European Society for Paediatric Infectious Disease Symposium 2012, p. 807.

(56) References Cited

OTHER PUBLICATIONS

Anderson et al. (2013) "Potential impact of the bivalent rLP2086 vaccine on *Neisseria meningitidis* carriage and invasive serogroup B disease," Hum Vacc Immunotherap 9:471-9.

Appendix I to Statement of Grounds of Appeal filed by df-mp on Sep. 28, 2012, in relation to EP1645631, 1 page.

Appendix II to Statement of Grounds of Appeal filed by df-mp on Sep. 28, 2012, in relation to EP1645631, 2 pages.

Baylor et al. (2002). "Aluminum salts in vaccines—US perspective," Vaccine 20:S18-S23.

Beernick (Jul. 2010) "Impaired immunogenicity of a meningococcal factor H-binding protein vaccine engineered to eliminate factor h binding," Clin Vac Immunol 17(7):1074-1078.

BenMohamed et al. (2002). "Lipopeptide vaccines-yesterday, today, and tomorrow," Lancet 2(7):425-431.

Bentley et al. (2004). Identification of two immunologically distinct domains on the LP2086 outer membrane lipoprotein of *Neisseria meningitidis*, 14th International Pathogenic *Neisseria* Conference 2004, p. 144.

Bouvier et al. (1991). "A gene for a new lipoprotein in the dapA-purC interval of the *Escherichia coli* chromosome," J Bacteriol 173(17):5523-5531.

Chen, et al. (1994). "Determination of the optimal aligned spacing between the Shine-Dalgarno sequence and the translation initiation codon of *Escherichia coli* mRNAs," Nucleic Acids Res. 22(23):4953-4957.

Clinical Trial No. NCT00500032, (2007). "Blood collection for use in serological assay development from healthy adult volunteers," U.S. National Institutes of Health, retrieved online at <http://clinicaltrials.gov/ct2/show/NCT00500032?term=NCT00500032&rank=1>.

Clinical Trial No. NCT00808028, (2008). "A study evaluating safety and immunogenicity of meningococcal B rlp2086 vaccine in adolescents," U.S. National Institutes of Health, retrieved online at <http://clinicaltrials.gov/ct2/show/NCT00808028?term=NCT00808028&rank=1>.

Cohn et al. (2010). "Potential Impact of Serogroup B Vaccines: Prevalence of candidate vaccine antigens among invasive *Neisseria meningitidis* isolates in the United States," 17th International Pathogenic *Neisseria* Conference 2010, p. 77.

Comanducci, M. (2002). "NadA, a Novel Vaccine Candidate of *Neisseria meningitides*," Journal of Experimental Medicine 195(11):1445-1454.

Cordis, "Preparation of meningococcal antigens," posted online on Feb. 2, 2005, 2 pages.

Declaration by Dr. Ellen Murphy, Ph.D., dated Sep. 14, 2011, submitted in opposition proceedings for EP1645631, 4 pages.

Declaration by E. Richard Moxon dated Feb. 16, 2013, submitted in opposition proceedings for EP1645631, 5 pages.

Declaration by Emilio A. Emini, Ph.D., dated Nov. 2, 2011, submitted in opposition proceedings for EP1645631, 5 pages.

Declaration by Isabel Delany, dated Feb. 18, 2013, submitted in opposition proceedings for EP1645631, 5 pages.

Declaration by Prof. Paul Dunman, Ph.D., dated Sep. 25, 2012, submitted in opposition proceedings for EP1645631, 14 pages.

Declaration by Rino Rappuoli, dated Oct. 13, 2011, submitted in opposition proceedings for EP1645631, 5 pages.

Declaration by Vega Masignani dated Feb. 18, 2013, submitted in opposition proceedings for EP1645631, 4 pages.

Delgado et al. (2007). "Lipoprotein NMB0928 from *Neisseria meningitidis* serogroup B as a novel vaccine candidate," Vaccine 25:8420-8431.

Dinthilhac and Claverys (1997). "The adc locus, which affects competence for genetic transformation in *Streptococcus pneumoniae*, encodes an ABC transporter with a putative lipoprotein homologous to a family of streptococcal adhesins," Res Microbiol 148:119-131.

Dlawer et al. (2010). "Human antibody responses to the meningococcal factor H binding protein LP2086 during invasive disease," 17th International Pathogenic *Neisseria* Conference 2010, p. 130.

Facts and Submissions dated May 21, 2012, in relation to EP1645631, 30 pages.

Fraser et al. (1997). "Genomic sequence of a lyme disease spirochaete, *Borrelia burgdorferi*," Nature 390:580-586.

Fraser et al. (1998). "Complete genome sequence of *Treponema pallidum*, the syphilis spirochete," Science 281:375-388.

GenPept accession No. AAF42204, "hypothetical protein NMB1870 [*Neisseria meningitidis* MC58]," retrieved on Sep. 26, 2012, 2 pages.

Giuliani et al. (2010). "Measuring antigen-specific bactericidal responses to a multicomponent vaccine against serogroup B meningococcus," Vaccine 28:5023-5030.

Gold and Stormo (1987). "Translation Initiation", in *Escherichia* con and *Salmonella typhimurium*, Cellular and Molecular Biology, Ed. Neidhardt, pp. 1302-1307.

Goldblatt (1998) "Recent developments in bacterial conjugate vaccines" J. Med Microbiol. 47:563-567.

Gorringe et al. (2009). "16th International Pathogenic *Neisseria* Conference: recent progress towards effective meningococcal disease vaccines," Human Vaccines 5(2):53-56.

Grandi (2005). "Reverse vaccinology: a critical analysis," in Encyclopedia of Genetics, Genomics, Proteomics and Bioinformatics, pp. 1322-1326.

Granoff, DM. (2009). Relative importance of complement-mediated bactericidal and opsonic activity for protection against meningococcal disease. Vaccine 27(Supplement 2): B117-B125.

Harris et al. (2008). "Development and qualification of serum bactericidal assays for *Neisseria meningitidis* serogroup B," 16th International Pathogenic *Neisseria* Conference 2008, p. 268-269.

Harris et al. (2010). "Robustness of the Serum Bactericidal Activity (SBA) Assay for *Neisseria meningitidis* serogroup B," 17th International Pathogenic *Neisseria* Conference 2010, p. 169.

Harris et al. (2011) "Preclinical evidence for the potential of a bivalent fHBP vaccine to prevent *Neisseria meningitidis* serogroup C disease," Human Vaccines 7:1 (suppl) 1-7.

Hayashi and Wu, "Identification and characterization of lipid-modified proteins in bacteria," Chapter 10 in Lipid Modifications of Proteins: A Practical Approach, Hooper and Turner (eds.), published in 1992, 27 pages.

Hem et al. (1995). "Structure and properties of aluminum-containing adjuvants," Vaccine Design. Subunit and Adjuvant Approach, pp. 249-276.

Hodge et al. (2006). "Development of a luminex-based meningococcal rLP2086-specific human IgG assay," 15th International Pathogenic *Neisseria* Conference 2006, p. 113.

Hoiseth et al. (2008). "LP2086 and MLST distribution in epidemiologically relevant strains of serogroup B *Neisseria meningitidis*," 16th International Pathogenic *Neisseria* Conference 2008, p. 205.

Hung et al. (2011). "The *Neisseria meningitidis* macrophage infectivity potentiator protein induces cross-strain serum bactericidal activity and is a potential serogroup B vaccine candidate," Infect Immun 79(9):3784-3791.

Hunter (2002). "Overview of vaccine adjuvants: present and future," Vaccine 20:S7-S12.

Jansen et al. (2008). "Bivalent recombinant LP2086 vaccine to provide broad protection against *Neisseria meningitidis* B disease: immunological correlates of protection and how to assess coverage against invasive MnB strains," 16th International Pathogenic *Neisseria* Conference 2008, p. 80-81.

Jansen et al. (2009). "Development of a bivalent factor H binding protein vaccine to broadly protect against invasive *Neisseria meningitides* serogroup B (MnB) disease," European Society for Paediatric Infectious Disease Symposium 2009, p. 311.

Jansen et al. (2010). "Estimating effectiveness for *Neisseria meningitidis* serogroup B (MnB) vaccine candidates composed of non-serogroup specific antigens," 17th International Pathogenic *Neisseria* Conference 2010, p. 37.

Jansen et al. (2011). "Monitoring the Breadth of Coverage of Meningococcal Vaccines: An Overview and Progress Update on the Pfizer Bivalent LP2086 Vaccine Program," 14th Annual Conference on Vaccine Research, 2011, p. 74.

Jiang et al. (2003). "Using rate of acid neutralization to characterize aluminum phosphate adjuvant," Pharma Dev Tech 8(4):349-356.

(56) References Cited

OTHER PUBLICATIONS

Jiang et al. (2006). "Serum IgG response induced by a bivalent recombinant LP2086 provides broad protection against serogroup B *Neisseria meningitidis*," 15th International Pathogenic *Neisseria* Conference 2006, p. 113.
Jiang et al. (2008). "Prediction of broad vaccine coverage for a bivalent rLP2086 based vaccine which elicits serum bactericidal activity against a diverse collection of serogroup B meningococci," 16th International Pathogenic *Neisseria* Conference 2008, p. 57-58.
Johnson et al. (1999). "Analysis of the human Ig isotype response to lactoferrin binding protein A from *Neisseria meningitidis*," FEMS Immun. Med. Microbial. 25(4): 349-354.
Jones et al. (2009). "Generation of human serum complement lots that perform consistently for use in *Neisseria meningitidis* serogroup B (MnB) vaccine clinical trials," European Society for Paediatric Infectious Disease Symposium 2009, p. 566.
Juncker et al. (2003). "Prediction of lipoprotein signal peptides in gram-negative bacteria," Protein Sci 12:1652-1662.
Koeberling et al. (2009). "Meningococcal outer membrane vesicle vaccines derived from mutant strains engineered to express factor H binding proteins from antigenic variant groups 1 and 2," Clin Vac Immunol, 16(2):156-162.
Liebl et al. (1997). "Properties and gene structure of the Thermotoga maritima alpha-amylase AmyA, a putative lipoprotein of a hyperthermophilic bacterium," J Bacteriol 179(3):941-948.
Makela (2003). "Conjugate vaccines—a breakthrough in vaccine development," Southeast Asian J Trop Med Public Health 34(2):249-253.
Marshall et al. (2008). "A randomized, placebo-controlled, double-blind, phase 1 trial of ascending doses of meningococcal group B rLP2086 vaccine in healthy adults," 16th International Pathogenic *Neisseria* Conference 2008, p. 271-272.
Marshall et al. (2011). "Phase I randomised controlled clinical trial of safety and immunogenicity of a meningococcal B bivalent LP2086 vaccine in healthy toddlers," European Society for Paediatric Infectious Disease Symposium 2011, p. 189.
Marshall et al. (2012) "Safety and immunogenicity of a meningococcal B bivalent rLP2086 vaccine in healthy toddlers aged 18-36 months: A phase 1 randomized-controlled clinical trial," Ped Infect Dis J 31:1061-8.
Marshall et al. (2013) "A phase 2 open-label safety and immunogenicity study of a meningococcal B bivalent rLP2086 vaccine in healthy adults," Vaccine 31:1569-75.
Mascioni et al. (2008). "Determination of the domain and solution structure of rLP2086, a meningococcal vaccine candidate and human factor H binding protein," 16th International Pathogenic *Neisseria* Conference 2008, p. 77-78.
Mascioni et al. (2009) "Structural basis for the immunogenic properties of the meningococcal vaccine candidate LP2086," J Biol Chem 284:8738-46.
Mascioni et al. (2010) "NMR dynamics and antibody recognition of the meningococcal lipidated outer membrane protein LP2086 in micellar solution," Biochim Biophys Acta 1798:87-93.
McNeil et al. (2009) "Detection of LP2086 on the cell surface of *Neisseria meningitidis* and its accessibility in the presence of serogroup B capsular polysaccharide," Vaccine 27:3417-21.
McNeil et al. (2010). "Anti-fHBP antibodies elicited after immunization with a recombinant fHBP vaccine candidate (rLP2086) can displace human Factor H from the surface of Serogroup B Meningococci," 17th International Pathogenic *Neisseria* Conference 2010, p. 94.
McNeil et al. (2013) "Role of factor H binding protein in *Neisseria meningitidis* virulence and its potential as a vaccine candidate to broadly protect against meningococcal disease," Microbiol Mol Biol Rev 77:234.
Milagres et al. (1998). "Specificity of bactericidal antibody response to serogroup B meningococcal strains in Brazilian children after immunization with an outer membrane vaccine," Infection and Immun. 66(10): 4755-4781.

Munkley, et al. (1991). "Blocking of bactericidal killing of *Neisseria meningitidis* by antibodies directed against slacc 4 outer membrane proteins," Microbial Pathogenesis 11: 447-452.
Murphy et al. (2008). "Sequence diversity of vaccine candidate LP2086 in *Neisseria meningitidis* serogroup B strains causing invasive disease," 16th International Pathogenic *Neisseria* Conference 2008, p. 61.
Murphy et al. (2010). "Prevalence of Factor H Binding Protein (fHBP) Variants in *N. meningitidis* Carriage Isolates," 17th International Pathogenic *Neisseria* Conference 2010, p. 96.
Novartis (Jan. 22, 2013) "Novartis receives EU approval for Bexsero®, first vaccine to prevent the leading cause of life-threatening meningitis across Europe," Media Release, 3 pages.
Pajon et al. (2012). "Design of meningococcal factor H binding protein mutant vaccines that do not bind human complement factor H," Infect Immun 80:2667-2677.
Petrovsky et al. (2004). "Vaccine adjuvants: Current state and future trends," Immunol and Cell Biol 82:488-496.
Pettersson, et al. (2006). "Vaccine potential of the *Neisseria meningitidis* lactoferrin-binding proteins LbpA and LbpB," Vaccine 24(17):3545-3557.
Pillai et al. (2005) "Outer membrane protein (OMP) based vaccine for *Neisseria meningitidis* serogroup B," Vaccine 23(17-18):2206-2209.
Prosite, "ScanProsite Results Viewer: USERSEQ1 (280aa)," retrieved on Jun. 21, 2012, 1 page.
Pugsley (1993). "The complete general secretory pathway in gram-negative bacteria," Microbiological Rev 5(1):50-108.
Response to Appeal filed by Carpmaels & Ransford on Feb. 18, 2013, in relation to EP1645631, 21 pages.
Response to Appeal filed by df-mp on Feb. 18, 2013, in relation to EP1645631, 28 pages.
Richmond et al. (2008). "A randomized, observer-blinded, active control, phase 1 trial of meningococcal serogroup B rLP2086 vaccine in healthy children and adolescents aged 8 to 14 years," 16th International Pathogenic *Neisseria* Conference 2008, p. 270-271.
Richmond et al. (2010). "Safety & immunogenicity of serogroup B *Neisseria meningitidis* (MnB) rLP2086 vaccine in adults and adolescent subjects: overview of 3 clinical trials," 17th International Pathogenic *Neisseria* Conference 2010, p. 37.
Richmond et al. (2011). "Phase II randomised controlled trial of safety and immunogenicity of a meningococcal B bivalent vaccine (rLP2086) in healthy adolescents," European Society for Paediatric Infectious Disease Symposium 2011, p. 192.
Richmond et al. (2012) "A bivalent *Neisseria meningitidis* recombinant lipidated factor H binding protein vaccine in young adults: Results of a randomized, controlled, dose-escalation phase 1 trial," Vaccine 30(43):6163-74.
Richmond et al. (2012a) "Safety, immunogenicity, and tolerability of meningococcal serogroup B bivalent recombinant lipoprotein 2086 vaccine in healthy adolescents: a randomized, single-blind, placebo-controlled, phase 2 trial," Lancet Infect Dis 12:597-607.
Seeber et al. (1991). "Predicting the adsorption of proteins by aluminum-containing adjuvants," Vaccine 9(3):201-203.
Seib et al. (2010). "Influence of serogroup B meningococcal vaccine antigens on growth and survival of the mengococcus in vitro and in ex vivo and in vivo models of infection," Vaccine 28(12):2416-2427.
Sheldon et al. (2011). "Phase 1, Randomized, Open-Label, Study to Assess the Safety and Immunogenicity of Serogroup B *Neisseria Meningitidis* (Mnb) rLP2086 Vaccine in Healthy Adults," 14th Annual Conference on Vaccine Research, 2011, p. 59-60.
Sheldon et al. (2012) "A phase 1, randomized, open-label, active-controlled trial to assess the safety of a meningococcal serogroup B bivalent rLP2086 vaccine in healthy adults," Hum Vacc Immunotherap 8:1-8.
Shevchik et al. (1996). "Characterization of pectin methylesterase B, an outer membrane lipoprotein of *Erwinia chrysanthemi* 3937," Mole Microbiol 19(3):455-466.
Statement of Grounds of Appeal filed by Carpmaels & Ransford on Oct. 4, 2012, in relation to EP1645631, 9 pages.
Statement of Grounds of Appeal filed by df-mp on Sep. 28, 2012, in relation to EP1645631, 54 pages.

(56) References Cited

OTHER PUBLICATIONS

Supplementary declaration by Ellen Murphy dated Sep. 26, 2012, submitted in opposition proceedings for EP1645631, 3 pages.
Supplementary declaration by Prof. Paul Dunman, Ph.D., dated Sep. 25, 2012, submitted in opposition proceedings for EP1645631, 14 pages.
Sutcliffe and Russell (1995). "Lipoproteins of gram-positive bacteria," J Bacteriol 177(5):1123-1128.
Tan et al. (2010). "Advances in the development of vaccines against *Neisseria meningitidis*," NEJM 362(16):1511-1520.
Tavano et al. (2011). "Mapping of the *Neisseria meningitidis* NadA cell-binding site: Relevance of predicted α-helices in the NH2-terminal and dimeric coiled-coil regions," J Bacteriol 193(1):107-115.
TIGR website as of 1998, 8 pages.
von Heijne (1989). "The structure of signal peptides from bacterial lipoproteins," Protein Engineering 2(7):531-534.
Wang et al. (2010). "Prevalence and genetic diversity of candidate vaccine antigens among invasive *Neisseria meningitidis* isolates in the United States," 17th International Pathogenic *Neisseria* Conference 2010, p. 122.
Woods, et al. (1987). "Resistance to meningococcemia apparently conferred by anti-H.8 monoclonal antibody is due to contaminating endotoxin and not to specific immunoprotection," Infection and Immunity 55(8):1927-1928.
World Health Organization (2002). "Emergence of W135 Meningococcal Disease," Report of a WHO Consultation, Geneva, Sep. 17-18, 2001, 73 pages. Retrieved from the Internet at: http://www.who.int/entity/csr/resources/publications/meningitis/whocdscsrgar20021.pdf.
Wu et al. (1996). "A protein class database organized with ProSite protein groups and PIR superfamilies," J Comp Biol 3(4):547-561.
York et al. (2010). "fHBP epidemiology of invasive meningococcal B isolates from Spain and Germany: age based," 17th International Pathogenic Neisseria Conference 2010, p. 109.
Zhu et al. (2004). "Evaluation of the purified recombinant lipidated P2086 protein as a vaccine candidate for group B *Neisseria meningitidis* in a murine nasal challenge model," 14th International Pathogenic *Neisseria* Conference 2004, p. 199.
Zhu et al. (2006) "Intranasal immunization of mice with recombinant lipidated P2086 protein reduces nasal colonization of group B *Neisseria meningitidis*," Vaccine 24:5420-5.
Zhu et al. (2006). "Effective immunization strategy against group B *Neisseria meningitidis* using purified recombinant lipidated P2086 protein," 15th International Pathogenic *Neisseria* Conference 2006, p. 47.
Zlotnick et al. (2009). "Epidemiology of the serogroup B *Neisseria meningitidis* (MnB) factor H binding protein in strains sampled from Spain and Germany in the years 2001-2006," 10th European Meningococcal Disease Society Congress 2009, p. 81.
Zlotnick et al. (2010). "Biochemical and biophysical analysis indicates conformation plays an important role in the binding of hfH and antibodies to the fHBP of *N. meningitidis*," 17th International Pathogenic *Neisseria* Conference 2010, p. 38.
Adams (1996). "Should Non-Peer-Reviewed Raw DNA Sequence Data Release Be Forced on the Scientific Community?," Science, 274: 534-536.
Biswas et al. (1995). "Characterization of IbpA, the structural gene for a lactoferrin receptor in *Neisseria gonorrhoeae*," Infection and Immunity, 63(8): 2958-2967.
Blattner et al. (1997). "The complete genome sequence of *Escherichia coli* K-12," Science 277 (5331): 1453-1474.
Decision to refuse a patent application, filed in the Opposition against EP1645631, dated Apr. 28, 2009, 7 pages.
Declaration by Dr. Julian Parkhill, filed in the Opposition against EP1645631, dated Jul. 10, 2014, 5 pages.
Declaration by Ellen Murphy, filed in the Opposition against EP1645631, dated May 12, 2014, 3 pages.
Elzanowski et al. (2013). "The Genetic Codes, a compilation," Retrived from http://www.bioinformatics.org/JaMBW/2/3/TranslationTables.html.

Holst et al. (2014). "Variability of genes encoding surface proteins used as vaccine antigens in meningococcal endemic and epidemic strain panels from Norway," Vaccine 32:2722-2731.
Mahadevan (1998). "Reconciling the spectrum of Sagittarius A* with a two-temperature plasma model," Nature 394:651-653.
Meyer et al. (1984). "Pilus genes of *Neisseria gonorrheae*: Chromosomal organization and DNA sequence," Proc. Nail. Acad. Sci. USA 81: 6110-6114.
Minutes of the oral proceedings, filed in the Opposition against EP1645631, dated Februray 11, 2014, 4 pages.
Opponent's Response to the Patentee's Submission dated Feb. 18, 2013, filed in the Opposition against EP1645631, dated Jul. 24, 2014, 34 pages.
ORF Finder (2013). "Bacterial Code," Retrieved from http://www.ncbi.nlm.nih.gov/gorf/gorf.html, 3 pages.
Sprengart et al. (1997). "Functional importance of RNA interactions in selection of translation initiation codons," Molecular Microbilogy, 24(1): 19-28.
Summons to oral proceedings pursuant to Rule 115(1) EPC, filed in the Opposition against EP1645631, dated Nov. 11, 2013, 12 pages.
Swaminathan (1996). "Molecular cloning of the three base restriction endonuclease R.CviJI from eukaryotic Chlorella virus IL-3A. Swaminathan," Nucleic Acids Research, 24(13): 2463-2469.
Gene Browser, Nature Technology Corporation, filed in the Opposition against EP1645631, dated Jun. 26, 2013, 6 pages.
TIGR Microbal Database, filed in the Opposition against EP1645631, dated Jun. 20, 2012, 14 pages.
Submission of the Patentee of Jul. 6, 2012, filed Jun. 24, 2014, in the Opposition against EP1645631, 4 pages.
Notice of Opposition against EP 1562983, filed on Jul. 1, 2014, 23 pages.
Notice of Opposition against EP1645631, filed in the Opposition against EP1645631, dated Jul. 23, 2008, 25 pages.
Patentee's Submissions under Rule 116 EPC, filed in the Opposition against EP1645631, dated Sep. 13, 2011, 13 pages.
Opponents Final Written Submission in Preparation of Oral Proceedings, filed in the Opposition against EP1645631, dated Sep. 14, 2011, 28 pages.
Opponent's Further Submission in Preparation of the Oral Proceedings, filed in the Opposition against EP1645631, dated Nov. 3, 2011, 6 pages.
Supplementary Submission to the Grounds of Appeal, filed in the Opposition against EP1645631, dated Sep. 28, 2012, 2 pages.
Interlocutory decision in opposition proceedings, filed in the Opposition against EP1645631, dated May 21, 2012, 82 pages.
Database UniProt (Oct. 1, 2000), "SubName: Full=Uncharacterized protein" retrieved from EBI, accession no. Q9JXV4 Database accession no. Q9JXV4.
Decision revoking the European Patent, filed in opposition against EP1976990, dated Nov. 11, 2013, 15 pages.
Experimental data: expression of NspA, '287' and '741' on 3 strains of bacteria, filed in opposition against EP1534326, dated Aug. 4, 2010. 2 pages.
Koeberling et al. (2008). "Bactericidal antibody responses elicited by a meningococcal outer membrane vesicle vaccine with overexpressed factor H-binding protein and genetically attenuated endotoxin," J. Infect. Dis., 198(2):262-270.
Kovacs-Simon et al. (2011). "Lipoproteins of Bacterial Pathogens," Infect Immun 79(2):548561.
Lewis et al. (2010). "The meningococcal vaccine candidate neisserial surface protein A (NspA) binds to factor H and enhances meningococcal resistance to complement," PLoS Pathogens 6(7):e1001027.
Liechti et al. (2012). "Outer membrane biogenesis in *Escherichia coli*, *Neisseria meningitidis*, and *Helicobacter pylori*: paradigm deviations in H. pylori," Front Cell and Infect Microbiol 2:article 29.
Lindblad, (2004). "Aluminium compounds for use in vaccines," Immunol Cell Biol.,82(5):497-505.
Madico et al. (2006). "The meningococcal vaccine candidate GNA1870 binds the complement regulatory protein factor H and enhances serum resistance," J Immunol 177(1):501-510.
Notice of Opposition filed May 24, 2012, filed in opposition against EP1976990, 19 pages.

(56) References Cited

OTHER PUBLICATIONS

Novartis (Jun. 9, 2011). "Novartis candidate vaccine Bexsero® shows significant potential in providing broad coverage against meningococcal serogroup B infections." Media Release, 6 pages.

Seib et al. (2011). "Characterization of Diverse Subvariants of the Meningococcal Factor H (fH) Binding Protein for Their Ability to Bind fH, to Mediate Serum Resistance, and To Induce Bactericidal Antibodies," Infect Immun, 79(2):970-81.

U.S. Appl. No. 60/647,911, "GNA 1870-based vesicle vaccines for broad spectrum protection against diseases caused by Neisseria meningitidis," filed Jan. 27, 2005.

Vesikari et al. (2013). "Immunogenicity and safety of an investigational multicomponent, recombinant, meningococcal serogroup B vaccine (4CMenB) administered concomitantly with routine infant and child vaccinations: results of two randomized trials," Lancet 381:625-35.

Voulhoux and Tommassen (2002). "Transport of lipoproteins to the cell surface in *Neisseria meningitidis*," 13th International Pathogenic Neisseria Conference 2002, p. 31.

Written Submission to Oral Proceedings, filed in opposition against EP1976990, dated Jul. 24, 11 pages.

Zollinger et al. (2010). "Design and evaluation in mice of a broadly protective meningococcal group B native outer membrane vesicle vaccine," Vaccine, 28(31):5057-5067.

Donnelly et al. (2010). "Qualitative and quantitative assessment of meningococcal antigens to evaluate the potential strain coverage of protein-based vaccines," Proc Natl Aced Sci U S A, 107(45):19490-5.

Plikaytis et al. (2012). "Interlaboratory standardization of the sandwich enzyme-linked immunosorbent assay designed for MATS, a rapid, reproducible method for estimating the strain coverage of investigational vaccines," Clin Vaccine Immunol, (10):1609-17.

\* cited by examiner

FIGURE 10

```
                                 1
type 1  -19:MNRTAFCCLSLTTALILTACS....SGGGGVAADIGAGLADALTAPLDH: 26
type 2  -19:MNRTAFCCLSLTAALILTACS....SGGGGVAADIGAGLADALTAPLDH: 26
type 3  -19:MNRTAFCCLSLTTALILTACSSGGGSEGGGVAADIGTGLADALTAPLDH: 31 type 1   27:KDKGLQSLVLDQSVRKNEKLKLAAQGAEKTYGNED...SLNTGKLANDKV: 73
type 2   27:KDKSLQSLVLDQSVRKNEKLKLAAQGAEKTYGNED...SLNTGKLANDKV: 73
type 3   32:KDKELKSLVLEDSIPQGTLILSAQGAEKTYKAEDKDNSLNTGKLANDKV: 81 type 1   74:SRFDFIRQIEVDGQLITLESGEEFQIYKQSHSALTAFQIEQIQDSEHGK*:123
type 2   74:SRFDFIRQIEVDGQLITLESGEEFQIYKQDHSAVVALQIEKINNPDKIDSL:123
type 3   82:SRFDFQKIEVDGQLITLASGEEFQIYKQHSAVVALQIEKINNPDKIDSL:131 type 1  124:IAKRQERIGDILGEHISFDKLPGGEATRGDAFGSDDAGGKLTYTIDFA:173
type 2  124:INQRSFLVSGLGGEHTAFNQLPDGKAEYHGKAFSSDDAGGKLTYTIDFA:172
type 3  132:INQRSFLVSGLGGEHTAFNQLPGGKAEYHGKAFSSDDPNGRLFYSIDFT:180 type 1  174:AKQGNGKIEHLKSPELIVELAAALIKPDGRHAVISGSVLINQAEKGSYS:223
type 2  173:AKQGHGKIEHLKTPEQNVELAAAELKADEKSHAVILGDTRYGSEEKGTYI:222
type 3  181:AKQGEYGRIEHLKTLEQNVELAAAELKADEKSHAVILGDTRYGSEEKGTYI:230 type 1  224:LGTFGDRAQEIAGSAIVKTVAGTRHIGIAPKQ:255
type 2  223:LALFGDRAQEIAGSAIVKIGEKVHEIGIAGKQ:254
type 3  231:LALFGDRAQEIAGSAIVKIGEKVHEIGIAGKQ:262
```

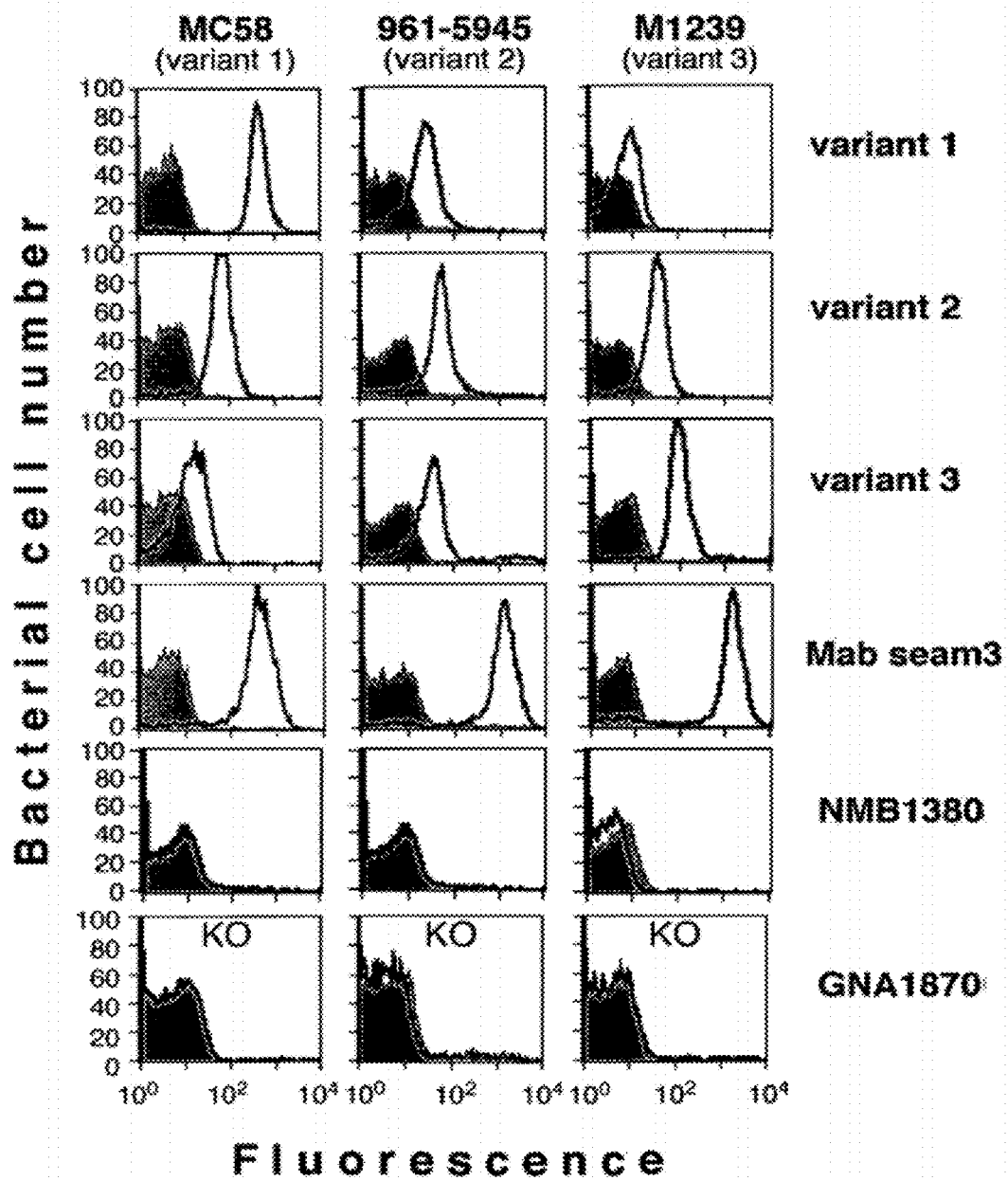

SEQUENCE LISTING

<160> NUMBER OF SEQ ID NOS: 144

<210> SEQ ID NO 1
<211> LENGTH: 274
<212> TYPE: PRT
<213> ORGANISM: Neisseria meningitidis

<400> SEQUENCE: 1

```
Met Asn Arg Thr Ala Phe Cys Cys Leu Ser Leu Thr Thr Ala Leu Ile
 1               5                  10                  15

Leu Thr Ala Cys Ser Ser Gly Gly Gly Val Ala Ala Asp Ile Gly
             20                  25                  30

Ala Gly Leu Ala Asp Ala Leu Thr Ala Pro Leu Asp His Lys Asp Lys
         35                  40                  45

Gly Leu Gln Ser Leu Thr Leu Asp Gln Ser Val Arg Lys Asn Glu Lys
     50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
                100                 105                 110

Gly Glu Phe Gln Val Tyr Lys Gln Ser His Ser Ala Leu Thr Ala Phe
            115                 120                 125

Gln Thr Glu Gln Ile Gln Asp Ser Glu His Ser Gly Lys Met Val Ala
        130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175
```

```
Gly Ser Asp Asp Ala Gly Gly Lys Leu Thr Tyr Thr Ile Asp Phe Ala
            180                 185                 190
Ala Lys Gln Gly Asn Gly Lys Ile Glu His Leu Lys Ser Pro Glu Leu
        195                 200                 205
Asn Val Asp Leu Ala Ala Asp Ile Lys Pro Asp Gly Lys Arg His
210                 215                 220
Ala Val Ile Ser Gly Ser Val Leu Tyr Asn Gln Ala Glu Lys Gly Ser
225                 230                 235                 240
Tyr Ser Leu Gly Ile Phe Gly Gly Lys Ala Gln Glu Val Ala Gly Ser
                245                 250                 255
Ala Glu Val Lys Thr Val Asn Gly Ile Arg His Ile Gly Leu Ala Ala
            260                 265                 270
Lys Gln

<210> SEQ ID NO 2
<211> LENGTH: 274
<212> TYPE: PRT
<213> ORGANISM: Neisseria meningitidis

<400> SEQUENCE: 2

Met Asn Arg Thr Ala Phe Cys Cys Leu Ser Leu Thr Thr Ala Leu Ile
 1               5                  10                  15
Leu Thr Ala Cys Ser Ser Gly Gly Gly Val Ala Ala Asp Ile Gly
            20                  25                  30
Ala Gly Leu Ala Asp Ala Leu Thr Ala Pro Leu Asp His Lys Asp Lys
        35                  40                  45
Gly Leu Gln Ser Leu Met Leu Asp Gln Ser Val Arg Lys Asn Glu Lys
    50                  55                  60
Leu Lys Leu Ala Ala Gln Gly Ala Glu Lys Thr Tyr Gly Asn Gly Asp
65                  70                  75                  80
Ser Leu Asn Thr Gly Lys Leu Lys Asn Asp Lys Val Ser Arg Phe Asp
                85                  90                  95
Phe Ile Arg Gln Ile Glu Val Asp Gly Lys Leu Ile Thr Leu Glu Ser
            100                 105                 110
Gly Glu Phe Gln Val Tyr Lys Gln Ser His Ser Ala Leu Thr Ala Leu
        115                 120                 125
Gln Thr Glu Gln Val Gln Asp Ser Glu Asp Ser Gly Lys Met Val Ala
    130                 135                 140
Lys Arg Gln Phe Arg Ile Gly Asp Ile Ala Gly Glu His Thr Ser Phe
145                 150                 155                 160
Asp Lys Leu Pro Lys Gly Gly Ser Ala Thr Tyr Arg Gly Thr Ala Phe
                165                 170                 175
Gly Ser Asp Asp Ala Gly Gly Lys Leu Thr Tyr Thr Ile Asp Phe Ala
            180                 185                 190
Ala Lys Gln Gly His Gly Lys Ile Glu His Leu Lys Ser Pro Glu Leu
        195                 200                 205
Asn Val Glu Leu Ala Thr Ala Tyr Ile Lys Pro Asp Glu Lys His His
    210                 215                 220
Ala Val Ile Ser Gly Ser Val Leu Tyr Asn Gln Asp Glu Lys Gly Ser
225                 230                 235                 240
Tyr Ser Leu Gly Ile Phe Gly Gly Gln Ala Gln Glu Val Ala Gly Ser
                245                 250                 255
Ala Glu Val Glu Thr Ala Asn Gly Ile His His Ile Gly Leu Ala Ala
            260                 265                 270
```

Lys Gln

<210> SEQ ID NO 3
<211> LENGTH: 274
<212> TYPE: PRT
<213> ORGANISM: Neisseria meningitidis

<400> SEQUENCE: 3

Met Asn Arg Thr Ala Phe Cys Cys Phe Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Val Gln Asp Ser Glu Asp Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Lys Gly Gly Ser Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly His Gly Lys Ile Glu His Leu Lys Ser Pro Glu Leu
        195                 200                 205

Asn Val Glu Leu Ala Thr Ala Tyr Ile Lys Pro Asp Glu Lys Arg His
    210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile His His Ile Gly Leu Ala Ala
            260                 265                 270

Lys Gln

<210> SEQ ID NO 4
<211> LENGTH: 274
<212> TYPE: PRT
<213> ORGANISM: Neisseria meningitidis

<400> SEQUENCE: 4

Met Asn Arg Thr Ala Phe Cys Cys Phe Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys

```
              35                  40                  45
Ser Leu Gln Ser Leu Thr Leu Asp Gln Ser Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
                100                 105                 110

Gly Glu Phe Gln Val Tyr Lys Gln Ser His Ser Ala Leu Thr Ala Leu
                115                 120                 125

Gln Thr Glu Gln Glu Gln Asp Pro Glu His Ser Gly Lys Met Val Ala
                130                 135                 140

Lys Arg Arg Phe Lys Ile Gly Asp Ile Ala Gly Glu His Thr Ser Phe
145                 150                 155                 160

Asp Lys Leu Pro Lys Asp Val Met Ala Thr Tyr Arg Gly Thr Ala Phe
                165                 170                 175

Gly Ser Asp Asp Ala Gly Gly Lys Leu Thr Tyr Thr Ile Asp Phe Ala
                180                 185                 190

Ala Lys Gln Gly His Gly Lys Ile Glu His Leu Lys Ser Pro Glu Leu
                195                 200                 205

Asn Val Glu Leu Ala Thr Ala Tyr Ile Lys Pro Asp Glu Lys His His
210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile His His Ile Gly Leu Ala Ala
                260                 265                 270

Lys Gln

<210> SEQ ID NO 5
<211> LENGTH: 279
<212> TYPE: PRT
<213> ORGANISM: Neisseria meningitidis

<400> SEQUENCE: 5

Met Asn Arg Thr Thr Phe Phe Cys Leu Ser Leu Thr Ala Ala Leu Ile
 1               5                  10                  15

Leu Thr Ala Cys Ser Ser Gly Gly Gly Ser Gly Gly Gly Gly Gly Val
                 20                  25                  30

Ala Ala Asp Ile Gly Ala Gly Leu Ala Asp Ala Leu Thr Ala Pro Leu
                 35                  40                  45

Asp His Lys Asp Lys Gly Leu Gln Ser Leu Thr Leu Asp Gln Ser Val
 50                  55                  60

Arg Lys Asn Glu Lys Leu Lys Leu Ala Ala Gln Gly Ala Glu Lys Thr
 65                  70                  75                  80

Tyr Gly Asn Gly Asp Ser Leu Asn Thr Gly Lys Leu Lys Asn Asp Lys
                 85                  90                  95

Val Ser Arg Phe Asp Phe Ile Arg Gln Ile Glu Val Asp Gly Gln Leu
                100                 105                 110

Ile Thr Leu Glu Ser Gly Glu Phe Gln Val Tyr Lys Gln Ser His Ser
                115                 120                 125

Ala Leu Thr Ala Leu Gln Thr Glu Gln Val Gln Asp Ser Glu Asp Ser
```

```
                130                 135                 140
Gly Lys Met Val Ala Lys Arg Gln Phe Arg Ile Gly Asp Ile Ala Gly
145                 150                 155                 160

Glu His Thr Ser Phe Asp Lys Leu Pro Lys Gly Gly Ser Ala Thr Tyr
                165                 170                 175

Arg Gly Thr Ala Phe Gly Ser Asp Ala Gly Gly Lys Leu Thr Tyr
                180                 185                 190

Thr Ile Asp Phe Ala Val Lys Gln Gly His Gly Lys Ile Glu His Leu
                195                 200                 205

Lys Ser Pro Glu Leu Asn Val Asp Leu Ala Ala Ala Tyr Ile Lys Pro
210                 215                 220

Asp Lys Lys Arg His Ala Val Ile Ser Gly Ser Val Leu Tyr Asn Gln
225                 230                 235                 240

Asp Glu Lys Gly Ser Tyr Ser Leu Gly Ile Phe Gly Gly Gln Ala Gln
                245                 250                 255

Glu Val Ala Gly Ser Ala Glu Val Glu Thr Ala Asn Gly Ile His His
                260                 265                 270

Ile Gly Leu Ala Ala Lys Gln
                275

<210> SEQ ID NO 6
<211> LENGTH: 274
<212> TYPE: PRT
<213> ORGANISM: Neisseria meningitidis

<400> SEQUENCE: 6

Met Asn Arg Thr Ala Phe Cys Cys Leu Ser Leu Thr Ala Ala Leu Ile
1               5                   10                  15

Leu Thr Ala Cys Ser Ser Gly Gly Gly Gly Val Ala Ala Asp Ile Gly
                20                  25                  30

Ala Val Leu Ala Asp Ala Leu Thr Ala Pro Leu Asp His Lys Asp Lys
                35                  40                  45

Ser Leu Gln Ser Leu Thr Leu Asp Gln Ser Val Arg Lys Asn Glu Lys
50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
                100                 105                 110

Gly Glu Phe Gln Val Tyr Lys Gln Ser His Ser Ala Leu Thr Ala Leu
                115                 120                 125

Gln Thr Glu Gln Val Gln Asp Ser Glu His Ser Gly Lys Met Val Ala
                130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Ser Gly Lys Leu Thr Tyr Thr Ile Asp Phe Ala
                180                 185                 190

Ala Lys Gln Gly His Gly Lys Ile Glu His Leu Lys Ser Pro Glu Leu
                195                 200                 205

Asn Val Asp Leu Ala Ala Ser Asp Ile Lys Pro Asp Lys Lys Arg His
                210                 215                 220
```

```
Ala Val Ile Ser Gly Ser Val Leu Tyr Asn Gln Ala Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile Arg His Ile Gly Leu Ala Ala
            260                 265                 270

Lys Gln

<210> SEQ ID NO 7
<211> LENGTH: 274
<212> TYPE: PRT
<213> ORGANISM: Neisseria meningitidis

<400> SEQUENCE: 7

Met Asn Arg Thr Ala Phe Cys Cys Leu Ser Leu Thr Ala Ala Leu Ile
 1               5                  10                  15

Leu Thr Ala Cys Ser Ser Gly Gly Gly Val Ala Ala Asp Ile Gly
                20                  25                  30

Ala Gly Leu Ala Asp Ala Leu Thr Ala Pro Leu Asp His Lys Asp Lys
             35                  40                  45

Ser Leu Gln Ser Leu Thr Leu Asp Gln Ser Val Arg Lys Asn Glu Lys
         50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Val Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Ser Gly Lys Leu Thr Tyr Thr Ile Asp Phe Ala
            180                 185                 190

Ala Lys Gln Gly His Gly Lys Ile Glu His Leu Lys Ser Pro Glu Leu
        195                 200                 205

Asn Val Asp Leu Ala Ala Ser Asp Ile Lys Pro Asp Lys Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile Arg His Ile Gly Leu Ala Ala
            260                 265                 270

Lys Gln

<210> SEQ ID NO 8
<211> LENGTH: 274
<212> TYPE: PRT
<213> ORGANISM: Neisseria meningitidis

<400> SEQUENCE: 8
```

```
Met Asn Arg Thr Ala Phe Cys Cys Leu Ser Leu Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Met Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
                100                 105                 110

Gly Glu Phe Gln Val Tyr Lys Gln Ser His Ser Ala Leu Thr Ala Leu
            115                 120                 125

Gln Thr Glu Gln Val Gln Asp Ser Glu His Ser Gly Lys Met Val Ala
        130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Ile Tyr Thr Ile Asp Phe Ala
                180                 185                 190

Ala Lys Gln Gly His Gly Lys Ile Glu His Leu Lys Ser Pro Glu Leu
            195                 200                 205

Asn Val Asp Leu Ala Ala Ala Tyr Ile Lys Pro Asp Glu Lys His His
210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
            260                 265                 270

Lys Gln

<210> SEQ ID NO 9
<211> LENGTH: 274
<212> TYPE: PRT
<213> ORGANISM: Neisseria meningitidis

<400> SEQUENCE: 9

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Arg Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95
```

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Leu
            115                 120                 125

Gln Thr Glu Gln Glu Gln Asp Leu Glu His Ser Gly Lys Met Val Ala
            130                 135                 140

Lys Arg Arg Phe Arg Ile Gly Asp Ile Ala Gly Glu His Thr Ser Phe
145                 150                 155                 160

Asp Lys Leu Arg Glu Gly Gly Arg Ala Thr Tyr Arg Gly Thr Ala Phe
            165                 170                 175

Gly Ser Asp Asp Ala Gly Gly Lys Leu Thr Tyr Thr Ile Asp Phe Ala
            180                 185                 190

Ala Lys Gln Gly Tyr Gly Lys Ile Glu His Leu Lys Ser Pro Glu Leu
            195                 200                 205

Asn Val Asp Leu Ala Ala Ala Asp Ile Lys Pro Asp Glu Lys His His
            210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Glu Ala Gln Glu Val Ala Gly Ser
            245                 250                 255

Ala Glu Val Lys Thr Ala Asn Gly Ile His His Ile Gly Leu Ala Ala
            260                 265                 270

Lys Gln

<210> SEQ ID NO 10
<211> LENGTH: 273
<212> TYPE: PRT
<213> ORGANISM: Neisseria meningitidis

<400> SEQUENCE: 10

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly Ala
            20                  25                  30

Gly Leu Ala Asp Ala Leu Thr Ala Pro Leu Asp His Lys Asp Lys Ser
            35                  40                  45

Leu Gln Ser Leu Thr Leu Asp Gln Ser Val Arg Lys Asn Glu Lys Leu
        50                  55                  60

Lys Leu Ala Ala Gln Gly Ala Glu Lys Thr Tyr Gly Asn Gly Asp Ser
65                  70                  75                  80

Leu Asn Thr Gly Lys Leu Lys Asn Asp Lys Val Ser Arg Phe Asp Phe
            85                  90                  95

Ile Arg Gln Ile Glu Val Asp Gly Gln Leu Ile Thr Leu Glu Ser Gly
            100                 105                 110

Glu Phe Gln Ile Tyr Lys Gln Asp His Ser Ala Val Val Ala Leu Gln
            115                 120                 125

Ile Glu Lys Ile Asn Asn Pro Asp Lys Ile Asp Ser Leu Ile Asn Gln
            130                 135                 140

Arg Ser Phe Leu Val Ser Gly Leu Gly Glu His Thr Ala Phe Asn
145                 150                 155                 160

Gln Leu Pro Asp Gly Lys Ala Glu Tyr His Gly Lys Ala Phe Ser Ser
            165                 170                 175

Asp Asp Ala Gly Gly Lys Leu Thr Tyr Thr Ile Asp Phe Ala Ala
            180                 185                 190

```
Lys Gln Gly His Gly Lys Ile Glu His Leu Lys Thr Pro Glu Gln Asn
            195                 200                 205

Val Glu Leu Ala Ala Ala Glu Leu Lys Ala Asp Glu Lys Ser His Ala
        210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln
```

<210> SEQ ID NO 11
<211> LENGTH: 273
<212> TYPE: PRT
<213> ORGANISM: Neisseria meningitidis

<400> SEQUENCE: 11

```
Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
            35                  40                  45

Ser Leu Gln Ser Leu Thr Leu Asp Gln Ser Val Arg Lys Asn Glu Lys
        50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
130                 135                 140

Gln Arg Ser Phe Leu Val Ser Gly Leu Gly Gly Glu His Thr Ala Phe
145                 150                 155                 160

Asn Gln Leu Pro Ser Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
            195                 200                 205

Val Glu Leu Ala Ser Ala Glu Leu Lys Ala Asp Glu Lys Ser His Ala
        210                 215                 220

Val Ile Leu Gly Asp Thr Arg Tyr Gly Gly Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
            260                 265                 270

Gln
```

<210> SEQ ID NO 12
<211> LENGTH: 273
<212> TYPE: PRT
<213> ORGANISM: Neisseria meningitidis

<400> SEQUENCE: 12

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Ser Gly Lys Ala Glu Tyr His Gly Lys Ala Phe Ser
                165                 170                 175

Ser Asp Asp Pro Asn Gly Arg Leu His Tyr Ser Ile Asp Phe Thr Lys
            180                 185                 190

Lys Gln Gly Tyr Gly Arg Ile Glu His Leu Lys Thr Pro Glu Gln Asn
        195                 200                 205

Val Glu Leu Ala Ser Ala Glu Leu Lys Ala Asp Glu Lys Ser His Ala
    210                 215                 220

Val Ile Leu Gly Asp Thr Arg Tyr Gly Gly Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
            260                 265                 270

Gln

<210> SEQ ID NO 13
<211> LENGTH: 273
<212> TYPE: PRT
<213> ORGANISM: Neisseria meningitidis

<400> SEQUENCE: 13

Met Asn Arg Thr Ala Phe Cys Cys Leu Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys

```
            50                  55                  60
Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
130                 135                 140

Gln Arg Ser Phe Leu Val Ser Gly Leu Gly Gly Glu His Thr Ala Phe
145                 150                 155                 160

Asn Gln Leu Pro Ser Gly Lys Ala Glu Tyr His Gly Lys Ala Phe Ser
                165                 170                 175

Ser Asp Asp Pro Asn Gly Arg Leu His Tyr Ser Ile Asp Phe Thr Lys
            180                 185                 190

Lys Gln Gly Tyr Gly Arg Ile Glu His Leu Lys Thr Pro Glu Gln Asn
        195                 200                 205

Val Glu Leu Ala Ser Ala Glu Leu Lys Ala Asp Glu Lys Ser His Ala
210                 215                 220

Val Ile Leu Gly Asp Thr Arg Tyr Gly Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
            260                 265                 270

Gln

<210> SEQ ID NO 14
<211> LENGTH: 273
<212> TYPE: PRT
<213> ORGANISM: Neisseria meningitidis

<400> SEQUENCE: 14

Met Asn Arg Thr Ala Phe Cys Cys Leu Ser Leu Thr Ala Ala Leu Ile
  1               5                  10                  15

Leu Thr Ala Cys Ser Ser Gly Gly Gly Val Ala Ala Asp Ile Gly
                 20                  25                  30

Ala Gly Leu Ala Asp Ala Leu Thr Ala Pro Leu Asp His Lys Asp Lys
             35                  40                  45

Ser Leu Gln Ser Leu Thr Leu Asp Gln Ser Val Arg Lys Asn Glu Lys
         50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
130                 135                 140

Gln Arg Ser Phe Leu Val Ser Gly Leu Gly Gly Glu His Thr Ala Phe
```

```
            145                 150                 155                 160
Asn Gln Leu Pro Gly Gly Lys Ala Glu Tyr His Gly Lys Ala Phe Ser
                165                 170                 175
Ser Asp Asp Pro Asn Gly Arg Leu His Tyr Ser Ile Asp Phe Thr Lys
                180                 185                 190
Lys Gln Gly Tyr Gly Arg Ile Glu His Leu Lys Thr Pro Glu Gln Asn
                195                 200                 205
Val Glu Leu Ala Ser Ala Glu Leu Lys Ala Asp Glu Lys Ser His Ala
                210                 215                 220
Val Ile Leu Gly Asp Thr Arg Tyr Gly Ser Glu Lys Gly Thr Tyr
225                 230                 235                 240
His Leu Ala Leu Phe Gly Asp Arg Ala Gln Glu Ile Ala Gly Ser Ala
                245                 250                 255
Thr Val Lys Ile Arg Glu Lys Val His Glu Ile Gly Ile Ala Gly Lys
                260                 265                 270
Gln

<210> SEQ ID NO 15
<211> LENGTH: 273
<212> TYPE: PRT
<213> ORGANISM: Neisseria meningitidis

<400> SEQUENCE: 15

Met Asn Arg Thr Ala Phe Cys Cys Leu Ser Leu Thr Ala Ala Leu Ile
1               5                   10                  15
Leu Thr Ala Cys Ser Ser Gly Gly Gly Val Ala Ala Asp Ile Gly
                20                  25                  30
Ala Gly Leu Ala Asp Ala Leu Thr Thr Pro Leu Asp His Lys Asp Lys
                35                  40                  45
Ser Leu Gln Ser Leu Thr Leu Asp Gln Ser Val Arg Lys Asn Glu Lys
            50                  55                  60
Leu Lys Leu Ala Ala Gln Gly Ala Glu Lys Thr Tyr Gly Asn Gly Asp
65                  70                  75                  80
Ser Leu Asn Thr Gly Lys Leu Lys Asn Asp Lys Val Ser Arg Phe Asp
                85                  90                  95
Phe Ile Arg Gln Ile Glu Val Asp Gly Gln Thr Ile Thr Leu Ala Ser
                100                 105                 110
Gly Glu Phe Gln Ile Tyr Lys Gln Asn His Ser Ala Val Val Ala Leu
                115                 120                 125
Gln Ile Glu Lys Ile Asn Asn Pro Asp Lys Ile Asp Ser Leu Ile Asn
                130                 135                 140
Gln Arg Ser Phe Leu Val Ser Gly Leu Gly Gly Glu His Thr Ala Phe
145                 150                 155                 160
Asn Gln Leu Pro Asp Gly Lys Ala Glu Tyr His Gly Lys Ala Phe Ser
                165                 170                 175
Ser Asp Asp Pro Asn Gly Arg Leu His Tyr Ser Ile Asp Phe Thr Lys
                180                 185                 190
Lys Gln Gly Tyr Gly Arg Ile Glu His Leu Lys Thr Pro Glu Gln Asn
                195                 200                 205
Val Glu Leu Ala Ser Ala Glu Leu Lys Ala Asp Glu Lys Ser His Ala
                210                 215                 220
Val Ile Leu Gly Asp Thr Arg Tyr Gly Gly Glu Lys Gly Thr Tyr
225                 230                 235                 240
His Leu Ala Leu Phe Gly Asp Arg Ala Gln Glu Ile Ala Gly Ser Ala
```

```
            245                 250                 255
Thr Val Lys Ile Arg Glu Lys Val His Glu Ile Gly Ile Ala Gly Lys
                260                 265                 270
Gln

<210> SEQ ID NO 16
<211> LENGTH: 273
<212> TYPE: PRT
<213> ORGANISM: Neisseria meningitidis

<400> SEQUENCE: 16

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
                20                  25                  30

Ala Gly Leu Ala Asp Ala Leu Thr Ala Pro Leu Asp His Lys Asp Lys
            35                  40                  45

Ser Leu Gln Ser Leu Thr Leu Asp Gln Ser Val Arg Lys Asn Glu Lys
        50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Thr Ile Thr Leu Ala Ser
            100                 105                 110

Gly Glu Phe Gln Ile Tyr Lys Gln Asn His Ser Ala Val Val Ala Leu
        115                 120                 125

Gln Ile Glu Lys Ile Asn Asn Pro Asp Lys Ile Asp Ser Leu Ile Asn
130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Pro Asn Gly Arg Leu His Tyr Ser Ile Asp Phe Thr Lys
            180                 185                 190

Lys Gln Gly Tyr Gly Arg Ile Glu His Leu Lys Thr Pro Glu Gln Asn
        195                 200                 205

Val Glu Leu Ala Ser Ala Glu Leu Lys Ala Asp Glu Lys Ser His Ala
210                 215                 220

Val Ile Leu Gly Asp Thr Arg Tyr Gly Gly Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
            260                 265                 270

Gln

<210> SEQ ID NO 17
<211> LENGTH: 273
<212> TYPE: PRT
<213> ORGANISM: Neisseria meningitidis

<400> SEQUENCE: 17

Met Asn Arg Thr Ala Phe Cys Cys Leu Ser Leu Thr Thr Ala Leu Ile
1               5                   10                  15
```

```
Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Met Leu Asp Gln Ser Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Thr Ile Thr Leu Ala Ser
            100                 105                 110

Gly Glu Phe Gln Ile Tyr Lys Gln Asn His Ser Ala Val Val Ala Leu
        115                 120                 125

Gln Ile Glu Lys Ile Asn Asn Pro Asp Lys Ile Asp Ser Leu Ile Asn
130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Pro Asn Gly Arg Leu His Tyr Ser Ile Asp Phe Thr Lys
            180                 185                 190

Lys Gln Gly Tyr Gly Arg Ile Glu His Leu Lys Thr Pro Glu Gln Asn
        195                 200                 205

Val Glu Leu Ala Ser Ala Glu Leu Lys Ala Asp Glu Lys Ser His Ala
210                 215                 220

Val Ile Leu Gly Asp Thr Arg Tyr Gly Gly Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
            260                 265                 270

Gln

<210> SEQ ID NO 18
<211> LENGTH: 281
<212> TYPE: PRT
<213> ORGANISM: Neisseria meningitidis

<400> SEQUENCE: 18

Met Asn Arg Thr Ala Phe Cys Cys Leu Ser Leu Thr Thr Ala Leu Ile
 1               5                  10                  15

Leu Thr Ala Cys Ser Ser Gly Gly Gly Ser Gly Gly Gly Val
            20                  25                  30

Ala Ala Asp Ile Gly Thr Gly Leu Ala Asp Ala Leu Thr Ala Pro Leu
        35                  40                  45

Asp His Lys Asp Lys Gly Leu Lys Ser Leu Thr Leu Glu Asp Ser Ile
 50                  55                  60

Pro Gln Asn Gly Thr Leu Thr Leu Ser Ala Gln Gly Ala Glu Lys Thr
 65                  70                  75                  80

Phe Lys Ala Gly Asp Lys Asp Asn Ser Leu Asn Thr Gly Lys Leu Lys
                85                  90                  95

Asn Asp Lys Ile Ser Arg Phe Asp Phe Val Gln Lys Ile Glu Val Asp
            100                 105                 110
```

```
Gly Gln Thr Ile Thr Leu Ala Ser Gly Glu Phe Gln Ile Tyr Lys Gln
            115                 120                 125

Asn His Ser Ala Val Val Ala Leu Gln Ile Glu Lys Ile Asn Asn Pro
        130                 135                 140

Asp Lys Thr Asp Ser Leu Ile Asn Gln Arg Ser Phe Leu Val Ser Gly
145                 150                 155                 160

Leu Gly Gly Glu His Thr Ala Phe Asn Gln Leu Pro Gly Gly Lys Ala
                165                 170                 175

Glu Tyr His Gly Lys Ala Phe Ser Ser Asp Pro Asn Gly Arg Leu
            180                 185                 190

His Tyr Ser Ile Asp Phe Thr Lys Lys Gln Gly Tyr Gly Arg Ile Glu
        195                 200                 205

His Leu Lys Thr Leu Glu Gln Asn Val Glu Leu Ala Ala Ala Glu Leu
    210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255

Ala Gln Glu Ile Ala Gly Ser Ala Thr Val Lys Ile Gly Glu Lys Val
            260                 265                 270

His Glu Ile Gly Ile Ala Gly Lys Gln
            275                 280

<210> SEQ ID NO 19
<211> LENGTH: 281
<212> TYPE: PRT
<213> ORGANISM: Neisseria meningitidis

<400> SEQUENCE: 19

Met Asn Arg Thr Ala Phe Cys Cys Leu Phe Leu Thr Thr Ala Leu Ile
1               5                   10                  15

Leu Thr Ala Cys Ser Ser Gly Gly Gly Ser Gly Gly Gly Gly Gly Val
            20                  25                  30

Ala Ala Asp Ile Gly Thr Gly Leu Ala Asp Ala Leu Thr Ala Pro Leu
        35                  40                  45

Asp His Lys Asp Lys Gly Leu Lys Ser Leu Thr Leu Glu Asp Ser Ile
50                  55                  60

Pro Gln Asn Gly Thr Leu Thr Leu Ser Ala Gln Gly Ala Glu Lys Thr
65                  70                  75                  80

Phe Lys Ala Gly Asp Lys Asp Asn Ser Leu Asn Thr Gly Lys Leu Lys
                85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
        115                 120                 125

Asp His Ser Ala Val Val Ala Leu Gln Ile Glu Lys Ile Asn Asn Pro
    130                 135                 140

Asp Lys Ile Asp Ser Leu Ile Asn Gln Arg Ser Phe Leu Val Ser Gly
145                 150                 155                 160

Leu Gly Gly Glu His Thr Ala Phe Asn Gln Leu Pro Gly Gly Lys Ala
                165                 170                 175

Glu Tyr His Gly Lys Ala Phe Ser Ser Asp Ala Gly Gly Lys Leu
            180                 185                 190

Thr Tyr Thr Ile Asp Phe Ala Ala Lys Gln Gly His Gly Lys Ile Glu
        195                 200                 205
```

```
His Leu Lys Thr Pro Glu Gln Asn Val Glu Leu Ala Ala Ala Glu Leu
    210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255

Ala Gln Glu Ile Ala Gly Ser Ala Thr Val Lys Ile Gly Glu Lys Val
            260                 265                 270

His Glu Ile Ser Ile Ala Gly Lys Gln
            275                 280

<210> SEQ ID NO 20
<211> LENGTH: 281
<212> TYPE: PRT
<213> ORGANISM: Neisseria meningitidis

<400> SEQUENCE: 20

Met Asn Arg Thr Ala Phe Cys Cys Leu Phe Leu Thr Thr Ala Leu Ile
1               5                   10                  15

Leu Thr Ala Cys Ser Ser Gly Gly Gly Ser Gly Ser Gly Gly Val
            20                  25                  30

Ala Ala Asp Ile Gly Thr Gly Leu Ala Asp Ala Leu Thr Thr Pro Leu
            35                  40                  45

Asp His Lys Asp Lys Gly Leu Lys Ser Leu Thr Leu Glu Asp Ser Ile
        50                  55                  60

Pro Gln Asn Gly Thr Leu Thr Leu Ser Ala Gln Gly Ala Glu Lys Thr
65                  70                  75                  80

Phe Lys Ala Gly Asp Lys Asp Asn Ser Leu Asn Thr Gly Lys Leu Lys
                85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
            115                 120                 125

Asp His Ser Ala Val Val Ala Leu Gln Ile Glu Lys Ile Asn Asn Pro
        130                 135                 140

Asp Lys Ile Asp Ser Leu Ile Asn Gln Arg Ser Phe Leu Val Ser Gly
145                 150                 155                 160

Leu Gly Gly Glu His Thr Ala Phe Asn Gln Leu Pro Gly Gly Lys Ala
                165                 170                 175

Glu Tyr His Gly Lys Ala Phe Ser Ser Asp Ala Gly Gly Lys Leu
            180                 185                 190

Thr Tyr Thr Ile Asp Phe Ala Ala Lys Gln Gly His Gly Lys Ile Glu
            195                 200                 205

His Leu Lys Thr Pro Glu Gln Asn Val Glu Leu Ala Ala Ala Glu Leu
    210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255

Ala Gln Glu Ile Ala Gly Ser Ala Thr Val Lys Ile Gly Glu Lys Val
            260                 265                 270

His Glu Ile Gly Ile Ala Gly Lys Gln
            275                 280
```

```
<210> SEQ ID NO 21
<211> LENGTH: 279
<212> TYPE: PRT
<213> ORGANISM: Neisseria meningitidis

<400> SEQUENCE: 21

Met Asn Arg Thr Ala Phe Cys Cys Leu Phe Leu Thr Thr Ala Leu Ile
1               5                   10                  15

Leu Thr Ala Cys Ser Ser Gly Gly Gly Ser Gly Gly Ile Ala Ala
            20                  25                  30

Asp Ile Gly Thr Gly Leu Ala Asp Ala Leu Thr Ala Pro Leu Asp His
        35                  40                  45

Lys Asp Lys Gly Leu Lys Ser Leu Thr Leu Glu Asp Ser Ile Pro Gln
    50                  55                  60

Asn Gly Thr Leu Thr Leu Ser Ala Gln Gly Ala Glu Lys Thr Phe Lys
65                  70                  75                  80

Ala Gly Asp Lys Asp Asn Ser Leu Asn Thr Gly Lys Leu Lys Asn Asp
                85                  90                  95

Lys Ile Ser Arg Phe Asp Phe Val Gln Lys Ile Glu Val Asp Gly Gln
            100                 105                 110

Thr Ile Thr Leu Ala Ser Gly Glu Phe Gln Ile Tyr Lys Gln Asp His
        115                 120                 125

Ser Ala Val Val Ala Leu Gln Ile Glu Lys Ile Asn Asn Pro Asp Lys
    130                 135                 140

Ile Asp Ser Leu Ile Asn Gln Arg Ser Phe Leu Val Ser Gly Leu Gly
145                 150                 155                 160

Gly Glu His Thr Ala Phe Asn Gln Leu Pro Gly Gly Lys Ala Glu Tyr
                165                 170                 175

His Gly Lys Ala Phe Ser Ser Asp Asp Ala Gly Gly Lys Leu Thr Tyr
            180                 185                 190

Thr Ile Asp Phe Ala Ala Lys Gln Gly His Gly Lys Ile Glu His Leu
        195                 200                 205

Lys Thr Pro Glu Gln Asn Val Glu Leu Ala Ala Ala Glu Leu Lys Ala
    210                 215                 220

Asp Glu Lys Ser His Ala Val Ile Leu Gly Asp Thr Arg Tyr Gly Ser
225                 230                 235                 240

Glu Glu Lys Gly Thr Tyr His Leu Ala Leu Phe Gly Asp Arg Ala Gln
                245                 250                 255

Glu Ile Ala Gly Ser Ala Thr Val Lys Ile Gly Glu Lys Val His Glu
            260                 265                 270

Ile Gly Ile Ala Gly Lys Gln
        275

<210> SEQ ID NO 22
<211> LENGTH: 281
<212> TYPE: PRT
<213> ORGANISM: Neisseria meningitidis

<400> SEQUENCE: 22

Met Asn Arg Thr Thr Phe Cys Cys Leu Ser Leu Thr Thr Ala Leu Ile
1               5                   10                  15

Leu Thr Ala Cys Ser Ser Gly Gly Gly Gly Ser Gly Gly Gly Gly Val
            20                  25                  30

Ala Ala Asp Ile Gly Ala Gly Leu Ala Asp Ala Leu Thr Ala Pro Leu
        35                  40                  45

Asp His Lys Asp Lys Gly Leu Lys Ser Leu Thr Leu Glu Asp Ser Ile
```

```
                 50                  55                  60
Pro Gln Asn Gly Thr Leu Thr Leu Ser Ala Gln Gly Ala Glu Lys Thr
 65                  70                  75                  80

Phe Lys Ala Gly Gly Lys Asp Asn Ser Leu Asn Thr Gly Lys Leu Lys
                     85                  90                  95

Asn Asp Lys Ile Ser Arg Phe Asp Phe Val Gln Lys Ile Glu Val Asp
                    100                 105                 110

Gly Gln Thr Ile Thr Leu Ala Ser Gly Glu Phe Gln Ile Tyr Lys Gln
                115                 120                 125

Asp His Ser Ala Val Ala Leu Gln Ile Glu Lys Ile Asn Asn Pro
                130                 135                 140

Asp Lys Thr Asp Ser Leu Ile Asn Gln Arg Ser Phe Leu Val Ser Gly
145                 150                 155                 160

Leu Gly Gly Glu His Thr Ala Phe Asn Gln Leu Pro Gly Gly Lys Ala
                165                 170                 175

Glu Tyr His Gly Lys Ala Phe Ser Ser Asp Pro Asn Gly Arg Leu
                180                 185                 190

His Tyr Thr Ile Asp Phe Thr Asn Lys Gln Gly Tyr Gly Arg Ile Glu
                195                 200                 205

His Leu Lys Thr Pro Glu Gln Asn Val Glu Leu Ala Ser Ala Glu Leu
210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255

Ala Gln Glu Ile Ala Gly Ser Ala Thr Val Lys Ile Gly Glu Lys Val
                260                 265                 270

His Glu Ile Gly Ile Ala Gly Lys Gln
                275                 280

<210> SEQ ID NO 23
<211> LENGTH: 279
<212> TYPE: PRT
<213> ORGANISM: Neisseria meningitidis

<400> SEQUENCE: 23

Met Asn Arg Thr Thr Phe Cys Cys Leu Ser Leu Thr Ala Gly Pro Asp
 1               5                  10                  15

Ser Asp Arg Leu Gln Gln Arg Arg Gly Gly Gly Gly Val Ala Ala
                 20                  25                  30

Asp Ile Gly Thr Gly Leu Ala Asp Ala Leu Thr Ala Pro Leu Asp His
                 35                  40                  45

Lys Asp Lys Gly Leu Lys Ser Leu Thr Leu Glu Ala Ser Ile Pro Gln
 50                  55                  60

Asn Gly Thr Leu Thr Leu Ser Ala Gln Gly Ala Glu Lys Thr Phe Lys
 65                  70                  75                  80

Ala Gly Gly Lys Asp Asn Ser Leu Asn Thr Gly Lys Leu Lys Asn Asp
                 85                  90                  95

Lys Ile Ser Arg Phe Asp Phe Val Gln Lys Ile Glu Val Asp Gly Gln
                100                 105                 110

Thr Ile Thr Leu Ala Ser Gly Glu Phe Gln Ile Tyr Lys Gln Asp His
                115                 120                 125

Ser Ala Val Val Ala Leu Arg Ile Glu Lys Ile Asn Asn Pro Asp Lys
                130                 135                 140
```

Ile Asp Ser Leu Ile Asn Gln Arg Ser Phe Leu Val Ser Asp Leu Gly
145                 150                 155                 160

Gly Glu His Thr Ala Phe Asn Gln Leu Pro Asp Gly Lys Ala Glu Tyr
                165                 170                 175

His Gly Lys Ala Phe Ser Ser Asp Ala Asp Gly Lys Leu Thr Tyr
            180                 185                 190

Thr Ile Asp Phe Ala Ala Lys Gln Gly His Gly Lys Ile Glu His Leu
        195                 200                 205

Lys Thr Pro Glu Gln Asn Val Glu Leu Ala Ser Ala Glu Leu Lys Ala
    210                 215                 220

Asp Glu Lys Ser His Ala Val Ile Leu Gly Asp Thr Arg Tyr Gly Gly
225                 230                 235                 240

Glu Glu Lys Gly Thr Tyr Arg Leu Ala Leu Phe Gly Asp Arg Ala Gln
                245                 250                 255

Glu Ile Ala Gly Ser Ala Thr Val Lys Ile Gly Glu Lys Val His Glu
                260                 265                 270

Ile Gly Ile Ala Asp Lys Gln
        275

<210> SEQ ID NO 24
<211> LENGTH: 255
<212> TYPE: PRT
<213> ORGANISM: Neisseria meningitidis

<400> SEQUENCE: 24

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 25
<211> LENGTH: 255
<212> TYPE: PRT
<213> ORGANISM: Neisseria meningitidis

<400> SEQUENCE: 25

Cys Ser Ser Gly Gly Gly Val Ala Ala Asp Ile Gly Ala Gly Leu
  1               5                  10                  15

Ala Asp Ala Leu Thr Ala Pro Leu Asp His Lys Asp Lys Gly Leu Gln
                 20                  25                  30

Ser Leu Met Leu Asp Gln Ser Val Arg Lys Asn Glu Lys Leu Lys Leu
                 35                  40                  45

Ala Ala Gln Gly Ala Glu Lys Thr Tyr Gly Asn Gly Asp Ser Leu Asn
         50                  55                  60

Thr Gly Lys Leu Lys Asn Asp Lys Val Ser Arg Phe Asp Phe Ile Arg
 65                  70                  75                  80

Gln Ile Glu Val Asp Gly Lys Leu Ile Thr Leu Glu Ser Gly Glu Phe
                 85                  90                  95

Gln Val Tyr Lys Gln Ser His Ser Ala Leu Thr Ala Leu Gln Thr Glu
                100                 105                 110

Gln Val Gln Asp Ser Glu Asp Ser Gly Lys Met Val Ala Lys Arg Gln
                115                 120                 125

Phe Arg Ile Gly Asp Ile Ala Gly Glu His Thr Ser Phe Asp Lys Leu
130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
                180                 185                 190

Leu Ala Thr Ala Tyr Ile Lys Pro Asp Glu Lys His His Ala Val Ile
                195                 200                 205

Ser Gly Ser Val Leu Tyr Asn Gln Asp Glu Lys Gly Ser Tyr Ser Leu
                210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255

<210> SEQ ID NO 26
<211> LENGTH: 255
<212> TYPE: PRT
<213> ORGANISM: Neisseria meningitidis

<400> SEQUENCE: 26

Cys Ser Ser Gly Gly Gly Val Ala Ala Asp Ile Gly Ala Gly Leu
  1               5                  10                  15

Ala Asp Ala Leu Thr Ala Pro Leu Asp His Lys Asp Lys Ser Leu Gln
                 20                  25                  30

Ser Leu Thr Leu Asp Gln Ser Val Arg Lys Asn Glu Lys Leu Lys Leu
                 35                  40                  45

Ala Ala Gln Gly Ala Glu Lys Thr Tyr Gly Asn Gly Asp Ser Leu Asn
         50                  55                  60

```
Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
             85                   90                  95

Gln Val Tyr Lys Gln Ser His Ser Ala Leu Thr Ala Leu Gln Thr Glu
            100                 105                 110

Gln Val Gln Asp Ser Glu Asp Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys Arg His Ala Val Ile
        195                 200                 205

Ser Gly Ser Val Leu Tyr Asn Gln Asp Glu Lys Gly Ser Tyr Ser Leu
210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255

<210> SEQ ID NO 27
<211> LENGTH: 255
<212> TYPE: PRT
<213> ORGANISM: Neisseria meningitidis

<400> SEQUENCE: 27

Cys Ser Ser Gly Gly Gly Gly Val Ala Ala Asp Ile Gly Ala Gly Leu
  1               5                  10                  15

Ala Asp Ala Leu Thr Ala Pro Leu Asp His Lys Asp Lys Ser Leu Gln
             20                  25                  30

Ser Leu Thr Leu Asp Gln Ser Val Arg Lys Asn Glu Lys Leu Lys Leu
         35                  40                  45

Ala Ala Gln Gly Ala Glu Lys Thr Tyr Gly Asn Gly Asp Ser Leu Asn
     50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
             85                   90                  95

Gln Val Tyr Lys Gln Ser His Ser Ala Leu Thr Ala Leu Gln Thr Glu
            100                 105                 110

Gln Glu Gln Asp Pro Glu His Ser Gly Lys Met Val Ala Lys Arg Arg
        115                 120                 125

Phe Lys Ile Gly Asp Ile Ala Gly Glu His Thr Ser Phe Asp Lys Leu
    130                 135                 140

Pro Lys Asp Val Met Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
```

```
                    180                 185                 190
Leu Ala Thr Ala Tyr Ile Lys Pro Asp Glu Lys His His Ala Val Ile
                195                 200                 205

Ser Gly Ser Val Leu Tyr Asn Gln Asp Glu Lys Gly Ser Tyr Ser Leu
            210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255

<210> SEQ ID NO 28
<211> LENGTH: 260
<212> TYPE: PRT
<213> ORGANISM: Neisseria meningitidis

<400> SEQUENCE: 28

Cys Ser Ser Gly Gly Gly Ser Gly Gly Gly Val Ala Ala Asp
1               5                   10                  15

Ile Gly Ala Gly Leu Ala Asp Ala Leu Thr Ala Pro Leu Asp His Lys
                20                  25                  30

Asp Lys Gly Leu Gln Ser Leu Thr Leu Asp Gln Ser Val Arg Lys Asn
            35                  40                  45

Glu Lys Leu Lys Leu Ala Ala Gln Gly Ala Glu Lys Thr Tyr Gly Asn
50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Val Tyr Lys Gln Ser His Ser Ala Leu Thr
            100                 105                 110

Ala Leu Gln Thr Glu Gln Val Gln Asp Ser Glu Asp Ser Gly Lys Met
        115                 120                 125

Val Ala Lys Arg Gln Phe Arg Ile Gly Asp Ile Ala Gly Glu His Thr
130                 135                 140

Ser Phe Asp Lys Leu Pro Lys Gly Gly Ser Ala Thr Tyr Arg Gly Thr
145                 150                 155                 160

Ala Phe Gly Ser Asp Asp Ala Gly Gly Lys Leu Thr Tyr Thr Ile Asp
                165                 170                 175

Phe Ala Val Lys Gln Gly His Gly Lys Ile Glu His Leu Lys Ser Pro
            180                 185                 190

Glu Leu Asn Val Asp Leu Ala Ala Ala Tyr Ile Lys Pro Asp Lys Lys
        195                 200                 205

Arg His Ala Val Ile Ser Gly Ser Val Leu Tyr Asn Gln Asp Glu Lys
210                 215                 220

Gly Ser Tyr Ser Leu Gly Ile Phe Gly Gly Gln Ala Gln Glu Val Ala
225                 230                 235                 240

Gly Ser Ala Glu Val Glu Thr Ala Asn Gly Ile His His Ile Gly Leu
                245                 250                 255

Ala Ala Lys Gln
            260

<210> SEQ ID NO 29
<211> LENGTH: 255
<212> TYPE: PRT
<213> ORGANISM: Neisseria meningitidis
```

<400> SEQUENCE: 29

```
Cys Ser Ser Gly Gly Gly Val Ala Ala Asp Ile Gly Ala Val Leu
  1               5                  10                  15

Ala Asp Ala Leu Thr Ala Pro Leu Asp His Lys Asp Lys Ser Leu Gln
             20                  25                  30

Ser Leu Thr Leu Asp Gln Ser Val Arg Lys Asn Glu Lys Leu Lys Leu
         35                  40                  45

Ala Ala Gln Gly Ala Glu Lys Thr Tyr Gly Asn Gly Asp Ser Leu Asn
     50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
                245                 250                 255
```

<210> SEQ ID NO 30
<211> LENGTH: 255
<212> TYPE: PRT
<213> ORGANISM: Neisseria meningitidis

<400> SEQUENCE: 30

```
Cys Ser Ser Gly Gly Gly Val Ala Ala Asp Ile Gly Ala Gly Leu
  1               5                  10                  15

Ala Asp Ala Leu Thr Ala Pro Leu Asp His Lys Asp Lys Ser Leu Gln
             20                  25                  30

Ser Leu Thr Leu Asp Gln Ser Val Arg Lys Asn Glu Lys Leu Lys Leu
         35                  40                  45

Ala Ala Gln Gly Ala Glu Lys Thr Tyr Gly Asn Gly Asp Ser Leu Asn
     50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Val Tyr Lys Gln Ser His Ser Ala Leu Thr Ala Leu Gln Thr Glu
            100                 105                 110
```

-continued

```
Gln Val Gln Asp Ser Glu His Ser Gly Lys Met Val Ala Lys Arg Gln
            115                 120                 125

Phe Arg Ile Gly Asp Ile Ala Gly Glu His Thr Ser Phe Asp Lys Leu
        130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
                245                 250                 255
```

<210> SEQ ID NO 31
<211> LENGTH: 255
<212> TYPE: PRT
<213> ORGANISM: Neisseria meningitidis

<400> SEQUENCE: 31

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Met Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Ile Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ala Tyr Ile Lys Pro Asp Glu Lys His His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240
```

Lys Thr Val Asn Gly Ile Arg His Ile Gly Leu Ala Ala Lys Gln
            245                 250                 255

<210> SEQ ID NO 32
<211> LENGTH: 255
<212> TYPE: PRT
<213> ORGANISM: Neisseria meningitidis

<400> SEQUENCE: 32

Cys Ser Ser Gly Gly Gly Val Ala Ala Asp Ile Gly Ala Gly Leu
 1               5                  10                  15

Ala Asp Ala Leu Thr Ala Pro Leu Asp His Lys Asp Lys Gly Leu Arg
             20                  25                  30

Ser Leu Thr Leu Asp Gln Ser Val Arg Lys Asn Glu Lys Leu Lys Leu
             35                  40                  45

Ala Ala Gln Gly Ala Glu Lys Thr Tyr Gly Asn Gly Asp Ser Leu Asn
         50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Val Tyr Lys Gln Ser His Ser Ala Leu Thr Ala Leu Gln Thr Glu
            100                 105                 110

Gln Glu Gln Asp Leu Glu His Ser Gly Lys Met Val Ala Lys Arg Arg
            115                 120                 125

Phe Arg Ile Gly Asp Ile Ala Gly Glu His Thr Ser Phe Asp Lys Leu
130                 135                 140

Arg Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Tyr Gly Lys Ile Glu His Leu Lys Ser Pro Glu Leu Asn Val Asp
            180                 185                 190

Leu Ala Ala Ala Asp Ile Lys Pro Asp Glu Lys His His Ala Val Ile
        195                 200                 205

Ser Gly Ser Val Leu Tyr Asn Gln Asp Glu Lys Gly Ser Tyr Ser Leu
210                 215                 220

Gly Ile Phe Gly Gly Glu Ala Gln Glu Val Ala Gly Ser Ala Glu Val
225                 230                 235                 240

Lys Thr Ala Asn Gly Ile His His Ile Gly Leu Ala Ala Lys Gln
            245                 250                 255

<210> SEQ ID NO 33
<211> LENGTH: 254
<212> TYPE: PRT
<213> ORGANISM: Neisseria meningitidis

<400> SEQUENCE: 33

Cys Ser Ser Gly Gly Gly Val Ala Ala Asp Ile Gly Ala Gly Leu
 1               5                  10                  15

Ala Asp Ala Leu Thr Ala Pro Leu Asp His Lys Asp Lys Ser Leu Gln
             20                  25                  30

Ser Leu Thr Leu Asp Gln Ser Val Arg Lys Asn Glu Lys Leu Lys Leu
             35                  40                  45

Ala Ala Gln Gly Ala Glu Lys Thr Tyr Gly Asn Gly Asp Ser Leu Asn
         50                  55                  60

```
Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250

<210> SEQ ID NO 34
<211> LENGTH: 254
<212> TYPE: PRT
<213> ORGANISM: Neisseria meningitidis

<400> SEQUENCE: 34

Cys Ser Ser Gly Gly Gly Gly Val Ala Ala Asp Ile Gly Ala Gly Leu
  1               5                  10                  15

Ala Asp Ala Leu Thr Ala Pro Leu Asp His Lys Asp Lys Ser Leu Gln
                 20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
```

```
                180                 185                 190
Ala Ser Ala Glu Leu Lys Ala Asp Glu Lys Ser His Ala Val Ile Leu
        195                 200                 205

Gly Asp Thr Arg Tyr Gly Gly Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 35
<211> LENGTH: 254
<212> TYPE: PRT
<213> ORGANISM: Neisseria meningitidis

<400> SEQUENCE: 35

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 36
<211> LENGTH: 254
<212> TYPE: PRT
<213> ORGANISM: Neisseria meningitidis

<400> SEQUENCE: 36

Cys Ser Ser Gly Gly Gly Gly Val Ala Ala Asp Ile Gly Ala Gly Leu
```

```
               1               5                  10                 15
            Ala Asp Ala Leu Thr Ala Pro Leu Asp His Lys Asp Lys Ser Leu Gln
                         20                  25                 30

Ser Leu Thr Leu Asp Gln Ser Val Arg Lys Asn Glu Lys Leu Lys Leu
                         35                  40                 45

Ala Ala Gln Gly Ala Glu Lys Thr Tyr Gly Asn Gly Asp Ser Leu Asn
                         50                  55                 60

Thr Gly Lys Leu Lys Asn Asp Lys Val Ser Arg Phe Asp Phe Ile Arg
             65                  70                  75                 80

Gln Ile Glu Val Asp Gly Gln Leu Ile Thr Leu Glu Ser Gly Glu Phe
                             85                  90                 95

Gln Ile Tyr Lys Gln Asp His Ser Ala Val Val Ala Leu Gln Ile Glu
                        100                 105                110

Lys Ile Asn Asn Pro Asp Lys Ile Asp Ser Leu Ile Asn Gln Arg Ser
                        115                 120                125

Phe Leu Val Ser Gly Leu Gly Gly Glu His Thr Ala Phe Asn Gln Leu
                        130                 135                140

Pro Ser Gly Lys Ala Glu Tyr His Gly Lys Ala Phe Ser Ser Asp Asp
            145                 150                 155                160

Pro Asn Gly Arg Leu His Tyr Ser Ile Asp Phe Thr Lys Lys Gln Gly
                        165                 170                175

Tyr Gly Arg Ile Glu His Leu Lys Thr Pro Glu Gln Asn Val Glu Leu
                        180                 185                190

Ala Ser Ala Glu Leu Lys Ala Asp Glu Lys Ser His Ala Val Ile Leu
                        195                 200                205

Gly Asp Thr Arg Tyr Gly Gly Glu Glu Lys Gly Thr Tyr His Leu Ala
                        210                 215                220

Leu Phe Gly Asp Arg Ala Gln Glu Ile Ala Gly Ser Ala Thr Val Lys
            225                 230                 235                240

Ile Arg Glu Lys Val His Glu Ile Gly Ile Ala Gly Lys Gln
                            245                 250
```

<210> SEQ ID NO 37
<211> LENGTH: 254
<212> TYPE: PRT
<213> ORGANISM: Neisseria meningitidis

<400> SEQUENCE: 37

```
            Cys Ser Ser Gly Gly Gly Gly Val Ala Ala Asp Ile Gly Ala Gly Leu
             1               5                  10                 15

Ala Asp Ala Leu Thr Ala Pro Leu Asp His Lys Asp Lys Ser Leu Gln
                         20                  25                 30

Ser Leu Thr Leu Asp Gln Ser Val Arg Lys Asn Glu Lys Leu Lys Leu
                         35                  40                 45

Ala Ala Gln Gly Ala Glu Lys Thr Tyr Gly Asn Gly Asp Ser Leu Asn
                         50                  55                 60

Thr Gly Lys Leu Lys Asn Asp Lys Val Ser Arg Phe Asp Phe Ile Arg
             65                  70                  75                 80

Gln Ile Glu Val Asp Gly Gln Leu Ile Thr Leu Glu Ser Gly Glu Phe
                             85                  90                 95

Gln Ile Tyr Lys Gln Asp His Ser Ala Val Val Ala Leu Gln Ile Glu
                        100                 105                110

Lys Ile Asn Asn Pro Asp Lys Ile Asp Ser Leu Ile Asn Gln Arg Ser
                        115                 120                125
```

```
Phe Leu Val Ser Gly Leu Gly Gly Glu His Thr Ala Phe Asn Gln Leu
130                 135                 140

Pro Gly Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
                180                 185                 190

Ala Ser Ala Glu Leu Lys Ala Asp Glu Lys Ser His Ala Val Ile Leu
                195                 200                 205

Gly Asp Thr Arg Tyr Gly Ser Glu Glu Lys Gly Thr Tyr His Leu Ala
210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 38
<211> LENGTH: 254
<212> TYPE: PRT
<213> ORGANISM: Neisseria meningitidis

<400> SEQUENCE: 38

```
Cys Ser Ser Gly Gly Gly Val Ala Ala Asp Ile Gly Ala Gly Leu
1                   5                   10                  15

Ala Asp Ala Leu Thr Thr Pro Leu Asp His Lys Asp Lys Ser Leu Gln
                20                  25                  30

Ser Leu Thr Leu Asp Gln Ser Val Arg Lys Asn Glu Lys Leu Lys Leu
                35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Thr Ile Thr Leu Ala Ser Gly Glu Phe
                85                  90                  95

Gln Ile Tyr Lys Gln Asn His Ser Ala Val Val Ala Leu Gln Ile Glu
                100                 105                 110

Lys Ile Asn Asn Pro Asp Lys Ile Asp Ser Leu Ile Asn Gln Arg Ser
                115                 120                 125

Phe Leu Val Ser Gly Leu Gly Gly Glu His Thr Ala Phe Asn Gln Leu
130                 135                 140

Pro Asp Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
                180                 185                 190

Ala Ser Ala Glu Leu Lys Ala Asp Glu Lys Ser His Ala Val Ile Leu
                195                 200                 205

Gly Asp Thr Arg Tyr Gly Ser Glu Glu Lys Gly Thr Tyr His Leu Ala
210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 39
<211> LENGTH: 254
<212> TYPE: PRT
<213> ORGANISM: Neisseria meningitidis

<400> SEQUENCE: 39

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Thr Ile Thr Leu Ala Ser Gly Glu Phe
                85                  90                  95

Gln Ile Tyr Lys Gln Asn His Ser Ala Val Val Ala Leu Gln Ile Glu
                100                 105                 110

Lys Ile Asn Asn Pro Asp Lys Ile Asp Ser Leu Ile Asn Gln Arg Ser
            115                 120                 125

Phe Leu Val Ser Gly Leu Gly Gly Glu His Thr Ala Phe Asn Gln Leu
        130                 135                 140

Pro Asp Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
                180                 185                 190

Ala Ser Ala Glu Leu Lys Ala Asp Glu Lys Ser His Ala Val Ile Leu
            195                 200                 205

Gly Asp Thr Arg Tyr Gly Gly Glu Glu Lys Gly Thr Tyr His Leu Ala
        210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 40
<211> LENGTH: 254
<212> TYPE: PRT
<213> ORGANISM: Neisseria meningitidis

<400> SEQUENCE: 40

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
                20                  25                  30

Ser Leu Met Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

```
Gln Ile Glu Val Asp Gly Gln Thr Ile Thr Leu Ala Ser Gly Glu Phe
                85                  90                  95

Gln Ile Tyr Lys Gln Asn His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 41
<211> LENGTH: 262
<212> TYPE: PRT
<213> ORGANISM: Neisseria meningitidis

<400> SEQUENCE: 41

Cys Ser Ser Gly Gly Gly Gly Ser Gly Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asn His Ser
            100                 105                 110

Ala Val Val Ala Leu Gln Ile Glu Lys Ile Asn Asn Pro Asp Lys Thr
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Arg Ile Glu His Leu Lys
            180                 185                 190

Thr Leu Glu Gln Asn Val Glu Leu Ala Ala Ala Glu Leu Lys Ala Asp
```

```
                195                 200                 205
Glu Lys Ser His Ala Val Ile Leu Gly Asp Thr Arg Tyr Gly Ser Glu
    210                 215                 220
Glu Lys Gly Thr Tyr His Leu Ala Leu Phe Gly Asp Arg Ala Gln Glu
225                 230                 235                 240
Ile Ala Gly Ser Ala Thr Val Lys Ile Gly Glu Lys Val His Glu Ile
                245                 250                 255
Gly Ile Ala Gly Lys Gln
            260

<210> SEQ ID NO 42
<211> LENGTH: 262
<212> TYPE: PRT
<213> ORGANISM: Neisseria meningitidis

<400> SEQUENCE: 42

Cys Ser Ser Gly Gly Gly Ser Gly Gly Gly Val Ala Ala Asp
1               5                   10                  15

Ile Gly Thr Gly Leu Ala Asp Ala Leu Thr Ala Pro Leu Asp His Lys
                20                  25                  30

Asp Lys Gly Leu Lys Ser Leu Thr Leu Glu Asp Ser Ile Pro Gln Asn
            35                  40                  45

Gly Thr Leu Thr Leu Ser Ala Gln Gly Ala Glu Lys Thr Phe Lys Ala
        50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asp His Ser
            100                 105                 110

Ala Val Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Ala Gly Gly Lys Leu Thr Tyr Thr
                165                 170                 175

Ile Asp Phe Ala Ala Lys Gln Gly His Gly Lys Ile Glu His Leu Lys
            180                 185                 190

Thr Pro Glu Gln Asn Val Glu Leu Ala Ala Ala Glu Leu Lys Ala Asp
        195                 200                 205

Glu Lys Ser His Ala Val Ile Leu Gly Asp Thr Arg Tyr Gly Ser Glu
210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Ser Ile Ala Gly Lys Gln
            260

<210> SEQ ID NO 43
<211> LENGTH: 262
<212> TYPE: PRT
<213> ORGANISM: Neisseria meningitidis
```

<400> SEQUENCE: 43

Cys Ser Ser Gly Gly Gly Ser Gly Ser Gly Gly Val Ala Ala Asp
1               5                   10                  15

Ile Gly Thr Gly Leu Ala Asp Ala Leu Thr Thr Pro Leu Asp His Lys
                20                  25                  30

Asp Lys Gly Leu Lys Ser Leu Thr Leu Glu Asp Ser Ile Pro Gln Asn
            35                  40                  45

Gly Thr Leu Thr Leu Ser Ala Gln Gly Ala Glu Lys Thr Phe Lys Ala
50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asp His Ser
                100                 105                 110

Ala Val Val Ala Leu Gln Ile Glu Lys Ile Asn Asn Pro Asp Lys Ile
            115                 120                 125

Asp Ser Leu Ile Asn Gln Arg Ser Phe Leu Val Ser Gly Leu Gly Gly
130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Ala Gly Lys Leu Thr Tyr Thr
                165                 170                 175

Ile Asp Phe Ala Ala Lys Gln Gly His Gly Lys Ile Glu His Leu Lys
                180                 185                 190

Thr Pro Glu Gln Asn Val Glu Leu Ala Ala Ala Glu Leu Lys Ala Asp
                195                 200                 205

Glu Lys Ser His Ala Val Ile Leu Gly Asp Thr Arg Tyr Gly Ser Glu
            210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
                260

<210> SEQ ID NO 44
<211> LENGTH: 260
<212> TYPE: PRT
<213> ORGANISM: Neisseria meningitidis

<400> SEQUENCE: 44

Cys Ser Ser Gly Gly Gly Ser Gly Gly Ile Ala Ala Asp Ile Gly
1               5                   10                  15

Thr Gly Leu Ala Asp Ala Leu Thr Ala Pro Leu Asp His Lys Asp Lys
                20                  25                  30

Gly Leu Lys Ser Leu Thr Leu Glu Asp Ser Ile Pro Gln Asn Gly Thr
            35                  40                  45

Leu Thr Leu Ser Ala Gln Gly Ala Glu Lys Thr Phe Lys Ala Gly Asp
50                  55                  60

Lys Asp Asn Ser Leu Asn Thr Gly Lys Leu Lys Asn Asp Lys Ile Ser
65                  70                  75                  80

Arg Phe Asp Phe Val Gln Lys Ile Glu Val Asp Gly Gln Thr Ile Thr
                85                  90                  95

Leu Ala Ser Gly Glu Phe Gln Ile Tyr Lys Gln Asp His Ser Ala Val
            100                 105                 110

Val Ala Leu Gln Ile Glu Lys Ile Asn Asn Pro Asp Lys Ile Asp Ser
        115                 120                 125

Leu Ile Asn Gln Arg Ser Phe Leu Val Ser Gly Leu Gly Gly Glu His
    130                 135                 140

Thr Ala Phe Asn Gln Leu Pro Gly Gly Lys Ala Glu Tyr His Gly Lys
145                 150                 155                 160

Ala Phe Ser Ser Asp Asp Ala Gly Gly Lys Leu Thr Tyr Thr Ile Asp
                165                 170                 175

Phe Ala Ala Lys Gln Gly His Gly Lys Ile Glu His Leu Lys Thr Pro
            180                 185                 190

Glu Gln Asn Val Glu Leu Ala Ala Ala Glu Leu Lys Ala Asp Glu Lys
        195                 200                 205

Ser His Ala Val Ile Leu Gly Asp Thr Arg Tyr Gly Ser Glu Glu Lys
    210                 215                 220

Gly Thr Tyr His Leu Ala Leu Phe Gly Asp Arg Ala Gln Glu Ile Ala
225                 230                 235                 240

Gly Ser Ala Thr Val Lys Ile Gly Glu Lys Val His Glu Ile Gly Ile
                245                 250                 255

Ala Gly Lys Gln
            260

<210> SEQ ID NO 45
<211> LENGTH: 262
<212> TYPE: PRT
<213> ORGANISM: Neisseria meningitidis

<400> SEQUENCE: 45

Cys Ser Ser Gly Gly Gly Gly Ser Gly Gly Gly Val Ala Ala Asp
1               5                   10                  15

Ile Gly Ala Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Gly Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asp His Ser
            100                 105                 110

Ala Val Val Ala Leu Gln Ile Glu Lys Ile Asn Asn Pro Asp Lys Thr
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Thr
                165                 170                 175

Ile Asp Phe Thr Asn Lys Gln Gly Tyr Gly Arg Ile Glu His Leu Lys
            180                 185                 190

Thr Pro Glu Gln Asn Val Glu Leu Ala Ser Ala Glu Leu Lys Ala Asp
        195                 200                 205

```
Glu Lys Ser His Ala Val Ile Leu Gly Asp Thr Arg Tyr Gly Ser Glu
    210                 215                 220
Glu Lys Gly Thr Tyr His Leu Ala Leu Phe Gly Asp Arg Ala Gln Glu
225                 230                 235                 240
Ile Ala Gly Ser Ala Thr Val Lys Ile Gly Glu Lys Val His Glu Ile
                245                 250                 255
Gly Ile Ala Gly Lys Gln
            260

<210> SEQ ID NO 46
<211> LENGTH: 12
<212> TYPE: PRT
<213> ORGANISM: Neisseria gonorrhoeae

<400> SEQUENCE: 46

Gly Pro Asp Ser Asp Arg Leu Gln Gln Arg Arg Gly
  1               5                  10

<210> SEQ ID NO 47
<211> LENGTH: 31
<212> TYPE: DNA
<213> ORGANISM: Artificial Sequence
<220> FEATURE:
<223> OTHER INFORMATION: Synthetic Construct

<400> SEQUENCE: 47
cgcggatccc atatggtcgc cgccgacatc g                                 31

<210> SEQ ID NO 48
<211> LENGTH: 27
<212> TYPE: DNA
<213> ORGANISM: Artificial Sequence
<220> FEATURE:
<223> OTHER INFORMATION: Synthetic Construct

<400> SEQUENCE: 48
cccgctcgag ttgcttggcg gcaaggc                                      27

<210> SEQ ID NO 49
<211> LENGTH: 65
<212> TYPE: DNA
<213> ORGANISM: Artificial Sequence
<220> FEATURE:
<223> OTHER INFORMATION: Synthetic Construct

<400> SEQUENCE: 49
cgcggatccc atatgggccc tgattctgac cgcctgcagc agcggagggt cgccgccgac    60
atcgg                                                                65

<210> SEQ ID NO 50
<211> LENGTH: 28
<212> TYPE: DNA
<213> ORGANISM: Artificial Sequence
<220> FEATURE:
<223> OTHER INFORMATION: Synthetic Construct

<400> SEQUENCE: 50
cccgctcgag ctgtttgccg gcgatgcc                                     28

<210> SEQ ID NO 51
<211> LENGTH: 65
<212> TYPE: DNA
<213> ORGANISM: Artificial Sequence
```

```
<220> FEATURE:
<223> OTHER INFORMATION: Synthetic Construct

<400> SEQUENCE: 51
cgcggatccc atatgggccc tgattctgac cgcctgcagc agcggagggg aggggggtggt    60 gtcgc                                                                  65

<210> SEQ ID NO 52
<211> LENGTH: 28
<212> TYPE: DNA
<213> ORGANISM: Artificial Sequence
<220> FEATURE:
<223> OTHER INFORMATION: Synthetic Construct

<400> SEQUENCE: 52
gcccaagctt ctgtttgccg gcgatgcc                                         28

<210> SEQ ID NO 53
<211> LENGTH: 37
<212> TYPE: DNA
<213> ORGANISM: Artificial Sequence
<220> FEATURE:
<223> OTHER INFORMATION: Synthetic Construct

<400> SEQUENCE: 53
cgcggatccc atatgaatcg aactgccttc tgctgcc                               37

<210> SEQ ID NO 54
<211> LENGTH: 30
<212> TYPE: DNA
<213> ORGANISM: Artificial Sequence
<220> FEATURE:
<223> OTHER INFORMATION: Synthetic Construct

<400> SEQUENCE: 54
cccgctcgag ttattgcttg gcggcaaggc                                       30

<210> SEQ ID NO 55
<211> LENGTH: 17
<212> TYPE: DNA
<213> ORGANISM: Artificial Sequence
<220> FEATURE:
<223> OTHER INFORMATION: Synthetic Construct

<400> SEQUENCE: 55
gacctgcctc attgatg                                                     17

<210> SEQ ID NO 56
<211> LENGTH: 25
<212> TYPE: DNA
<213> ORGANISM: Artificial Sequence
<220> FEATURE:
<223> OTHER INFORMATION: Synthetic Construct

<400> SEQUENCE: 56
cggtaaatta tcgtgttcgg acggc                                            25

<210> SEQ ID NO 57
<211> LENGTH: 21
<212> TYPE: DNA
<213> ORGANISM: Artificial Sequence
<220> FEATURE:
<223> OTHER INFORMATION: Synthetic Construct

<400> SEQUENCE: 57
```

```
caaatcgaag tggacgggca g                                              21
```

<210> SEQ ID NO 58
<211> LENGTH: 23
<212> TYPE: DNA
<213> ORGANISM: Artificial Sequence
<220> FEATURE:
<223> OTHER INFORMATION: Synthetic Construct

<400> SEQUENCE: 58

```
tgttcgattt tgccgtttcc ctg                                            23
```

<210> SEQ ID NO 59
<211> LENGTH: 24
<212> TYPE: DNA
<213> ORGANISM: Artificial Sequence
<220> FEATURE:
<223> OTHER INFORMATION: Synthetic Construct

<400> SEQUENCE: 59

```
gctctagacc agccaggcgc atac                                           24
```

<210> SEQ ID NO 60
<211> LENGTH: 29
<212> TYPE: DNA
<213> ORGANISM: Artificial Sequence
<220> FEATURE:
<223> OTHER INFORMATION: Synthetic Construct

<400> SEQUENCE: 60

```
tcccccgggg acggcatttt gtttacagg                                      29
```

<210> SEQ ID NO 61
<211> LENGTH: 28
<212> TYPE: DNA
<213> ORGANISM: Artificial Sequence
<220> FEATURE:
<223> OTHER INFORMATION: Synthetic Construct

<400> SEQUENCE: 61

```
tcccccgggc gccaagcaat aaccattg                                       28
```

<210> SEQ ID NO 62
<211> LENGTH: 28
<212> TYPE: DNA
<213> ORGANISM: Artificial Sequence
<220> FEATURE:
<223> OTHER INFORMATION: Synthetic Construct

<400> SEQUENCE: 62

```
cccgctcgag cagcgtatcg aaccatgc                                       28
```

<210> SEQ ID NO 63
<211> LENGTH: 27
<212> TYPE: DNA
<213> ORGANISM: Artificial Sequence
<220> FEATURE:
<223> OTHER INFORMATION: Synthetic Construct

<400> SEQUENCE: 63

```
gctctagatt ctttcccaag aactctc                                        27
```

<210> SEQ ID NO 64
<211> LENGTH: 26
<212> TYPE: DNA
<213> ORGANISM: Artificial Sequence

```
<220> FEATURE:
<223> OTHER INFORMATION: Synthetic Construct

<400> SEQUENCE: 64
tcccccgggc ccgtatcatc caccac                                          26

<210> SEQ ID NO 65
<211> LENGTH: 26
<212> TYPE: DNA
<213> ORGANISM: Artificial Sequence
<220> FEATURE:
<223> OTHER INFORMATION: Synthetic Construct

<400> SEQUENCE: 65
tcccccggga tccacgcaaa tacccc                                          26

<210> SEQ ID NO 66
<211> LENGTH: 28
<212> TYPE: DNA
<213> ORGANISM: Artificial Sequence
<220> FEATURE:
<223> OTHER INFORMATION: Synthetic Construct

<400> SEQUENCE: 66
cccgctcgag atataagtgg aagacgga                                        28

<210> SEQ ID NO 67
<211> LENGTH: 6
<212> TYPE: PRT
<213> ORGANISM: Neisseria meningitidis

<400> SEQUENCE: 67

Leu Asn Gln Ile Val Lys
  1               5

<210> SEQ ID NO 68
<211> LENGTH: 20
<212> TYPE: PRT
<213> ORGANISM: Neisseria meningitidis

<400> SEQUENCE: 68

Val Asn Arg Thr Ala Phe Cys Cys Leu Ser Leu Thr Thr Ala Leu Ile
  1               5                  10                  15

Leu Thr Ala Cys
             20

<210> SEQ ID NO 69
<211> LENGTH: 240
<212> TYPE: DNA
<213> ORGANISM: Neisseria meningitidis

<400> SEQUENCE: 69
aattgaacca atcgtcaaa taacaggttg cctgtaaaca aaatgccgtc tgaaccgccg      60
ttcggacgac atttgatttt tgcttctttg acctgcctca ttgatgcggt atgcaaaaaa    120
agataccata accaaaatgt ttatatatta tctattctgc gtatgactag gagtaaacct    180
gtgaatcgaa ctgccttctg ctgcctttct ctgaccactg ccctgattct gaccgcctgc    240

<210> SEQ ID NO 70
<211> LENGTH: 5
<212> TYPE: PRT
<213> ORGANISM: Neisseria meningitidis

<400> SEQUENCE: 70
```

```
Thr Arg Ser Lys Pro
  1               5

<210> SEQ ID NO 71
<211> LENGTH: 6
<212> TYPE: PRT
<213> ORGANISM: Neisseria meningitidis

<400> SEQUENCE: 71

Thr Arg Ser Lys Pro Val
  1               5

<210> SEQ ID NO 72
<211> LENGTH: 7
<212> TYPE: PRT
<213> ORGANISM: Neisseria meningitidis

<400> SEQUENCE: 72

Pro Ser Glu Pro Pro Phe Gly
  1               5

<210> SEQ ID NO 73
<211> LENGTH: 4
<212> TYPE: PRT
<213> ORGANISM: Artificial Sequence
<220> FEATURE:
<223> OTHER INFORMATION: Synthetic Construct

<400> SEQUENCE: 73

Gly Gly Gly Gly
  1

<210> SEQ ID NO 74
<211> LENGTH: 19
<212> TYPE: DNA
<213> ORGANISM: Neisseria meningitidis

<400> SEQUENCE: 74
cataaccaaa atgtttata                                                  19

<210> SEQ ID NO 75
<211> LENGTH: 19
<212> TYPE: DNA
<213> ORGANISM: Escherichia coli

<400> SEQUENCE: 75
gataatgata atcattatc                                                  19

<210> SEQ ID NO 76
<211> LENGTH: 179
<212> TYPE: PRT
<213> ORGANISM: Neisseria meningitidis

<400> SEQUENCE: 76

Val Ser Ala Val Ile Gly Ser Ala Ala Val Gly Ala Lys Ser Ala Val
  1               5                  10                  15

Asp Arg Arg Thr Thr Gly Ala Gln Thr Asp Asp Asn Val Met Ala Leu
                 20                  25                  30

Arg Ile Glu Thr Thr Ala Arg Ser Tyr Leu Arg Gln Asn Asn Gln Thr
             35                  40                  45

Lys Gly Tyr Thr Pro Gln Ile Ser Val Val Gly Tyr Asn Arg His Leu
         50                  55                  60
```

```
Leu Leu Leu Gly Gln Val Ala Thr Glu Gly Glu Lys Gln Phe Val Gly
 65                  70                  75                  80

Gln Ile Ala Arg Ser Glu Gln Ala Ala Glu Gly Val Tyr Asn Tyr Ile
                 85                  90                  95

Thr Val Ala Ser Leu Pro Arg Thr Ala Gly Asp Ile Ala Gly Asp Thr
            100                 105                 110

Trp Asn Thr Ser Lys Val Arg Ala Thr Leu Leu Gly Ile Ser Pro Ala
        115                 120                 125

Thr Gln Ala Arg Val Lys Ile Val Thr Tyr Gly Asn Val Thr Tyr Val
    130                 135                 140

Met Gly Ile Leu Thr Pro Glu Glu Gln Ala Gln Ile Thr Gln Lys Val
145                 150                 155                 160

Ser Thr Thr Val Gly Val Gln Lys Val Ile Thr Leu Tyr Gln Asn Tyr
                165                 170                 175

Val Gln Arg
```

<210> SEQ ID NO 77
<211> LENGTH: 436
<212> TYPE: PRT
<213> ORGANISM: Artificial Sequence
<220> FEATURE:
<223> OTHER INFORMATION: Synthetic Construct

<400> SEQUENCE: 77

```
Met Val Ser Ala Val Ile Gly Ser Ala Ala Val Gly Ala Lys Ser Ala
  1               5                  10                  15

Val Asp Arg Arg Thr Thr Gly Ala Gln Thr Asp Asp Asn Val Met Ala
                 20                  25                  30

Leu Arg Ile Glu Thr Thr Ala Arg Ser Tyr Leu Arg Gln Asn Asn Gln
             35                  40                  45

Thr Lys Gly Tyr Thr Pro Gln Ile Ser Val Val Gly Tyr Asn Arg His
     50                  55                  60

Leu Leu Leu Leu Gly Gln Val Ala Thr Glu Gly Glu Lys Gln Phe Val
 65                  70                  75                  80

Gly Gln Ile Ala Arg Ser Glu Gln Ala Ala Glu Gly Val Tyr Asn Tyr
                 85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
        115                 120                 125

Ala Thr Gln Ala Arg Val Lys Ile Val Thr Tyr Gly Asn Val Thr Tyr
    130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
                180                 185                 190

Thr Gly Leu Ala Asp Ala Leu Thr Ala Pro Leu Asp His Lys Asp Lys
        195                 200                 205

Gly Leu Lys Ser Leu Thr Leu Glu Asp Ser Ile Pro Gln Asn Gly Thr
    210                 215                 220

Leu Thr Leu Ser Ala Gln Gly Ala Glu Lys Thr Phe Lys Ala Gly Asp
225                 230                 235                 240

Lys Asp Asn Ser Leu Asn Thr Gly Lys Leu Lys Asn Asp Lys Ile Ser
```

```
                245                 250                 255
Arg Phe Asp Phe Val Gln Lys Ile Glu Val Asp Gly Gln Thr Ile Thr
            260                 265                 270

Leu Ala Ser Gly Glu Phe Gln Ile Tyr Lys Gln Asn His Ser Ala Val
            275                 280                 285

Val Ala Leu Gln Ile Glu Lys Ile Asn Asn Pro Asp Lys Thr Asp Ser
            290                 295                 300

Leu Ile Asn Gln Arg Ser Phe Leu Val Ser Gly Leu Gly Gly Glu His
305                 310                 315                 320

Thr Ala Phe Asn Gln Leu Pro Gly Gly Lys Ala Glu Tyr His Gly Lys
            325                 330                 335

Ala Phe Ser Ser Asp Asp Pro Asn Gly Arg Leu His Tyr Ser Ile Asp
            340                 345                 350

Phe Thr Lys Lys Gln Gly Tyr Gly Arg Ile Glu His Leu Lys Thr Leu
            355                 360                 365

Glu Gln Asn Val Glu Leu Ala Ala Ala Glu Leu Lys Ala Asp Glu Lys
            370                 375                 380

Ser His Ala Val Ile Leu Gly Asp Thr Arg Tyr Gly Ser Glu Glu Lys
385                 390                 395                 400

Gly Thr Tyr His Leu Ala Leu Phe Gly Asp Arg Ala Gln Glu Ile Ala
                405                 410                 415

Gly Ser Ala Thr Val Lys Ile Gly Glu Lys Val His Glu Ile Gly Ile
            420                 425                 430

Ala Gly Lys Gln
        435

<210> SEQ ID NO 78
<211> LENGTH: 13
<212> TYPE: PRT
<213> ORGANISM: Artificial Sequence
<220> FEATURE:
<223> OTHER INFORMATION: Synthetic Construct

<400> SEQUENCE: 78

Gly Ser Gly Pro Asp Ser Asp Arg Leu Gln Gln Arg Arg
1               5                   10

<210> SEQ ID NO 79
<211> LENGTH: 508
<212> TYPE: PRT
<213> ORGANISM: Artificial Sequence
<220> FEATURE:
<223> OTHER INFORMATION: Synthetic Construct

<400> SEQUENCE: 79

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95
```

-continued

```
Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Ile Ala
            115                 120                 125

Gly Glu His Thr Ser Phe Asp Lys Leu Pro Glu Gly Arg Ala Thr
        130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Asp Ile Lys
            180                 185                 190

Pro Asp Gly Lys Arg His Ala Val Ile Ser Gly Ser Val Leu Tyr Asn
            195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln Gly Ser Gly Pro Asp Ser Asp Arg
                245                 250                 255

Leu Gln Gln Arg Arg Val Ala Ala Asp Ile Gly Ala Gly Leu Ala Asp
            260                 265                 270

Ala Leu Thr Ala Pro Leu Asp His Lys Asp Lys Ser Leu Gln Ser Leu
        275                 280                 285

Thr Leu Asp Gln Ser Val Arg Lys Asn Glu Lys Leu Lys Leu Ala Ala
290                 295                 300

Gln Gly Ala Glu Lys Thr Tyr Gly Asn Gly Asp Ser Leu Asn Thr Gly
305                 310                 315                 320

Lys Leu Lys Asn Asp Lys Val Ser Arg Phe Asp Phe Ile Arg Gln Ile
                325                 330                 335

Glu Val Asp Gly Gln Leu Ile Thr Leu Glu Ser Gly Glu Phe Gln Ile
            340                 345                 350

Tyr Lys Gln Asp His Ser Ala Val Val Ala Leu Gln Ile Glu Lys Ile
        355                 360                 365

Asn Asn Pro Asp Lys Ile Asp Ser Leu Ile Asn Gln Arg Ser Phe Leu
370                 375                 380

Val Ser Gly Leu Gly Gly Glu His Thr Ala Phe Asn Gln Leu Pro Asp
385                 390                 395                 400

Gly Lys Ala Glu Tyr His Gly Lys Ala Phe Ser Ser Asp Asp Ala Gly
                405                 410                 415

Gly Lys Leu Thr Tyr Thr Ile Asp Phe Ala Ala Lys Gln Gly His Gly
            420                 425                 430

Lys Ile Glu His Leu Lys Thr Pro Glu Gln Asn Val Glu Leu Ala Ala
        435                 440                 445

Ala Glu Leu Lys Ala Asp Glu Lys Ser His Ala Val Ile Leu Gly Asp
    450                 455                 460

Thr Arg Tyr Gly Ser Glu Glu Lys Gly Thr Tyr His Leu Ala Leu Phe
465                 470                 475                 480

Gly Asp Arg Ala Gln Glu Ile Ala Gly Ser Ala Thr Val Lys Ile Gly
                485                 490                 495

Glu Lys Val His Glu Ile Gly Ile Ala Gly Lys Gln
            500                 505
```

```
<210> SEQ ID NO 80
<211> LENGTH: 248
<212> TYPE: PRT
<213> ORGANISM: Neisseria meningitidis

<400> SEQUENCE: 80

Val Ala Asp Ile Gly Ala Gly Leu Ala Asp Ala Leu Thr Ala Pro
 1               5                  10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Ile Ala
            115                 120                 125

Gly Glu His Thr Ser Phe Asp Lys Leu Pro Glu Gly Gly Arg Ala Thr
        130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Asp Ile Lys
                180                 185                 190

Pro Asp Gly Lys Arg His Ala Val Ile Ser Gly Ser Val Leu Tyr Asn
            195                 200                 205

Gln Ala Glu Lys Gly Ser Tyr Ser Leu Gly Ile Phe Gly Gly Lys Ala
        210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 81
<211> LENGTH: 247
<212> TYPE: PRT
<213> ORGANISM: Neisseria meningitidis

<400> SEQUENCE: 81

Val Ala Ala Asp Ile Gly Ala Gly Leu Ala Asp Ala Leu Thr Ala Pro
 1               5                  10                  15

Leu Asp His Lys Asp Lys Ser Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Ile Tyr Lys Gln Asp His
```

```
            85                  90                  95
Ser Ala Val Val Ala Leu Gln Ile Glu Lys Ile Asn Asn Pro Asp Lys
            100                 105                 110

Ile Asp Ser Leu Ile Asn Gln Arg Ser Phe Leu Val Ser Gly Leu Gly
            115                 120                 125

Gly Glu His Thr Ala Phe Asn Gln Leu Pro Asp Gly Lys Ala Glu Tyr
            130                 135                 140

His Gly Lys Ala Phe Ser Ser Asp Ala Gly Gly Lys Leu Thr Tyr
145                 150                 155                 160

Thr Ile Asp Phe Ala Ala Lys Gln Gly His Gly Lys Ile Glu His Leu
                    165                 170                 175

Lys Thr Pro Glu Gln Asn Val Glu Leu Ala Ala Glu Leu Lys Ala
            180                 185                 190

Asp Glu Lys Ser His Ala Val Ile Leu Gly Asp Thr Arg Tyr Gly Ser
            195                 200                 205

Glu Glu Lys Gly Thr Tyr His Leu Ala Leu Phe Gly Asp Arg Ala Gln
            210                 215                 220

Glu Ile Ala Gly Ser Ala Thr Val Lys Ile Gly Glu Lys Val His Glu
225                 230                 235                 240

Ile Gly Ile Ala Gly Lys Gln
                245

<210> SEQ ID NO 82
<211> LENGTH: 501
<212> TYPE: PRT
<213> ORGANISM: Artificial Sequence
<220> FEATURE:
<223> OTHER INFORMATION: Synthetic Construct

<400> SEQUENCE: 82

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
            115                 120                 125

Gly Glu His Thr Ser Phe Asp Lys Leu Pro Glu Gly Gly Arg Ala Thr
            130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                    165                 170                 175

Leu Lys Ser Pro Glu Leu Asn Val Asp Leu Ala Ala Ala Asp Ile Lys
            180                 185                 190

Pro Asp Gly Lys Arg His Ala Val Ile Ser Gly Ser Val Leu Tyr Asn
```

```
            195                 200                 205
Gln Ala Glu Lys Gly Ser Tyr Ser Leu Gly Ile Phe Gly Gly Lys Ala
210                 215                 220

Gln Glu Val Ala Gly Ser Ala Glu Val Lys Thr Val Asn Gly Ile Arg
225                 230                 235                 240

His Ile Gly Leu Ala Ala Lys Gln Gly Ser Gly Gly Gly Val Ala
                245                 250                 255

Ala Asp Ile Gly Ala Gly Leu Ala Asp Ala Leu Thr Ala Pro Leu Asp
                260                 265                 270

His Lys Asp Lys Ser Leu Gln Ser Leu Thr Leu Asp Gln Ser Val Arg
                275                 280                 285

Lys Asn Glu Lys Leu Lys Leu Ala Ala Gln Gly Ala Glu Lys Thr Tyr
290                 295                 300

Gly Asn Gly Asp Ser Leu Asn Thr Gly Lys Leu Lys Asn Asp Lys Val
305                 310                 315                 320

Ser Arg Phe Asp Phe Ile Arg Gln Ile Glu Val Asp Gly Gln Leu Ile
                325                 330                 335

Thr Leu Glu Ser Gly Glu Phe Gln Ile Tyr Lys Gln Asp His Ser Ala
                340                 345                 350

Val Val Ala Leu Gln Ile Glu Lys Ile Asn Asn Pro Asp Lys Ile Asp
                355                 360                 365

Ser Leu Ile Asn Gln Arg Ser Phe Leu Val Ser Gly Leu Gly Gly Glu
370                 375                 380

His Thr Ala Phe Asn Gln Leu Pro Asp Gly Lys Ala Glu Tyr His Gly
385                 390                 395                 400

Lys Ala Phe Ser Ser Asp Asp Ala Gly Gly Lys Leu Thr Tyr Thr Ile
                405                 410                 415

Asp Phe Ala Ala Lys Gln Gly His Gly Lys Ile Glu His Leu Lys Thr
                420                 425                 430

Pro Glu Gln Asn Val Glu Leu Ala Ala Ala Glu Leu Lys Ala Asp Glu
                435                 440                 445

Lys Ser His Ala Val Ile Leu Gly Asp Thr Arg Tyr Gly Ser Glu Glu
450                 455                 460

Lys Gly Thr Tyr His Leu Ala Leu Phe Gly Asp Arg Ala Gln Glu Ile
465                 470                 475                 480

Ala Gly Ser Ala Thr Val Lys Ile Gly Glu Lys Val His Glu Ile Gly
                485                 490                 495

Ile Ala Gly Lys Gln
                500

<210> SEQ ID NO 83
<211> LENGTH: 511
<212> TYPE: PRT
<213> ORGANISM: Artificial Sequence
<220> FEATURE:
<223> OTHER INFORMATION: Synthetic Construct

<400> SEQUENCE: 83

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
                35                  40                  45

Thr Tyr Gly Asn Gly Asp Ser Leu Asn Thr Gly Lys Leu Lys Asn Asp
```

```
                50                  55                  60
Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                     85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Ile Ala
                115                 120                 125

Gly Glu His Thr Ser Phe Asp Lys Leu Pro Glu Gly Gly Arg Ala Thr
130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
                180                 185                 190

Pro Asp Gly Lys Arg His Ala Val Ile Ser Gly Ser Val Leu Tyr Asn
                195                 200                 205

Gln Ala Glu Lys Gly Ser Tyr Ser Leu Gly Ile Phe Gly Gly Lys Ala
                210                 215                 220

Gln Glu Val Ala Gly Ser Ala Glu Val Lys Thr Val Asn Gly Ile Arg
225                 230                 235                 240

His Ile Gly Leu Ala Ala Lys Gln Gly Ser Gly Pro Asp Ser Asp Arg
                245                 250                 255

Leu Gln Gln Arg Arg Val Ala Ala Asp Ile Gly Thr Gly Leu Ala Asp
                260                 265                 270

Ala Leu Thr Ala Pro Leu Asp His Lys Asp Lys Gly Leu Lys Ser Leu
                275                 280                 285

Thr Leu Glu Asp Ser Ile Pro Gln Asn Gly Thr Leu Thr Leu Ser Ala
290                 295                 300

Gln Gly Ala Glu Lys Thr Phe Lys Ala Gly Asp Lys Asp Asn Ser Leu
305                 310                 315                 320

Asn Thr Gly Lys Leu Lys Asn Asp Lys Ile Ser Arg Phe Asp Phe Val
                325                 330                 335

Gln Lys Ile Glu Val Asp Gly Gln Thr Ile Thr Leu Ala Ser Gly Glu
                340                 345                 350

Phe Gln Ile Tyr Lys Gln Asn His Ser Ala Val Val Ala Leu Gln Ile
                355                 360                 365

Glu Lys Ile Asn Asn Pro Asp Lys Thr Asp Ser Leu Ile Asn Gln Arg
                370                 375                 380

Ser Phe Leu Val Ser Gly Leu Gly Gly Glu His Thr Ala Phe Asn Gln
385                 390                 395                 400

Leu Pro Gly Gly Lys Ala Glu Tyr His Gly Lys Ala Phe Ser Ser Asp
                405                 410                 415

Asp Pro Asn Gly Arg Leu His Tyr Ser Ile Asp Phe Thr Lys Lys Gln
                420                 425                 430

Gly Tyr Gly Arg Ile Glu His Leu Lys Thr Leu Glu Gln Asn Val Glu
                435                 440                 445

Leu Ala Ala Ala Glu Leu Lys Ala Asp Glu Lys Ser His Ala Val Ile
                450                 455                 460

Leu Gly Asp Thr Arg Tyr Gly Ser Glu Glu Lys Gly Thr Tyr His Leu
465                 470                 475                 480
```

```
Ala Leu Phe Gly Asp Arg Ala Gln Glu Ile Ala Gly Ser Ala Thr Val
                485                 490                 495

Lys Ile Gly Glu Lys Val His Glu Ile Gly Ile Ala Gly Lys Gln
            500                 505                 510

<210> SEQ ID NO 84
<211> LENGTH: 250
<212> TYPE: PRT
<213> ORGANISM: Neisseria meningitidis

<400> SEQUENCE: 84

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Leu Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250

<210> SEQ ID NO 85
<211> LENGTH: 504
<212> TYPE: PRT
<213> ORGANISM: Artificial Sequence
<220> FEATURE:
<223> OTHER INFORMATION: Synthetic Construct

<400> SEQUENCE: 85

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30
```

```
Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Val Tyr Lys Gln Ser His
                 85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
            115                 120                 125

Gly Glu His Thr Ser Phe Asp Lys Leu Pro Glu Gly Gly Arg Ala Thr
        130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln Gly Ser Gly Gly Gly Val Ala
                245                 250                 255

Ala Asp Ile Gly Thr Gly Leu Ala Asp Ala Leu Thr Ala Pro Leu Asp
                260                 265                 270

His Lys Asp Lys Gly Leu Lys Ser Leu Thr Leu Glu Asp Ser Ile Pro
        275                 280                 285

Gln Asn Gly Thr Leu Thr Leu Ser Ala Gln Gly Ala Glu Lys Thr Phe
    290                 295                 300

Lys Ala Gly Asp Lys Asp Asn Ser Leu Asn Thr Gly Lys Leu Lys Asn
305                 310                 315                 320

Asp Lys Ile Ser Arg Phe Asp Phe Val Gln Lys Ile Glu Val Asp Gly
                325                 330                 335

Gln Thr Ile Thr Leu Ala Ser Gly Glu Phe Gln Ile Tyr Lys Gln Asn
            340                 345                 350

His Ser Ala Val Val Ala Leu Gln Ile Glu Lys Ile Asn Asn Pro Asp
        355                 360                 365

Lys Thr Asp Ser Leu Ile Asn Gln Arg Ser Phe Leu Val Ser Gly Leu
    370                 375                 380

Gly Gly Glu His Thr Ala Phe Asn Gln Leu Pro Gly Gly Lys Ala Glu
385                 390                 395                 400

Tyr His Gly Lys Ala Phe Ser Ser Asp Pro Asn Gly Arg Leu His
                405                 410                 415

Tyr Ser Ile Asp Phe Thr Lys Lys Gln Gly Tyr Gly Arg Ile Glu His
                420                 425                 430

Leu Lys Thr Leu Glu Gln Asn Val Glu Leu Ala Ala Ala Glu Leu Lys
            435                 440                 445

Ala Asp Glu Lys Ser His Ala Val Ile Leu Gly Asp Thr Arg Tyr Gly
```

```
                450                 455                 460
Ser Glu Glu Lys Gly Thr Tyr His Leu Ala Leu Phe Gly Asp Arg Ala
465                 470                 475                 480

Gln Glu Ile Ala Gly Ser Ala Thr Val Lys Ile Gly Glu Lys Val His
                485                 490                 495

Glu Ile Gly Ile Ala Gly Lys Gln
            500

<210> SEQ ID NO 86
<211> LENGTH: 11
<212> TYPE: PRT
<213> ORGANISM: Artificial Sequence
<220> FEATURE:
<223> OTHER INFORMATION: Synthetic Construct

<400> SEQUENCE: 86

Gly Pro Asp Ser Asp Arg Leu Gln Gln Arg Arg
 1               5                  10

<210> SEQ ID NO 87
<211> LENGTH: 521
<212> TYPE: PRT
<213> ORGANISM: Artificial Sequence
<220> FEATURE:
<223> OTHER INFORMATION: Synthetic Construct

<400> SEQUENCE: 87

Gly Pro Asp Ser Asp Arg Leu Gln Gln Arg Arg Val Ala Ala Asp Ile
 1               5                  10                  15

Gly Ala Gly Leu Ala Asp Ala Leu Thr Ala Pro Leu Asp His Lys Asp
                20                  25                  30

Lys Ser Leu Gln Ser Leu Thr Leu Asp Gln Ser Val Arg Lys Asn Glu
            35                  40                  45

Lys Leu Lys Leu Ala Ala Gln Gly Ala Glu Lys Thr Tyr Gly Asn Gly
        50                  55                  60

Asp Ser Leu Asn Thr Gly Lys Leu Lys Asn Asp Lys Val Ser Arg Phe
65                  70                  75                  80

Asp Phe Ile Arg Gln Ile Glu Val Asp Gly Gln Leu Ile Thr Leu Glu
                85                  90                  95

Ser Gly Glu Phe Gln Ile Tyr Lys Gln Asp His Ser Ala Val Val Ala
            100                 105                 110

Leu Gln Ile Glu Lys Ile Asn Asn Pro Asp Lys Ile Asp Ser Leu Ile
        115                 120                 125

Asn Gln Arg Ser Phe Leu Val Ser Gly Leu Gly Gly Glu His Thr Ala
130                 135                 140

Phe Asn Gln Leu Pro Asp Gly Lys Ala Glu Tyr His Gly Lys Ala Phe
145                 150                 155                 160

Ser Ser Asp Asp Ala Gly Gly Lys Leu Thr Tyr Thr Ile Asp Phe Ala
                165                 170                 175

Ala Lys Gln Gly His Gly Lys Ile Glu His Leu Lys Thr Pro Glu Gln
            180                 185                 190

Asn Val Glu Leu Ala Ala Ala Glu Leu Lys Ala Asp Glu Lys Ser His
        195                 200                 205

Ala Val Ile Leu Gly Asp Thr Arg Tyr Gly Ser Glu Glu Lys Gly Thr
    210                 215                 220

Tyr His Leu Ala Leu Phe Gly Asp Arg Ala Gln Glu Ile Ala Gly Ser
225                 230                 235                 240
```

```
Ala Thr Val Lys Ile Gly Glu Lys Val His Glu Ile Gly Ile Ala Gly
                245                 250                 255

Lys Gln Gly Ser Gly Pro Asp Ser Asp Arg Leu Gln Gln Arg Arg Val
            260                 265                 270

Ala Ala Asp Ile Gly Thr Gly Leu Ala Asp Ala Leu Thr Ala Pro Leu
        275                 280                 285

Asp His Lys Asp Lys Gly Leu Lys Ser Leu Thr Leu Glu Asp Ser Ile
    290                 295                 300

Pro Gln Asn Gly Thr Leu Thr Leu Ser Ala Gln Gly Ala Glu Lys Thr
305                 310                 315                 320

Phe Lys Ala Gly Asp Lys Asp Asn Ser Leu Asn Thr Gly Lys Leu Lys
                325                 330                 335

Asn Asp Lys Ile Ser Arg Phe Asp Phe Val Gln Lys Ile Glu Val Asp
            340                 345                 350

Gly Gln Thr Ile Thr Leu Ala Ser Gly Glu Phe Gln Ile Tyr Lys Gln
        355                 360                 365

Asn His Ser Ala Val Val Ala Leu Gln Ile Glu Lys Ile Asn Asn Pro
    370                 375                 380

Asp Lys Thr Asp Ser Leu Ile Asn Gln Arg Ser Phe Leu Val Ser Gly
385                 390                 395                 400

Leu Gly Gly Glu His Thr Ala Phe Asn Gln Leu Pro Gly Gly Lys Ala
                405                 410                 415

Glu Tyr His Gly Lys Ala Phe Ser Ser Asp Asp Pro Asn Gly Arg Leu
            420                 425                 430

His Tyr Ser Ile Asp Phe Thr Lys Lys Gln Gly Tyr Gly Arg Ile Glu
        435                 440                 445

His Leu Lys Thr Leu Glu Gln Asn Val Glu Leu Ala Ala Ala Glu Leu
    450                 455                 460

Lys Ala Asp Glu Lys Ser His Ala Val Ile Leu Gly Asp Thr Arg Tyr
465                 470                 475                 480

Gly Ser Glu Glu Lys Gly Thr Tyr His Leu Ala Leu Phe Gly Asp Arg
                485                 490                 495

Ala Gln Glu Ile Ala Gly Ser Ala Thr Val Lys Ile Gly Glu Lys Val
            500                 505                 510

His Glu Ile Gly Ile Ala Gly Lys Gln
        515                 520

<210> SEQ ID NO 88
<211> LENGTH: 514
<212> TYPE: PRT
<213> ORGANISM: Artificial Sequence
<220> FEATURE:
<223> OTHER INFORMATION: Synthetic Construct

<400> SEQUENCE: 88

Gly Pro Asp Ser Asp Arg Leu Gln Gln Arg Arg Val Ala Ala Asp Ile
1               5                   10                  15

Gly Ala Gly Leu Ala Asp Ala Leu Thr Ala Pro Leu Asp His Lys Asp
            20                  25                  30

Lys Ser Leu Gln Ser Leu Thr Leu Asp Gln Ser Val Arg Lys Asn Glu
        35                  40                  45

Lys Leu Lys Leu Ala Ala Gln Gly Ala Glu Lys Thr Tyr Gly Asn Gly
    50                  55                  60

Asp Ser Leu Asn Thr Gly Lys Leu Lys Asn Asp Lys Val Ser Arg Phe
65                  70                  75                  80
```

```
Asp Phe Ile Arg Gln Ile Glu Val Asp Gly Gln Leu Ile Thr Leu Glu
                85                  90                  95
Ser Gly Glu Phe Gln Ile Tyr Lys Gln Asp His Ser Ala Val Val Ala
            100                 105                 110
Leu Gln Ile Glu Lys Ile Asn Asn Pro Asp Lys Ile Asp Ser Leu Ile
        115                 120                 125
Asn Gln Arg Ser Phe Leu Val Ser Gly Leu Gly Gly Glu His Thr Ala
    130                 135                 140
Phe Asn Gln Leu Pro Asp Gly Lys Ala Glu Tyr His Gly Lys Ala Phe
145                 150                 155                 160
Ser Ser Asp Asp Ala Gly Gly Lys Leu Thr Tyr Thr Ile Asp Phe Ala
                165                 170                 175
Ala Lys Gln Gly His Gly Lys Ile Glu His Leu Lys Thr Pro Glu Gln
            180                 185                 190
Asn Val Glu Leu Ala Ala Ala Glu Leu Lys Ala Asp Glu Lys Ser His
        195                 200                 205
Ala Val Ile Leu Gly Asp Thr Arg Tyr Gly Ser Glu Glu Lys Gly Thr
    210                 215                 220
Tyr His Leu Ala Leu Phe Gly Asp Arg Ala Gln Glu Ile Ala Gly Ser
225                 230                 235                 240
Ala Thr Val Lys Ile Gly Glu Lys Val His Glu Ile Gly Ile Ala Gly
                245                 250                 255
Lys Gln Gly Ser Gly Gly Gly Val Ala Ala Asp Ile Gly Thr Gly
            260                 265                 270
Leu Ala Asp Ala Leu Thr Ala Pro Leu Asp His Lys Asp Lys Gly Leu
    275                 280                 285
Lys Ser Leu Thr Leu Glu Asp Ser Ile Pro Gln Asn Gly Thr Leu Thr
290                 295                 300
Leu Ser Ala Gln Gly Ala Glu Lys Thr Phe Lys Ala Gly Asp Lys Asp
305                 310                 315                 320
Asn Ser Leu Asn Thr Gly Lys Leu Lys Asn Asp Lys Ile Ser Arg Phe
                325                 330                 335
Asp Phe Val Gln Lys Ile Glu Val Asp Gly Gln Thr Ile Thr Leu Ala
            340                 345                 350
Ser Gly Glu Phe Gln Ile Tyr Lys Gln Asn His Ser Ala Val Val Ala
        355                 360                 365
Leu Gln Ile Glu Lys Ile Asn Asn Pro Asp Lys Thr Asp Ser Leu Ile
    370                 375                 380
Asn Gln Arg Ser Phe Leu Val Ser Gly Leu Gly Gly Glu His Thr Ala
385                 390                 395                 400
Phe Asn Gln Leu Pro Gly Gly Lys Ala Glu Tyr His Gly Lys Ala Phe
                405                 410                 415
Ser Ser Asp Asp Pro Asn Gly Arg Leu His Tyr Ser Ile Asp Phe Thr
            420                 425                 430
Lys Lys Gln Gly Tyr Gly Arg Ile Glu His Leu Lys Thr Leu Glu Gln
        435                 440                 445
Asn Val Glu Leu Ala Ala Ala Glu Leu Lys Ala Asp Glu Lys Ser His
    450                 455                 460
Ala Val Ile Leu Gly Asp Thr Arg Tyr Gly Ser Glu Glu Lys Gly Thr
465                 470                 475                 480
Tyr His Leu Ala Leu Phe Gly Asp Arg Ala Gln Glu Ile Ala Gly Ser
                485                 490                 495
Ala Thr Val Lys Ile Gly Glu Lys Val His Glu Ile Gly Ile Ala Gly
```

-continued

```
                500             505             510

Lys Gln

<210> SEQ ID NO 89
<211> LENGTH: 521
<212> TYPE: PRT
<213> ORGANISM: Artificial Sequence
<220> FEATURE:
<223> OTHER INFORMATION: Synthetic Construct

<400> SEQUENCE: 89

Gly Pro Asp Ser Asp Arg Leu Gln Gln Arg Val Ala Ala Asp Ile
 1               5                  10                  15

Gly Thr Gly Leu Ala Asp Ala Leu Thr Ala Pro Leu Asp His Lys Asp
                20                  25                  30

Lys Gly Leu Lys Ser Leu Thr Leu Glu Asp Ser Ile Pro Gln Asn Gly
                35                  40                  45

Thr Leu Thr Leu Ser Ala Gln Gly Ala Glu Lys Thr Phe Lys Ala Gly
        50                  55                  60

Asp Lys Asp Asn Ser Leu Asn Thr Gly Lys Leu Lys Asn Asp Lys Ile
65                  70                  75                  80

Ser Arg Phe Asp Phe Val Gln Lys Ile Glu Val Asp Gly Gln Thr Ile
                    85                  90                  95

Thr Leu Ala Ser Gly Glu Phe Gln Ile Tyr Lys Gln Asn His Ser Ala
                100                 105                 110

Val Val Ala Leu Gln Ile Glu Lys Ile Asn Asn Pro Asp Lys Thr Asp
                115                 120                 125

Ser Leu Ile Asn Gln Arg Ser Phe Leu Val Ser Gly Leu Gly Gly Glu
        130                 135                 140

His Thr Ala Phe Asn Gln Leu Pro Gly Gly Lys Ala Glu Tyr His Gly
145                 150                 155                 160

Lys Ala Phe Ser Ser Asp Asp Pro Asn Gly Arg Leu His Tyr Ser Ile
                    165                 170                 175

Asp Phe Thr Lys Lys Gln Gly Tyr Gly Arg Ile Glu His Leu Lys Thr
                180                 185                 190

Leu Glu Gln Asn Val Glu Leu Ala Ala Ala Glu Leu Lys Ala Asp Glu
                195                 200                 205

Lys Ser His Ala Val Ile Leu Gly Asp Thr Arg Tyr Gly Ser Glu Glu
        210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Gly Glu Lys Val His Glu Ile Gly
                    245                 250                 255

Ile Ala Gly Lys Gln Gly Ser Gly Pro Asp Ser Asp Arg Leu Gln Gln
                260                 265                 270

Arg Arg Val Ala Ala Asp Ile Gly Ala Gly Leu Ala Asp Ala Leu Thr
        275                 280                 285

Ala Pro Leu Asp His Lys Asp Lys Ser Leu Gln Ser Leu Thr Leu Asp
    290                 295                 300

Gln Ser Val Arg Lys Asn Glu Lys Leu Lys Leu Ala Ala Gln Gly Ala
305                 310                 315                 320

Glu Lys Thr Tyr Gly Asn Gly Asp Ser Leu Asn Thr Gly Lys Leu Lys
                    325                 330                 335

Asn Asp Lys Val Ser Arg Phe Asp Phe Ile Arg Gln Ile Glu Val Asp
                340                 345                 350
```

```
Gly Gln Leu Ile Thr Leu Glu Ser Gly Glu Phe Gln Ile Tyr Lys Gln
        355                 360                 365

Asp His Ser Ala Val Ala Leu Gln Ile Glu Lys Ile Asn Asn Pro
        370                 375                 380

Asp Lys Ile Asp Ser Leu Ile Asn Gln Arg Ser Phe Leu Val Ser Gly
385                 390                 395                 400

Leu Gly Gly Glu His Thr Ala Phe Asn Gln Leu Pro Asp Gly Lys Ala
                405                 410                 415

Glu Tyr His Gly Lys Ala Phe Ser Ser Asp Asp Ala Gly Gly Lys Leu
            420                 425                 430

Thr Tyr Thr Ile Asp Phe Ala Ala Lys Gln Gly His Gly Lys Ile Glu
        435                 440                 445

His Leu Lys Thr Pro Glu Gln Asn Val Glu Leu Ala Ala Ala Glu Leu
        450                 455                 460

Lys Ala Asp Glu Lys Ser His Ala Val Ile Leu Gly Asp Thr Arg Tyr
465                 470                 475                 480

Gly Ser Glu Glu Lys Gly Thr Tyr His Leu Ala Leu Phe Gly Asp Arg
                485                 490                 495

Ala Gln Glu Ile Ala Gly Ser Ala Thr Val Lys Ile Gly Glu Lys Val
            500                 505                 510

His Glu Ile Gly Ile Ala Gly Lys Gln
        515                 520

<210> SEQ ID NO 90
<211> LENGTH: 514
<212> TYPE: PRT
<213> ORGANISM: Artificial Sequence
<220> FEATURE:
<223> OTHER INFORMATION: Synthetic Construct

<400> SEQUENCE: 90

Gly Pro Asp Ser Asp Arg Leu Gln Gln Arg Val Ala Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Pro Gln Asn Gly
        35                  40                  45

Thr Leu Thr Leu Ser Ala Gln Gly Ala Glu Lys Thr Phe Lys Ala Gly
    50                  55                  60

Asp Lys Asp Asn Ser Leu Asn Thr Gly Lys Leu Lys Asn Asp Lys Ile
65                  70                  75                  80

Ser Arg Phe Asp Phe Val Gln Lys Ile Glu Val Asp Gly Gln Thr Ile
                85                  90                  95

Thr Leu Ala Ser Gly Glu Phe Gln Ile Tyr Lys Gln Asn His Ser Ala
            100                 105                 110

Val Val Ala Leu Gln Ile Glu Lys Ile Asn Asn Pro Asp Lys Thr Asp
        115                 120                 125

Ser Leu Ile Asn Gln Arg Ser Phe Leu Val Ser Gly Leu Gly Gly Glu
    130                 135                 140

His Thr Ala Phe Asn Gln Leu Pro Gly Gly Lys Ala Glu Tyr His Gly
145                 150                 155                 160

Lys Ala Phe Ser Ser Asp Asp Pro Asn Gly Arg Leu His Tyr Ser Ile
                165                 170                 175

Asp Phe Thr Lys Lys Gln Gly Tyr Gly Arg Ile Glu His Leu Lys Thr
            180                 185                 190
```

-continued

```
Leu Glu Gln Asn Val Glu Leu Ala Ala Ala Glu Leu Lys Ala Asp Glu
        195                 200                 205

Lys Ser His Ala Val Ile Leu Gly Asp Thr Arg Tyr Gly Ser Glu Glu
        210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Gly Glu Lys Val His Glu Ile Gly
                245                 250                 255

Ile Ala Gly Lys Gln Gly Ser Gly Gly Gly Val Ala Ala Asp Ile
        260                 265                 270

Gly Ala Gly Leu Ala Asp Ala Leu Thr Ala Pro Leu Asp His Lys Asp
        275                 280                 285

Lys Ser Leu Gln Ser Leu Thr Leu Asp Gln Ser Val Arg Lys Asn Glu
        290                 295                 300

Lys Leu Lys Leu Ala Ala Gln Gly Ala Glu Lys Thr Tyr Gly Asn Gly
305                 310                 315                 320

Asp Ser Leu Asn Thr Gly Lys Leu Lys Asn Asp Lys Val Ser Arg Phe
                325                 330                 335

Asp Phe Ile Arg Gln Ile Glu Val Asp Gly Gln Leu Ile Thr Leu Glu
        340                 345                 350

Ser Gly Glu Phe Gln Ile Tyr Lys Gln Asp His Ser Ala Val Val Ala
        355                 360                 365

Leu Gln Ile Glu Lys Ile Asn Asn Pro Asp Lys Ile Asp Ser Leu Ile
        370                 375                 380

Asn Gln Arg Ser Phe Leu Val Ser Gly Leu Gly Gly Glu His Thr Ala
385                 390                 395                 400

Phe Asn Gln Leu Pro Asp Gly Lys Ala Glu Tyr His Gly Lys Ala Phe
                405                 410                 415

Ser Ser Asp Asp Ala Gly Gly Lys Leu Thr Tyr Thr Ile Asp Phe Ala
        420                 425                 430

Ala Lys Gln Gly His Gly Lys Ile Glu His Leu Lys Thr Pro Glu Gln
        435                 440                 445

Asn Val Glu Leu Ala Ala Ala Glu Leu Lys Ala Asp Glu Lys Ser His
        450                 455                 460

Ala Val Ile Leu Gly Asp Thr Arg Tyr Gly Ser Glu Glu Lys Gly Thr
465                 470                 475                 480

Tyr His Leu Ala Leu Phe Gly Asp Arg Ala Gln Glu Ile Ala Gly Ser
                485                 490                 495

Ala Thr Val Lys Ile Gly Glu Lys Val His Glu Ile Gly Ile Ala Gly
        500                 505                 510

Lys Gln
```

<210> SEQ ID NO 91
<211> LENGTH: 440
<212> TYPE: PRT
<213> ORGANISM: Artificial Sequence
<220> FEATURE:
<223> OTHER INFORMATION: Synthetic Construct

<400> SEQUENCE: 91

```
Cys Val Ser Ala Val Ile Gly Ser Ala Val Gly Ala Lys Ser Ala
1               5                   10                  15

Val Asp Arg Arg Thr Thr Gly Ala Gln Thr Asp Asp Asn Val Met Ala
            20                  25                  30
```

-continued

```
Leu Arg Ile Glu Thr Thr Ala Arg Ser Tyr Leu Arg Gln Asn Asn Gln
 35                  40                  45

Thr Lys Gly Tyr Thr Pro Gln Ile Ser Val Val Gly Tyr Asn Arg His
 50                  55                  60

Leu Leu Leu Leu Gly Gln Val Ala Thr Glu Gly Glu Lys Gln Phe Val
 65                  70                  75                  80

Gly Gln Ile Ala Arg Ser Glu Gln Ala Ala Glu Gly Val Tyr Asn Tyr
                 85                  90                  95

Ile Thr Val Ala Ser Leu Pro Arg Thr Ala Gly Asp Ile Ala Gly Asp
                100                 105                 110

Thr Trp Asn Thr Ser Lys Val Arg Ala Thr Leu Leu Gly Ile Ser Pro
                115                 120                 125

Ala Thr Gln Ala Arg Val Lys Ile Val Thr Tyr Gly Asn Val Thr Tyr
    130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Pro Asp Ser Asp Arg Leu Gln Gln Arg
                180                 185                 190

Arg Val Ala Ala Asp Ile Gly Ala Gly Leu Ala Asp Ala Leu Thr Ala
            195                 200                 205

Pro Leu Asp His Lys Asp Lys Ser Leu Gln Ser Leu Thr Leu Asp Gln
    210                 215                 220

Ser Val Arg Lys Asn Glu Lys Leu Lys Leu Ala Ala Gln Gly Ala Glu
225                 230                 235                 240

Lys Thr Tyr Gly Asn Gly Asp Ser Leu Asn Thr Gly Lys Leu Lys Asn
                245                 250                 255

Asp Lys Val Ser Arg Phe Asp Phe Ile Arg Gln Ile Glu Val Asp Gly
                260                 265                 270

Gln Leu Ile Thr Leu Glu Ser Gly Glu Phe Gln Ile Tyr Lys Gln Asp
            275                 280                 285

His Ser Ala Val Val Ala Leu Gln Ile Glu Lys Ile Asn Asn Pro Asp
    290                 295                 300

Lys Ile Asp Ser Leu Ile Asn Gln Arg Ser Phe Leu Val Ser Gly Leu
305                 310                 315                 320

Gly Gly Glu His Thr Ala Phe Asn Gln Leu Pro Asp Gly Lys Ala Glu
                325                 330                 335

Tyr His Gly Lys Ala Phe Ser Ser Asp Asp Ala Gly Gly Lys Leu Thr
                340                 345                 350

Tyr Thr Ile Asp Phe Ala Ala Lys Gln Gly His Gly Lys Ile Glu His
            355                 360                 365

Leu Lys Thr Pro Glu Gln Asn Val Glu Leu Ala Ala Glu Leu Lys
    370                 375                 380

Ala Asp Glu Lys Ser His Ala Val Ile Leu Gly Asp Thr Arg Tyr Gly
385                 390                 395                 400

Ser Glu Glu Lys Gly Thr Tyr His Leu Ala Leu Phe Gly Asp Arg Ala
                405                 410                 415

Gln Glu Ile Ala Gly Ser Ala Thr Val Lys Ile Gly Glu Lys Val His
            420                 425                 430

Glu Ile Gly Ile Ala Gly Lys Gln
    435                 440
```

<210> SEQ ID NO 92
<211> LENGTH: 433
<212> TYPE: PRT
<213> ORGANISM: Artificial Sequence
<220> FEATURE:
<223> OTHER INFORMATION: Synthetic Construct

<400> SEQUENCE: 92

```
Cys Val Ser Ala Val Ile Gly Ser Ala Ala Val Gly Ala Lys Ser Ala
1               5                   10                  15

Val Asp Arg Arg Thr Thr Gly Ala Gln Thr Asp Asn Val Met Ala
            20                  25                  30

Leu Arg Ile Glu Thr Thr Ala Arg Ser Tyr Leu Arg Gln Asn Asn Gln
            35                  40                  45

Thr Lys Gly Tyr Thr Pro Gln Ile Ser Val Val Gly Tyr Asn Arg His
    50                  55                  60

Leu Leu Leu Leu Gly Gln Val Ala Thr Glu Gly Glu Lys Gln Phe Val
65                  70                  75                  80

Gly Gln Ile Ala Arg Ser Glu Gln Ala Glu Gly Val Tyr Asn Tyr
                85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
        115                 120                 125

Ala Thr Gln Ala Arg Val Lys Ile Val Thr Tyr Gly Asn Val Thr Tyr
    130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
            180                 185                 190

Ala Gly Leu Ala Asp Ala Leu Thr Ala Pro Leu Asp His Lys Asp Lys
        195                 200                 205

Ser Leu Gln Ser Leu Thr Leu Asp Gln Ser Val Arg Lys Asn Glu Lys
    210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
            260                 265                 270

Gly Glu Phe Gln Ile Tyr Lys Gln Asp His Ser Ala Val Val Ala Leu
        275                 280                 285

Gln Ile Glu Lys Ile Asn Asn Pro Asp Lys Ile Asp Ser Leu Ile Asn
    290                 295                 300

Gln Arg Ser Phe Leu Val Ser Gly Leu Gly Gly Glu His Thr Ala Phe
305                 310                 315                 320

Asn Gln Leu Pro Asp Gly Lys Ala Glu Tyr His Gly Lys Ala Phe Ser
                325                 330                 335

Ser Asp Asp Ala Gly Gly Lys Leu Thr Tyr Thr Ile Asp Phe Ala Ala
            340                 345                 350

Lys Gln Gly His Gly Lys Ile Glu His Leu Lys Thr Pro Glu Gln Asn
        355                 360                 365

Val Glu Leu Ala Ala Ala Glu Leu Lys Ala Asp Glu Lys Ser His Ala
```

```
              370                 375                 380
Val Ile Leu Gly Asp Thr Arg Tyr Gly Ser Glu Glu Lys Gly Thr Tyr
385                 390                 395                 400

His Leu Ala Leu Phe Gly Asp Arg Ala Gln Glu Ile Ala Gly Ser Ala
                405                 410                 415

Thr Val Lys Ile Gly Glu Lys Val His Glu Ile Gly Ile Ala Gly Lys
                420                 425                 430

Gln

<210> SEQ ID NO 93
<211> LENGTH: 443
<212> TYPE: PRT
<213> ORGANISM: Artificial Sequence
<220> FEATURE:
<223> OTHER INFORMATION: Synthetic Construct

<400> SEQUENCE: 93

Cys Val Ser Ala Val Ile Gly Ser Ala Ala Val Gly Ala Lys Ser Ala
  1               5                  10                  15

Val Asp Arg Arg Thr Thr Gly Ala Gln Thr Asp Asp Asn Val Met Ala
                 20                  25                  30

Leu Arg Ile Glu Thr Thr Ala Arg Ser Tyr Leu Arg Gln Asn Asn Gln
             35                  40                  45

Thr Lys Gly Tyr Thr Pro Gln Ile Ser Val Val Gly Tyr Asn Arg His
 50                  55                  60

Leu Leu Leu Leu Gly Gln Val Ala Thr Glu Gly Glu Lys Gln Phe Val
 65                  70                  75                  80

Gly Gln Ile Ala Arg Ser Glu Gln Ala Ala Glu Gly Val Tyr Asn Tyr
                 85                  90                  95

Ile Thr Val Ala Ser Leu Pro Arg Thr Ala Gly Asp Ile Ala Gly Asp
                100                 105                 110

Thr Trp Asn Thr Ser Lys Val Arg Ala Thr Leu Leu Gly Ile Ser Pro
            115                 120                 125

Ala Thr Gln Ala Arg Val Lys Ile Val Thr Tyr Gly Asn Val Thr Tyr
130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Pro Asp Ser Asp Arg Leu Gln Gln Arg
            180                 185                 190

Arg Val Ala Ala Asp Ile Gly Thr Gly Leu Ala Asp Ala Leu Thr Ala
        195                 200                 205

Pro Leu Asp His Lys Asp Lys Gly Leu Lys Ser Leu Thr Leu Glu Asp
210                 215                 220

Ser Ile Pro Gln Asn Gly Thr Leu Thr Leu Ser Ala Gln Gly Ala Glu
225                 230                 235                 240

Lys Thr Phe Lys Ala Gly Asp Lys Asp Asn Ser Leu Asn Thr Gly Lys
                245                 250                 255

Leu Lys Asn Asp Lys Ile Ser Arg Phe Asp Phe Val Gln Lys Ile Glu
            260                 265                 270

Val Asp Gly Gln Thr Ile Thr Leu Ala Ser Gly Glu Phe Gln Ile Tyr
        275                 280                 285

Lys Gln Asn His Ser Ala Val Val Ala Leu Gln Ile Glu Lys Ile Asn
290                 295                 300
```

Asn Pro Asp Lys Thr Asp Ser Leu Ile Asn Gln Arg Ser Phe Leu Val
305                 310                 315                 320

Ser Gly Leu Gly Gly Glu His Thr Ala Phe Asn Gln Leu Pro Gly Gly
            325                 330                 335

Lys Ala Glu Tyr His Gly Lys Ala Phe Ser Ser Asp Asp Pro Asn Gly
            340                 345                 350

Arg Leu His Tyr Ser Ile Asp Phe Thr Lys Lys Gln Gly Tyr Gly Arg
            355                 360                 365

Ile Glu His Leu Lys Thr Leu Glu Gln Asn Val Glu Leu Ala Ala Ala
370                 375                 380

Glu Leu Lys Ala Asp Glu Lys Ser His Ala Val Ile Leu Gly Asp Thr
385                 390                 395                 400

Arg Tyr Gly Ser Glu Glu Lys Gly Thr Tyr His Leu Ala Leu Phe Gly
            405                 410                 415

Asp Arg Ala Gln Glu Ile Ala Gly Ser Ala Thr Val Lys Ile Gly Glu
            420                 425                 430

Lys Val His Glu Ile Gly Ile Ala Gly Lys Gln
            435                 440

<210> SEQ ID NO 94
<211> LENGTH: 436
<212> TYPE: PRT
<213> ORGANISM: Artificial Sequence
<220> FEATURE:
<223> OTHER INFORMATION: Synthetic Construct

<400> SEQUENCE: 94

Cys Val Ser Ala Val Ile Gly Ser Ala Ala Val Gly Ala Lys Ser Ala
1               5                   10                  15

Val Asp Arg Arg Thr Thr Gly Ala Gln Thr Asp Asp Asn Val Met Ala
            20                  25                  30

Leu Arg Ile Glu Thr Thr Ala Arg Ser Tyr Leu Arg Gln Asn Asn Gln
            35                  40                  45

Thr Lys Gly Tyr Thr Pro Gln Ile Ser Val Val Gly Tyr Asn Arg His
50                  55                  60

Leu Leu Leu Leu Gly Gln Val Ala Thr Glu Gly Lys Gln Phe Val
65                  70                  75                  80

Gly Gln Ile Ala Arg Ser Glu Gln Ala Ala Glu Gly Val Tyr Asn Tyr
            85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
            115                 120                 125

Ala Thr Gln Ala Arg Val Lys Ile Val Thr Tyr Gly Asn Val Thr Tyr
            130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
            165                 170                 175

Tyr Val Gln Arg Gly Ser Gly Gly Gly Val Ala Ala Asp Ile Gly
            180                 185                 190

Thr Gly Leu Ala Asp Ala Leu Thr Ala Pro Leu Asp His Lys Asp Lys
            195                 200                 205

Gly Leu Lys Ser Leu Thr Leu Glu Asp Ser Ile Pro Gln Asn Gly Thr
            210                 215                 220

```
Leu Thr Leu Ser Ala Gln Gly Ala Glu Lys Thr Phe Lys Ala Gly Asp
225                 230                 235                 240

Lys Asp Asn Ser Leu Asn Thr Gly Lys Leu Lys Asn Asp Lys Ile Ser
            245                 250                 255

Arg Phe Asp Phe Val Gln Lys Ile Glu Val Asp Gly Gln Thr Ile Thr
        260                 265                 270

Leu Ala Ser Gly Glu Phe Gln Ile Tyr Lys Gln Asn His Ser Ala Val
    275                 280                 285

Val Ala Leu Gln Ile Glu Lys Ile Asn Asn Pro Asp Lys Thr Asp Ser
290                 295                 300

Leu Ile Asn Gln Arg Ser Phe Leu Val Ser Gly Leu Gly Gly Glu His
305                 310                 315                 320

Thr Ala Phe Asn Gln Leu Pro Gly Gly Lys Ala Glu Tyr His Gly Lys
            325                 330                 335

Ala Phe Ser Ser Asp Asp Pro Asn Gly Arg Leu His Tyr Ser Ile Asp
        340                 345                 350

Phe Thr Lys Lys Gln Gly Tyr Gly Arg Ile Glu His Leu Lys Thr Leu
    355                 360                 365

Glu Gln Asn Val Glu Leu Ala Ala Ala Glu Leu Lys Ala Asp Glu Lys
370                 375                 380

Ser His Ala Val Ile Leu Gly Asp Thr Arg Tyr Gly Ser Glu Glu Lys
385                 390                 395                 400

Gly Thr Tyr His Leu Ala Leu Phe Gly Asp Arg Ala Gln Glu Ile Ala
            405                 410                 415

Gly Ser Ala Thr Val Lys Ile Gly Glu Lys Val His Glu Ile Gly Ile
        420                 425                 430

Ala Gly Lys Gln
        435

<210> SEQ ID NO 95
<211> LENGTH: 26
<212> TYPE: DNA
<213> ORGANISM: Artificial Sequence
<220> FEATURE:
<223> OTHER INFORMATION: Synthetic Construct

<400> SEQUENCE: 95
cgcggatccg gccctgattc tgaccg                                        26

<210> SEQ ID NO 96
<211> LENGTH: 28
<212> TYPE: DNA
<213> ORGANISM: Artificial Sequence
<220> FEATURE:
<223> OTHER INFORMATION: Synthetic Construct

<400> SEQUENCE: 96
cccgctcgag ctgtttgccg gcgatgcc                                      28

<210> SEQ ID NO 97
<211> LENGTH: 25
<212> TYPE: DNA
<213> ORGANISM: Artificial Sequence
<220> FEATURE:
<223> OTHER INFORMATION: Synthetic Construct

<400> SEQUENCE: 97
cgcggatccg gaggggggtgg tgtcg                                        25
```

```
<210> SEQ ID NO 98
<211> LENGTH: 28
<212> TYPE: DNA
<213> ORGANISM: Artificial Sequence
<220> FEATURE:
<223> OTHER INFORMATION: Synthetic Construct

<400> SEQUENCE: 98
cccgctcgag ctgtttgccg gcgatgcc                                          28

<210> SEQ ID NO 99
<211> LENGTH: 26
<212> TYPE: DNA
<213> ORGANISM: Artificial Sequence
<220> FEATURE:
<223> OTHER INFORMATION: Synthetic Construct

<400> SEQUENCE: 99
cgcggatccg gccctgattc tgaccg                                            26

<210> SEQ ID NO 100
<211> LENGTH: 27
<212> TYPE: DNA
<213> ORGANISM: Artificial Sequence
<220> FEATURE:
<223> OTHER INFORMATION: Synthetic Construct

<400> SEQUENCE: 100
cccaagcttc tgtttgccgg cgatgcc                                           27

<210> SEQ ID NO 101
<211> LENGTH: 25
<212> TYPE: DNA
<213> ORGANISM: Artificial Sequence
<220> FEATURE:
<223> OTHER INFORMATION: Synthetic Construct

<400> SEQUENCE: 101
cgcggatccg gaggggtgg tgtcg                                              25

<210> SEQ ID NO 102
<211> LENGTH: 27
<212> TYPE: DNA
<213> ORGANISM: Artificial Sequence
<220> FEATURE:
<223> OTHER INFORMATION: Synthetic Construct

<400> SEQUENCE: 102
cccaagcttc tgtttgccgg cgatgcc                                           27

<210> SEQ ID NO 103
<211> LENGTH: 26
<212> TYPE: DNA
<213> ORGANISM: Artificial Sequence
<220> FEATURE:
<223> OTHER INFORMATION: Synthetic Construct

<400> SEQUENCE: 103
cgcggatccg gccctgattc tgaccg                                            26

<210> SEQ ID NO 104
<211> LENGTH: 27
<212> TYPE: DNA
<213> ORGANISM: Artificial Sequence
<220> FEATURE:
<223> OTHER INFORMATION: Synthetic Construct
```

```
<400> SEQUENCE: 104
cccaagcttc tgtttgccgg cgatgcc                                          27

<210> SEQ ID NO 105
<211> LENGTH: 25
<212> TYPE: DNA
<213> ORGANISM: Artificial Sequence
<220> FEATURE:
<223> OTHER INFORMATION: Synthetic Construct

<400> SEQUENCE: 105
cgcggatccg gaggggtgg tgtcg                                             25

<210> SEQ ID NO 106
<211> LENGTH: 27
<212> TYPE: DNA
<213> ORGANISM: Artificial Sequence
<220> FEATURE:
<223> OTHER INFORMATION: Synthetic Construct

<400> SEQUENCE: 106
cccaagcttc tgtttgccgg cgatgcc                                          27

<210> SEQ ID NO 107
<211> LENGTH: 26
<212> TYPE: DNA
<213> ORGANISM: Artificial Sequence
<220> FEATURE:
<223> OTHER INFORMATION: Synthetic Construct

<400> SEQUENCE: 107
cgcggatccg gccctgattc tgaccg                                           26

<210> SEQ ID NO 108
<211> LENGTH: 28
<212> TYPE: DNA
<213> ORGANISM: Artificial Sequence
<220> FEATURE:
<223> OTHER INFORMATION: Synthetic Construct

<400> SEQUENCE: 108
cccgctcgag ctgtttgccg gcgatgcc                                         28

<210> SEQ ID NO 109
<211> LENGTH: 25
<212> TYPE: DNA
<213> ORGANISM: Artificial Sequence
<220> FEATURE:
<223> OTHER INFORMATION: Synthetic Construct

<400> SEQUENCE: 109
cgcggatccg gaggggtgg tgtcg                                             25

<210> SEQ ID NO 110
<211> LENGTH: 28
<212> TYPE: DNA
<213> ORGANISM: Artificial Sequence
<220> FEATURE:
<223> OTHER INFORMATION: Synthetic Construct

<400> SEQUENCE: 110
cccgctcgag ctgtttgccg gcgatgcc                                         28

<210> SEQ ID NO 111
```

```
<211> LENGTH: 26
<212> TYPE: DNA
<213> ORGANISM: Artificial Sequence
<220> FEATURE:
<223> OTHER INFORMATION: Synthetic Construct

<400> SEQUENCE: 111
cgcggatccg gccctgattc tgaccg                                          26

<210> SEQ ID NO 112
<211> LENGTH: 28
<212> TYPE: DNA
<213> ORGANISM: Artificial Sequence
<220> FEATURE:
<223> OTHER INFORMATION: Synthetic Construct

<400> SEQUENCE: 112
cccgctcgag ctgtttgccg gcgatgcc                                        28

<210> SEQ ID NO 113
<211> LENGTH: 25
<212> TYPE: DNA
<213> ORGANISM: Artificial Sequence
<220> FEATURE:
<223> OTHER INFORMATION: Synthetic Construct

<400> SEQUENCE: 113
cgcggatccg gaggggtgg tgtcg                                            25

<210> SEQ ID NO 114
<211> LENGTH: 28
<212> TYPE: DNA
<213> ORGANISM: Artificial Sequence
<220> FEATURE:
<223> OTHER INFORMATION: Synthetic Construct

<400> SEQUENCE: 114
cccgctcgag ctgtttgccg gcgatgcc                                        28

<210> SEQ ID NO 115
<211> LENGTH: 26
<212> TYPE: DNA
<213> ORGANISM: Artificial Sequence
<220> FEATURE:
<223> OTHER INFORMATION: Synthetic Construct

<400> SEQUENCE: 115
cgcggatccg gccctgattc tgaccg                                          26

<210> SEQ ID NO 116
<211> LENGTH: 27
<212> TYPE: DNA
<213> ORGANISM: Artificial Sequence
<220> FEATURE:
<223> OTHER INFORMATION: Synthetic Construct

<400> SEQUENCE: 116
cccaagcttc tgtttgccgg cgatgcc                                         27

<210> SEQ ID NO 117
<211> LENGTH: 25
<212> TYPE: DNA
<213> ORGANISM: Artificial Sequence
<220> FEATURE:
<223> OTHER INFORMATION: Synthetic Construct

<400> SEQUENCE: 117
```
cgcggatccg gagggggtgg tgtcg                                         25

<210> SEQ ID NO 118
<211> LENGTH: 27
<212> TYPE: DNA
<213> ORGANISM: Artificial Sequence
<220> FEATURE:
<223> OTHER INFORMATION: Synthetic Construct

<400> SEQUENCE: 118
cccaagcttc tgtttgccgg cgatgcc                                       27

<210> SEQ ID NO 119
<211> LENGTH: 32
<212> TYPE: DNA
<213> ORGANISM: Artificial Sequence
<220> FEATURE:
<223> OTHER INFORMATION: Synthetic Construct

<400> SEQUENCE: 119
cgcggatccc atatgggccc tgattctgac cg                                 32

<210> SEQ ID NO 120
<211> LENGTH: 27
<212> TYPE: DNA
<213> ORGANISM: Artificial Sequence
<220> FEATURE:
<223> OTHER INFORMATION: Synthetic Construct

<400> SEQUENCE: 120
cgcggatccc tgtttgccgg cgatgcc                                       27

<210> SEQ ID NO 121
<211> LENGTH: 32
<212> TYPE: DNA
<213> ORGANISM: Artificial Sequence
<220> FEATURE:
<223> OTHER INFORMATION: Synthetic Construct

<400> SEQUENCE: 121
cgcggatccc atatgggccc tgattctgac cg                                 32

<210> SEQ ID NO 122
<211> LENGTH: 27
<212> TYPE: DNA
<213> ORGANISM: Artificial Sequence
<220> FEATURE:
<223> OTHER INFORMATION: Synthetic Construct

<400> SEQUENCE: 122
cgcggatccc tgtttgccgg cgatgcc                                       27

<210> SEQ ID NO 123
<211> LENGTH: 274
<212> TYPE: PRT
<213> ORGANISM: Neisseria meningitidis

<400> SEQUENCE: 123

Met Asn Arg Thr Ala Phe Cys Cys Leu Ser Leu Thr Ala Ala Leu Ile
 1               5                  10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

```
Ser Leu Gln Ser Leu Thr Leu Asp Gln Ser Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
                100                 105                 110

Gly Glu Phe Gln Val Tyr Lys Gln Ser His Ser Ala Leu Thr Ala Leu
            115                 120                 125

Gln Thr Glu Gln Val Gln Asp Ser Glu His Ser Gly Lys Met Val Ala
130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Ser Gly Lys Leu Thr Tyr Thr Ile Asp Phe Ala
                180                 185                 190

Ala Lys Gln Gly His Gly Lys Ile Glu His Leu Lys Ser Leu Glu Leu
            195                 200                 205

Asn Val Asp Leu Ala Ala Ser Asp Ile Lys Pro Asp Lys Lys Arg His
210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile Arg His Ile Gly Leu Ala Ala
                260                 265                 270

Lys Gln

<210> SEQ ID NO 124
<211> LENGTH: 274
<212> TYPE: PRT
<213> ORGANISM: Neisseria meningitidis

<400> SEQUENCE: 124

Met Asn Arg Thr Ala Phe Cys Cys Phe Ser Leu Thr Ala Ala Leu Ile
 1               5                  10                  15

Leu Thr Ala Cys Ser Ser Gly Gly Gly Val Ala Ala Asp Ile Gly
                 20                  25                  30

Ala Gly Leu Ala Asp Ala Leu Thr Ala Pro Leu Asp His Lys Asp Lys
             35                  40                  45

Ser Leu Gln Ser Leu Thr Leu Asp Gln Ser Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
                100                 105                 110

Gly Glu Phe Gln Ile Tyr Lys Gln Asp His Ser Ala Leu Thr Ala Leu
            115                 120                 125

Gln Thr Glu Gln Glu Gln Asp Pro Glu His Ser Gly Lys Met Val Ala
130                 135                 140
```

```
Lys Arg Arg Phe Lys Ile Gly Asp Ile Ala Gly Glu His Thr Ser Phe
145                 150                 155                 160

Asp Lys Leu Pro Lys Asp Val Met Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly His Gly Lys Ile Glu His Leu Lys Ser Pro Glu Leu
        195                 200                 205

Asn Val Glu Leu Ala Thr Ala Tyr Ile Lys Pro Asp Glu Lys His His
    210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Glu Thr Ala Asn Gly Ile His His Ile Gly Leu Ala Ala
            260                 265                 270

Lys Gln

<210> SEQ ID NO 125
<211> LENGTH: 274
<212> TYPE: PRT
<213> ORGANISM: Neisseria meningitidis

<400> SEQUENCE: 125

Met Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Met Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Val Gln Asp Ser Glu Asp Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Lys Asp Val Met Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly His Gly Lys Ile Glu His Leu Lys Ser Pro Glu Leu
        195                 200                 205

Asn Val Glu Leu Ala Ala Ala Tyr Ile Lys Pro Asp Glu Lys His His
    210                 215                 220

Ala Val Ile Ser Gly Ser Val Leu Tyr Asn Gln Asp Glu Lys Gly Ser
225                 230                 235                 240
```

```
Tyr Ser Leu Gly Ile Phe Gly Gly Gln Ala Gln Glu Val Ala Gly Ser
                245                 250                 255

Ala Glu Val Glu Thr Ala Asn Gly Ile Gln His Ile Gly Leu Ala Ala
            260                 265                 270

Lys Gln

<210> SEQ ID NO 126
<211> LENGTH: 274
<212> TYPE: PRT
<213> ORGANISM: Neisseria meningitidis

<400> SEQUENCE: 126

Met Asn Arg Thr Thr Phe Cys Cys Leu Ser Leu Thr Ala Ala Leu Ile
 1               5                  10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asn Gly Gln Leu Ile Thr Leu Glu Ser
            100                 105                 110

Gly Glu Phe Gln Val Tyr Lys Gln Ser His Ser Ala Leu Thr Ala Leu
        115                 120                 125

Gln Thr Glu Gln Val Gln Asp Ser Glu His Ser Arg Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Lys Gly Asp Ser Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Tyr Gly Lys Ile Glu His Leu Lys Ser Pro Glu Leu
        195                 200                 205

Asn Val Asp Leu Ala Ala Ala Tyr Ile Lys Pro Asp Glu Lys His His
    210                 215                 220

Ala Val Ile Ser Gly Ser Val Leu Tyr Asn Gln Asp Glu Lys Gly Ser
225                 230                 235                 240

Tyr Ser Leu Gly Ile Phe Gly Gly Gln Ala Gln Glu Val Ala Gly Ser
                245                 250                 255

Ala Glu Val Lys Thr Ala Asn Gly Ile Arg His Ile Gly Leu Ala Ala
            260                 265                 270

Lys Gln

<210> SEQ ID NO 127
<211> LENGTH: 274
<212> TYPE: PRT
<213> ORGANISM: Neisseria meningitidis

<400> SEQUENCE: 127

Met Asn Arg Thr Ala Phe Cys Cys Leu Ser Leu Thr Ala Ala Leu Ile
```

```
            1               5                  10                 15
Leu Thr Ala Cys Ser Ser Gly Gly Gly Val Ala Ala Asp Ile Gly
                    20                  25                 30
Ala Gly Leu Ala Asp Ala Leu Thr Ala Pro Leu Asp His Lys Asp Lys
                35                  40                  45
Ser Leu Gln Ser Leu Thr Leu Asp Gln Ser Val Arg Lys Asn Glu Lys
            50                  55                  60
Leu Lys Leu Ala Ala Gln Gly Ala Glu Lys Thr Tyr Gly Asn Gly Asp
65                  70                  75                  80
Ser Leu Asn Thr Gly Lys Leu Lys Asn Asp Lys Val Ser Arg Phe Asp
                    85                  90                  95
Phe Ile Arg Gln Ile Glu Val Asp Gly Gln Leu Ile Thr Leu Glu Ser
                100                 105                 110
Gly Glu Phe Gln Val Tyr Lys Gln Ser His Ser Ala Leu Thr Ala Phe
            115                 120                 125
Gln Thr Glu Gln Ile Gln Asp Ser Glu His Ser Gly Lys Met Val Ala
        130                 135                 140
Lys Arg Gln Phe Arg Ile Gly Asp Ile Ala Gly Glu His Thr Ser Phe
145                 150                 155                 160
Asp Lys Leu Pro Glu Gly Gly Arg Ala Thr Tyr Arg Gly Thr Ala Phe
                    165                 170                 175
Gly Ser Asp Asp Ala Gly Gly Lys Leu Thr Tyr Thr Ile Asp Phe Ala
                180                 185                 190
Ala Lys Gln Gly Asn Gly Lys Ile Glu His Leu Lys Ser Pro Glu Leu
            195                 200                 205
Asn Val Asp Leu Ala Ala Ala Asp Ile Lys Pro Asp Gly Lys Arg His
        210                 215                 220
Ala Val Ile Ser Gly Ser Val Leu Tyr Asn Gln Ala Glu Lys Gly Ser
225                 230                 235                 240
Tyr Ser Leu Gly Ile Phe Gly Gly Lys Ala Gln Glu Val Ala Gly Ser
                    245                 250                 255
Ala Glu Val Lys Thr Val Asn Gly Ile Arg His Ile Gly Leu Ala Ala
                260                 265                 270
Lys Gln

<210> SEQ ID NO 128
<211> LENGTH: 274
<212> TYPE: PRT
<213> ORGANISM: Neisseria meningitidis

<400> SEQUENCE: 128

Met Asn Arg Thr Ala Phe Cys Cys Leu Ser Leu Thr Thr Ala Leu Ile
1               5                   10                  15
Leu Thr Ala Cys Ser Ser Gly Gly Gly Val Thr Ala Asp Ile Gly
                    20                  25                  30
Thr Gly Leu Ala Asp Ala Leu Thr Ala Pro Leu Asp His Lys Asp Lys
                35                  40                  45
Gly Leu Lys Ser Leu Thr Leu Glu Asp Ser Ile Ser Gln Asn Gly Thr
            50                  55                  60
Leu Thr Leu Ser Ala Gln Gly Ala Glu Lys Thr Tyr Gly Asn Gly Asp
65                  70                  75                  80
Ser Leu Asn Thr Gly Lys Leu Lys Asn Asp Lys Val Ser Arg Phe Asp
                    85                  90                  95
Phe Ile Arg Gln Ile Glu Val Asp Gly Lys Leu Ile Thr Leu Glu Ser
```

```
            100                 105                 110
Gly Glu Phe Gln Val Tyr Lys Gln Ser His Ser Ala Leu Thr Ala Leu
            115                 120                 125
Gln Thr Glu Gln Val Gln Asp Ser Glu Asp Ser Gly Lys Met Val Ala
        130                 135                 140
Lys Arg Gln Phe Arg Ile Gly Asp Ile Ala Gly Glu His Thr Ser Phe
145                 150                 155                 160
Asp Lys Leu Pro Lys Gly Gly Ser Ala Thr Tyr Arg Gly Thr Ala Phe
                165                 170                 175
Gly Ser Asp Asp Ala Gly Gly Lys Leu Thr Tyr Thr Ile Asp Phe Ala
            180                 185                 190
Ala Lys Gln Gly His Gly Lys Ile Glu His Leu Lys Ser Pro Glu Leu
            195                 200                 205
Asn Val Glu Leu Ala Thr Ala Tyr Ile Lys Pro Asp Glu Lys His His
        210                 215                 220
Ala Val Ile Ser Gly Ser Val Leu Tyr Asn Gln Asp Glu Lys Gly Ser
225                 230                 235                 240
Tyr Ser Leu Gly Ile Phe Gly Gly Gln Ala Gln Glu Val Ala Gly Ser
                245                 250                 255
Ala Glu Val Glu Thr Ala Asn Gly Ile His His Ile Gly Leu Ala Ala
            260                 265                 270
Lys Gln

<210> SEQ ID NO 129
<211> LENGTH: 274
<212> TYPE: PRT
<213> ORGANISM: Neisseria meningitidis

<400> SEQUENCE: 129

Met Asn Arg Thr Ala Phe Cys Cys Phe Ser Leu Thr Ala Ala Leu Ile
1               5                   10                  15
Leu Thr Ala Cys Ser Ser Gly Gly Gly Val Ala Ala Asp Ile Gly
            20                  25                  30
Ala Gly Leu Ala Asp Ala Leu Thr Ala Pro Leu Asp His Lys Asp Lys
        35                  40                  45
Gly Leu Gln Ser Leu Thr Leu Asp Gln Ser Val Arg Lys Asn Glu Lys
    50                  55                  60
Leu Lys Leu Ala Ala Gln Gly Ala Glu Lys Thr Tyr Gly Asn Gly Asp
65                  70                  75                  80
Ser Leu Asn Thr Gly Lys Leu Lys Asn Asp Lys Val Ser Arg Phe Asp
                85                  90                  95
Phe Ile Arg Gln Ile Glu Val Asp Gly Lys Leu Ile Thr Leu Glu Ser
            100                 105                 110
Gly Glu Phe Gln Val Tyr Lys Gln Ser His Ser Ala Leu Thr Ala Leu
            115                 120                 125
Gln Thr Glu Gln Val Gln Asp Ser Glu Asp Ser Gly Lys Met Val Ala
        130                 135                 140
Lys Arg Gln Phe Arg Ile Gly Asp Ile Ala Gly Glu His Thr Ser Phe
145                 150                 155                 160
Asp Lys Leu Pro Lys Gly Gly Ser Ala Thr Tyr Arg Gly Thr Ala Phe
                165                 170                 175
Gly Ser Asp Asp Ala Gly Gly Lys Leu Thr Tyr Thr Ile Asp Phe Ala
            180                 185                 190
Ala Lys Gln Gly His Gly Lys Ile Glu His Leu Lys Ser Pro Glu Leu
```

```
                195                 200                 205
Asn Val Glu Leu Ala Thr Ala Tyr Ile Lys Pro Asp Glu Lys Arg His
    210                 215                 220
Ala Val Ile Ser Gly Ser Val Leu Tyr Asn Gln Asp Glu Lys Gly Ser
225                 230                 235                 240
Tyr Ser Leu Gly Ile Phe Gly Gly Gln Ala Gln Glu Val Ala Gly Ser
                245                 250                 255
Ala Glu Val Glu Thr Ala Asn Gly Ile His His Ile Gly Leu Ala Ala
    260                 265                 270
Lys Gln

<210> SEQ ID NO 130
<211> LENGTH: 274
<212> TYPE: PRT
<213> ORGANISM: Neisseria meningitidis

<400> SEQUENCE: 130

Met Asn Arg Thr Ala Phe Cys Cys Leu Ser Leu Thr Ala Ala Leu Ile
1               5                   10                  15
Leu Thr Ala Cys Ser Ser Gly Gly Gly Val Ala Ala Asp Ile Gly
            20                  25                  30
Ala Gly Leu Ala Asp Ala Leu Thr Ala Pro Leu Asp His Lys Asp Lys
        35                  40                  45
Gly Leu Gln Ser Leu Thr Leu Asp Gln Ser Val Arg Lys Asn Glu Lys
    50                  55                  60
Leu Lys Leu Ala Ala Gln Gly Ala Glu Lys Thr Tyr Gly Asn Gly Asp
65                  70                  75                  80
Ser Leu Asn Thr Gly Lys Leu Lys Asn Asp Lys Val Ser Arg Phe Asp
                85                  90                  95
Phe Ile Arg Gln Ile Glu Val Asp Gly Gln Leu Ile Thr Leu Glu Ser
            100                 105                 110
Gly Glu Phe Gln Val Tyr Lys Gln Ser His Ser Ala Leu Thr Ala Leu
        115                 120                 125
Gln Thr Glu Gln Val Gln Asp Ser Glu Asp Ser Gly Lys Met Val Ala
    130                 135                 140
Lys Arg Gln Phe Arg Ile Gly Asp Ile Ala Gly Glu His Thr Ser Phe
145                 150                 155                 160
Asp Lys Leu Pro Lys Gly Gly Ser Ala Thr Tyr Arg Gly Thr Ala Phe
                165                 170                 175
Ser Ser Asp Asp Ala Gly Gly Lys Leu Thr Tyr Thr Ile Asp Phe Ala
            180                 185                 190
Ala Lys Gln Gly His Gly Lys Ile Glu His Leu Lys Ser Pro Glu Leu
        195                 200                 205
Asn Val Glu Leu Ala Thr Ala Tyr Ile Lys Pro Asp Glu Lys Arg His
    210                 215                 220
Ala Val Ile Ser Gly Ser Val Leu Tyr Asn Gln Asp Glu Lys Gly Ser
225                 230                 235                 240
Tyr Ser Leu Gly Ile Phe Gly Gly Gln Ala Gln Glu Val Ala Gly Ser
                245                 250                 255
Ala Glu Val Glu Thr Ala Asn Gly Ile Gln His Ile Gly Leu Ala Ala
            260                 265                 270
Lys Gln

<210> SEQ ID NO 131
```

```
<211> LENGTH: 273
<212> TYPE: PRT
<213> ORGANISM: Neisseria meningitidis

<400> SEQUENCE: 131

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
130                 135                 140

Gln Arg Ser Phe Leu Val Ser Gly Leu Gly Gly Glu His Thr Ala Phe
145                 150                 155                 160

Asn Gln Leu Pro Val Asp Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ser Ala Glu Leu Lys Ala Asp Glu Lys Ser His Ala
210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 132
<211> LENGTH: 273
<212> TYPE: PRT
<213> ORGANISM: Neisseria meningitidis

<400> SEQUENCE: 132

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Arg Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
50                  55                  60
```

```
Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
            130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
            195                 200                 205

Val Glu Leu Ala Ala Ala Glu Leu Lys Ala Asp Glu Lys Ser His Ala
210                 215                 220

Val Ile Leu Gly Asp Thr Arg Tyr Gly Ser Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 133
<211> LENGTH: 273
<212> TYPE: PRT
<213> ORGANISM: Neisseria meningitidis

<400> SEQUENCE: 133

Met Asn Arg Thr Ala Phe Cys Cys Leu Ser Leu Thr Thr Ala Leu Ile
  1               5                  10                  15

Leu Thr Ala Cys Ser Ser Gly Gly Gly Val Ala Ala Asp Ile Gly
                 20                  25                  30

Ala Gly Leu Ala Asp Ala Leu Thr Ala Pro Leu Asp His Lys Asp Lys
             35                  40                  45

Ser Leu Gln Ser Leu Thr Leu Asp Gln Ser Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
            130                 135                 140

Gln Arg Ser Phe Leu Val Ser Gly Leu Gly Gly Glu His Thr Ala Phe
145                 150                 155                 160
```

```
Asn Gln Leu Pro Gly Gly Lys Ala Glu Tyr His Gly Lys Ala Phe Ser
            165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
            195                 200                 205

Val Glu Leu Ala Ala Ala Glu Leu Lys Ala Asp Glu Lys Ser His Ala
            210                 215                 220

Val Ile Leu Gly Asp Thr Arg Tyr Gly Ser Glu Lys Gly Thr Tyr
225                 230                 235                 240

His Leu Ala Leu Phe Gly Asp Arg Ala Gln Glu Ile Ala Gly Ser Ala
            245                 250                 255

Thr Val Lys Ile Gly Glu Lys Val His Glu Ile Gly Ile Ala Gly Lys
            260                 265                 270

Gln

<210> SEQ ID NO 134
<211> LENGTH: 273
<212> TYPE: PRT
<213> ORGANISM: Neisseria meningitidis

<400> SEQUENCE: 134

Met Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
            35                  40                  45

Gly Leu Gln Ser Leu Thr Leu Asp Gln Ser Val Arg Lys Asn Glu Lys
        50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
            85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
            165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
            195                 200                 205

Val Glu Leu Ala Ala Ala Glu Leu Lys Ala Asp Glu Lys Ser His Ala
            210                 215                 220

Val Ile Leu Gly Asp Thr Arg Tyr Gly Ser Glu Lys Gly Thr Tyr
225                 230                 235                 240

His Leu Ala Leu Phe Gly Asp Arg Ala Gln Glu Ile Ala Gly Ser Ala
            245                 250                 255
```

Thr Val Lys Ile Gly Glu Lys Val His Glu Ile Gly Ile Ala Gly Lys
            260                 265                 270
Gln

<210> SEQ ID NO 135
<211> LENGTH: 273
<212> TYPE: PRT
<213> ORGANISM: Neisseria meningitidis

<400> SEQUENCE: 135

Met Asn Arg Thr Ala Phe Cys Cys Leu Ser Leu Thr Ala Leu Ile
 1               5                  10                  15

Leu Thr Ala Cys Ser Ser Gly Gly Gly Val Ala Ala Asp Ile Gly
                20                  25                  30

Thr Gly Leu Ala Asp Ala Leu Thr Ala Pro Leu Asp His Lys Asp Lys
            35                  40                  45

Gly Leu Gln Ser Leu Thr Leu Asp Gln Ser Val Arg Lys Asn Glu Lys
        50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
                100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
        130                 135                 140

Gln Arg Ser Phe Leu Val Ser Gly Leu Gly Gly Glu His Thr Ala Phe
145                 150                 155                 160

Asn Gln Leu Pro Ser Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
                180                 185                 190

Lys Gln Gly His Gly Lys Ile Glu His Leu Lys Thr Pro Glu Gln Asn
            195                 200                 205

Val Glu Leu Ala Ser Ala Glu Leu Lys Ala Asp Glu Lys Ser His Ala
        210                 215                 220

Val Ile Leu Gly Asp Thr Arg Tyr Gly Gly Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
            260                 265                 270
Gln

<210> SEQ ID NO 136
<211> LENGTH: 273
<212> TYPE: PRT
<213> ORGANISM: Neisseria meningitidis

<400> SEQUENCE: 136

Met Asn Arg Thr Ala Phe Cys Cys Leu Ser Leu Thr Ala Ala Leu Ile
 1               5                  10                  15

Leu Thr Ala Cys Ser Ser Gly Gly Gly Gly Val Ala Ala Asp Ile Gly
                20                  25                  30

Ala Gly Leu Ala Asp Ala Leu Thr Ala Pro Leu Asp His Lys Asp Lys
            35                  40                  45

Ser Leu Gln Ser Leu Thr Leu Asp Gln Ser Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
130                 135                 140

Gln Arg Ser Phe Leu Val Ser Gly Leu Gly Gly Glu His Thr Ala Phe
145                 150                 155                 160

Asn Gln Leu Pro Ser Gly Lys Ala Glu Tyr His Gly Lys Ala Phe Ser
                165                 170                 175

Phe Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
            195                 200                 205

Val Glu Leu Ala Ser Ala Glu Leu Lys Ala Asp Glu Lys Ser His Ala
210                 215                 220

Val Ile Leu Gly Asp Thr Arg Tyr Gly Gly Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
            260                 265                 270

Gln

<210> SEQ ID NO 137
<211> LENGTH: 273
<212> TYPE: PRT
<213> ORGANISM: Neisseria meningitidis

<400> SEQUENCE: 137

Met Asn Arg Thr Ala Phe Cys Cys Phe Ser Leu Thr Ala Ala Leu Ile
 1               5                  10                  15

Leu Thr Ala Cys Ser Ser Gly Gly Gly Val Ala Ala Asp Ile Gly
                20                  25                  30

Ala Gly Leu Ala Asp Ala Leu Thr Ala Pro Leu Asp His Lys Asp Lys
            35                  40                  45

Gly Leu Gln Ser Leu Thr Leu Asp Gln Ser Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
            115                 120                 125

```
Gln Ile Glu Lys Ile Asn Asn Pro Asp Lys Ile Asp Ser Leu Ile Asn
            130                 135                 140

Gln Arg Ser Phe Leu Val Ser Gly Leu Gly Gly Glu His Thr Ala Phe
145                 150                 155                 160

Asn Gln Leu Pro Ser Gly Lys Ala Glu Tyr His Gly Lys Ala Phe Ser
                165                 170                 175

Ser Asp Asp Pro Asn Gly Arg Leu His Tyr Ser Ile Asp Phe Thr Lys
            180                 185                 190

Lys Gln Gly Tyr Gly Arg Ile Glu His Leu Lys Thr Pro Glu Gln Asn
                195                 200                 205

Val Glu Leu Ala Ser Ala Glu Leu Lys Ala Asp Glu Lys Ser His Ala
            210                 215                 220

Val Ile Leu Gly Asp Thr Arg Tyr Gly Gly Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Arg Glu Lys Val His Glu Ile Gly Ile Ala Gly Lys
            260                 265                 270

Gln

<210> SEQ ID NO 138
<211> LENGTH: 281
<212> TYPE: PRT
<213> ORGANISM: Neisseria meningitidis

<400> SEQUENCE: 138

Met Asn Arg Thr Thr Phe Cys Cys Leu Ser Leu Thr Ala Ala Leu Ile
1               5                   10                  15

Leu Thr Ala Cys Ser Ser Gly Gly Gly Ser Gly Gly Gly Gly Gly Val
            20                  25                  30

Ala Ala Asp Ile Gly Thr Gly Leu Ala Asp Ala Leu Thr Ala Pro Leu
        35                  40                  45

Asp His Lys Asp Lys Gly Leu Lys Ser Leu Thr Leu Glu Asp Ser Ile
    50                  55                  60

Pro Gln Asn Gly Thr Leu Thr Leu Ser Ala Gln Gly Ala Glu Lys Thr
65                  70                  75                  80

Phe Lys Ala Gly Asp Lys Asp Asn Ser Leu Asn Thr Gly Lys Leu Lys
                85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
        115                 120                 125

Asn His Ser Ala Val Val Ala Leu Gln Ile Glu Lys Ile Asn Asn Pro
    130                 135                 140

Asp Lys Ile Asp Ser Leu Ile Asn Gln Arg Ser Phe Leu Val Ser Gly
145                 150                 155                 160

Leu Gly Gly Glu His Thr Ala Phe Asn Gln Leu Pro Gly Asp Lys Ala
                165                 170                 175

Glu Tyr His Gly Lys Ala Phe Ser Ser Asp Pro Asn Gly Arg Leu
            180                 185                 190

His Tyr Thr Ile Asp Phe Thr Asn Lys Gln Gly Tyr Gly Arg Ile Glu
        195                 200                 205

His Leu Lys Thr Pro Glu Leu Asn Val Asp Leu Ala Ser Ala Glu Leu
    210                 215                 220
```

```
Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
            245                 250                 255

Ala Gln Glu Ile Ala Gly Ser Ala Thr Val Lys Ile Gly Glu Lys Val
        260                 265                 270

His Glu Ile Gly Ile Ala Gly Lys Gln
    275                 280

<210> SEQ ID NO 139
<211> LENGTH: 250
<212> TYPE: PRT
<213> ORGANISM: Neisseria meningitidis

<400> SEQUENCE: 139

Met Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
        115                 120                 125

Gln Thr Glu Gln Ile Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu
        195                 200                 205

Asn Val Asp Leu Ala Ala Ala Asp Ile Lys Pro Asp Gly Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala
                245                 250

<210> SEQ ID NO 140
<211> LENGTH: 282
<212> TYPE: PRT
<213> ORGANISM: Neisseria meningitidis

<400> SEQUENCE: 140

Met Asn Arg Thr Thr Phe Cys Cys Leu Ser Leu Thr Ala Ala Leu Ile
1               5                   10                  15
```

```
Leu Thr Ala Cys Ser Ser Gly Gly Gly Ser Gly Gly Gly Gly Val
            20                  25                  30

Ala Ala Asp Ile Gly Ala Gly Leu Ala Asp Ala Leu Thr Ala Pro Leu
            35                  40                  45

Asp His Lys Asp Lys Gly Leu Lys Ser Leu Thr Leu Glu Asp Ser Ile
 50                  55                  60

Ser Gln Asn Gly Thr Leu Thr Leu Ser Ala Gln Gly Ala Glu Arg Thr
 65                  70                  75                  80

Phe Lys Ala Gly Asp Lys Asp Asn Ser Leu Asn Thr Gly Lys Leu Lys
                85                  90                  95

Asn Asp Lys Ile Ser Arg Phe Asp Phe Ile Arg Gln Ile Glu Val Asp
            100                 105                 110

Gly Gln Leu Ile Thr Leu Glu Ser Gly Glu Phe Gln Val Tyr Lys Gln
            115                 120                 125

Ser His Ser Ala Leu Thr Ala Leu Gln Thr Glu Gln Val Gln Asp Ser
            130                 135                 140

Glu His Ser Gly Lys Met Val Ala Lys Arg Gln Phe Arg Ile Gly Asp
145                 150                 155                 160

Ile Val Gly Glu His Thr Ser Phe Gly Lys Leu Pro Lys Asp Val Met
                165                 170                 175

Ala Thr Tyr Arg Gly Thr Ala Phe Gly Ser Asp Asp Ala Gly Gly Lys
            180                 185                 190

Leu Thr Tyr Thr Ile Asp Phe Ala Ala Lys Gln Gly His Gly Lys Ile
            195                 200                 205

Glu His Leu Lys Ser Pro Glu Leu Asn Val Asp Leu Ala Ala Ala Asp
            210                 215                 220

Ile Lys Pro Asp Glu Lys His His Ala Val Ile Ser Gly Ser Val Leu
225                 230                 235                 240

Tyr Asn Gln Ala Glu Lys Gly Ser Tyr Ser Leu Gly Ile Phe Gly Gly
                245                 250                 255

Gln Ala Gln Glu Val Ala Gly Ser Ala Glu Val Glu Thr Ala Asn Gly
            260                 265                 270

Ile Arg His Ile Gly Leu Ala Ala Lys Gln
            275                 280

<210> SEQ ID NO 141
<211> LENGTH: 275
<212> TYPE: PRT
<213> ORGANISM: Neisseria meningitidis

<400> SEQUENCE: 141

Met Asn Arg Thr Ala Phe Cys Cys Leu Ser Leu Thr Ala Ala Leu Ile
 1               5                  10                  15

Leu Thr Ala Cys Ser Ser Gly Ser Gly Gly Gly Val Ala Ala Asp
            20                  25                  30

Ile Gly Thr Gly Leu Ala Tyr Ala Leu Thr Ala Pro Leu Asp His Lys
            35                  40                  45

Asp Lys Ser Leu Gln Ser Leu Thr Leu Asp Gln Ser Val Arg Lys Asn
 50                  55                  60

Glu Lys Leu Lys Leu Ala Ala Gln Gly Ala Lys Thr Tyr Gly Asn
 65                  70                  75                  80

Gly Asp Ser Leu Asn Thr Gly Lys Leu Lys Asn Asp Lys Val Ser Arg
                85                  90                  95

Phe Asp Phe Ile Arg Gln Ile Glu Val Asp Gly Gln Leu Ile Thr Leu
```

```
              100                 105                 110
Glu Ser Gly Glu Phe Gln Ile Tyr Lys Gln Asp His Ser Ala Val Val
            115                 120                 125

Ala Leu Gln Ile Glu Lys Ile Asn Asn Pro Asp Lys Ile Asp Ser Leu
        130                 135                 140

Ile Asn Gln Arg Ser Phe Leu Val Ser Gly Leu Gly Gly Glu His Thr
145                 150                 155                 160

Ala Phe Asn Gln Leu Pro Gly Gly Lys Ala Glu Tyr His Gly Lys Ala
                165                 170                 175

Phe Ser Ser Asp Asp Pro Asn Gly Arg Leu His Tyr Ser Ile Asp Phe
                180                 185                 190

Thr Lys Lys Gln Gly Tyr Gly Arg Ile Glu His Leu Lys Thr Pro Glu
            195                 200                 205

Gln Asn Val Glu Leu Ala Ser Ala Glu Leu Lys Ala Asp Glu Lys Ser
        210                 215                 220

His Ala Val Ile Leu Gly Asp Thr Arg Tyr Gly Gly Glu Lys Gly
225                 230                 235                 240

Thr Tyr His Leu Ala Leu Phe Gly Asp Arg Ala Gln Glu Ile Ala Gly
                245                 250                 255

Ser Ala Thr Val Lys Ile Arg Glu Lys Val His Glu Ile Gly Ile Ala
                260                 265                 270

Gly Lys Gln
        275

<210> SEQ ID NO 142
<211> LENGTH: 757
<212> TYPE: PRT
<213> ORGANISM: Artificial Sequence
<220> FEATURE:
<223> OTHER INFORMATION: Synthetic Construct

<400> SEQUENCE: 142

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
```

```
            180                 185                 190
Pro Asp Gly Lys Arg His Ala Val Ile Ser Gly Ser Val Leu Tyr Asn
            195                 200                 205
Gln Ala Glu Lys Gly Ser Tyr Ser Leu Gly Ile Phe Gly Gly Lys Ala
            210                 215                 220
Gln Glu Val Ala Gly Ser Ala Glu Val Lys Thr Val Asn Gly Ile Arg
225                 230                 235                 240
His Ile Gly Leu Ala Ala Lys Gln Gly Ser Gly Gly Gly Val Ala
                    245                 250                 255
Ala Asp Ile Gly Ala Gly Leu Ala Asp Ala Leu Thr Ala Pro Leu Asp
                    260                 265                 270
His Lys Asp Lys Ser Leu Gln Ser Leu Thr Leu Asp Gln Ser Val Arg
            275                 280                 285
Lys Asn Glu Lys Leu Lys Leu Ala Ala Gln Gly Ala Glu Lys Thr Tyr
            290                 295                 300
Gly Asn Gly Asp Ser Leu Asn Thr Gly Lys Leu Lys Asn Asp Lys Val
305                 310                 315                 320
Ser Arg Phe Asp Phe Ile Arg Gln Ile Glu Val Asp Gly Gln Leu Ile
                    325                 330                 335
Thr Leu Glu Ser Gly Glu Phe Gln Ile Tyr Lys Gln Asp His Ser Ala
                    340                 345                 350
Val Val Ala Leu Gln Ile Glu Lys Ile Asn Asn Pro Asp Lys Ile Asp
                    355                 360                 365
Ser Leu Ile Asn Gln Arg Ser Phe Leu Val Ser Gly Leu Gly Gly Glu
            370                 375                 380
His Thr Ala Phe Asn Gln Leu Pro Asp Gly Lys Ala Glu Tyr His Gly
385                 390                 395                 400
Lys Ala Phe Ser Ser Asp Ala Gly Gly Lys Leu Tyr Thr Ile
                    405                 410                 415
Asp Phe Ala Ala Lys Gln Gly His Gly Lys Ile Glu His Leu Lys Thr
                    420                 425                 430
Pro Glu Gln Asn Val Glu Leu Ala Ala Ala Glu Leu Lys Ala Asp Glu
            435                 440                 445
Lys Ser His Ala Val Ile Leu Gly Asp Thr Arg Tyr Gly Ser Glu Glu
            450                 455                 460
Lys Gly Thr Tyr His Leu Ala Leu Phe Gly Asp Arg Ala Gln Glu Ile
465                 470                 475                 480
Ala Gly Ser Ala Thr Val Lys Ile Gly Glu Lys Val His Glu Ile Gly
                    485                 490                 495
Ile Ala Gly Lys Gln Gly Ser Gly Gly Gly Val Ala Ala Asp Ile
                    500                 505                 510
Gly Thr Gly Leu Ala Asp Ala Leu Thr Ala Pro Leu Asp His Lys Asp
            515                 520                 525
Lys Gly Leu Lys Ser Leu Thr Leu Glu Asp Ser Ile Pro Gln Asn Gly
            530                 535                 540
Thr Leu Thr Leu Ser Ala Gln Gly Ala Glu Lys Thr Phe Lys Ala Gly
545                 550                 555                 560
Asp Lys Asp Asn Ser Leu Asn Thr Gly Lys Leu Lys Asn Asp Lys Ile
                    565                 570                 575
Ser Arg Phe Asp Phe Val Gln Lys Ile Glu Val Asp Gly Gln Thr Ile
                    580                 585                 590
Thr Leu Ala Ser Gly Glu Phe Gln Ile Tyr Lys Gln Asn His Ser Ala
            595                 600                 605
```

```
Val Val Ala Leu Gln Ile Glu Lys Ile Asn Asn Pro Asp Lys Thr Asp
    610                 615                 620

Ser Leu Ile Asn Gln Arg Ser Phe Leu Val Ser Gly Leu Gly Gly Glu
625                 630                 635                 640

His Thr Ala Phe Asn Gln Leu Pro Gly Gly Lys Ala Glu Tyr His Gly
                645                 650                 655

Lys Ala Phe Ser Ser Asp Asp Pro Asn Gly Arg Leu His Tyr Ser Ile
                660                 665                 670

Asp Phe Thr Lys Lys Gln Gly Tyr Gly Arg Ile Glu His Leu Lys Thr
                675                 680                 685

Leu Glu Gln Asn Val Glu Leu Ala Ala Ala Glu Leu Lys Ala Asp Glu
                690                 695                 700

Lys Ser His Ala Val Ile Leu Gly Asp Thr Arg Tyr Gly Ser Glu Glu
705                 710                 715                 720

Lys Gly Thr Tyr His Leu Ala Leu Phe Gly Asp Arg Ala Gln Glu Ile
                725                 730                 735

Ala Gly Ser Ala Thr Val Lys Ile Gly Glu Lys Val His Glu Ile Gly
                740                 745                 750

Ile Ala Gly Lys Gln
        755
```

<210> SEQ ID NO 143
<211> LENGTH: 405
<212> TYPE: PRT
<213> ORGANISM: Neisseria meningitidis

<400> SEQUENCE: 143

```
Met Lys His Phe Pro Ser Lys Val Leu Thr Thr Ala Ile Leu Ala Thr
 1               5                  10                  15

Phe Cys Ser Gly Ala Leu Ala Ala Thr Asn Asp Asp Val Lys Lys
                20                  25                  30

Ala Ala Thr Val Ala Ile Ala Ala Tyr Asn Asn Gly Gln Glu Ile
                35                  40                  45

Asn Gly Phe Lys Ala Gly Glu Thr Ile Tyr Asp Ile Asp Glu Asp Gly
 50                  55                  60

Thr Ile Thr Lys Lys Asp Ala Thr Ala Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
                100                 105                 110

Ser Glu Ile Glu Lys Leu Thr Thr Lys Leu Ala Asp Thr Asp Ala Ala
                115                 120                 125

Leu Ala Asp Thr Asp Ala Ala Leu Asp Ala Thr Thr Asn Ala Leu Asn
                130                 135                 140

Lys Leu Gly Glu Asn Ile Thr Thr Phe Ala Glu Thr Lys Thr Asn
145                 150                 155                 160

Ile Val Lys Ile Asp Glu Lys Leu Glu Ala Val Ala Asp Thr Val Asp
                165                 170                 175

Lys His Ala Glu Ala Phe Asn Asp Ile Ala Asp Ser Leu Asp Glu Thr
                180                 185                 190

Asn Thr Lys Ala Asp Glu Ala Val Lys Thr Ala Asn Glu Ala Lys Gln
                195                 200                 205
```

```
Thr Ala Glu Glu Thr Lys Gln Asn Val Asp Ala Lys Val Lys Ala Ala
    210                 215                 220

Glu Thr Ala Ala Gly Lys Ala Glu Ala Ala Ala Gly Thr Ala Asn Thr
225                 230                 235                 240

Ala Ala Asp Lys Ala Glu Ala Val Ala Ala Lys Val Thr Asp Ile Lys
                245                 250                 255

Ala Asp Ile Ala Thr Asn Lys Asp Asn Ile Ala Lys Lys Ala Asn Ser
            260                 265                 270

Ala Asp Val Tyr Thr Arg Glu Glu Ser Asp Ser Lys Phe Val Arg Ile
            275                 280                 285

Asp Gly Leu Asn Ala Thr Thr Glu Lys Leu Asp Thr Arg Leu Ala Ser
290                 295                 300

Ala Glu Lys Ser Ile Thr Glu His Gly Thr Arg Leu Asn Gly Leu Asp
305                 310                 315                 320

Arg Thr Val Ser Asp Leu Arg Lys Glu Thr Arg Gln Gly Leu Ala Glu
                325                 330                 335

Gln Ala Ala Leu Ser Gly Leu Phe Gln Pro Tyr Asn Val Gly Arg Phe
            340                 345                 350

Asn Val Thr Ala Ala Val Gly Gly Tyr Lys Ser Glu Ser Ala Val Ala
            355                 360                 365

Ile Gly Thr Gly Phe Arg Phe Thr Glu Asn Phe Ala Ala Lys Ala Gly
        370                 375                 380

Val Ala Val Gly Thr Ser Ser Gly Ser Ser Ala Ala Tyr His Val Gly
385                 390                 395                 400

Val Asn Tyr Glu Trp
                405

<210> SEQ ID NO 144
<211> LENGTH: 6
<212> TYPE: PRT
<213> ORGANISM: Artificial Sequence
<220> FEATURE:
<223> OTHER INFORMATION: Synthetic Construct

<400> SEQUENCE: 144

Gly Ser Gly Gly Gly Gly
 1               5
```

US 8,980,286 B2

MULTIPLE VARIANTS OF MENINGOCOCCAL PROTEIN NBM1870

CROSS REFERENCE TO RELATED APPLICATIONS

This application is a Continuation of U.S. patent application Ser. No. 10/536,215, filed May 23, 2005, which is the National Stage of International Patent Application of PCT/IB2003/006320, filed Nov. 21, 2003, which claims the benefit of United Kingdom Patent Application Serial No. 0227346.4, filed Nov. 22, 2002, each of which is hereby incorporated by reference in its entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 223002100901SEQLIST.txt, date recorded: Feb. 1, 2012, size: 223 KB).

TECHNICAL FIELD

This invention is in the field of vaccination and, in particular, vaccination against disease caused by pathogenic bacteria in the genus *Neisseria*, such as *N. meningitidis* (meningococcus).

BACKGROUND ART

*Neisseria meningitidis* is a Gram-negative encapsulated bacterium which colonises the upper respiratory tract of approximately 10% of human population. Approximately once in every 10,000 colonised people (or once in 100,000 population) the bacterium enters the blood stream where it multiplies and causes sepsis. From the blood stream the bacterium can cross the blood-brain barrier and cause meningitis. Both diseases are devastating and can kill 5-15% of affected children and young adults within hours, despite the availability of effective antibiotics. Up to 25% of those who survive are left with permanent sequelae.

Prevention of disease has been partially accomplished by vaccination. Immunisation was made possible in 1969 when it was discovered that protection from disease correlates with the presence of serum antibodies able to induce complement-mediated killing of bacteria, and that purified capsular polysaccharide was able to induce these antibodies. Although polysaccharide and conjugate vaccines are available against serogroups A, C, W135 and Y, this approach cannot be applied to serogroup B because the capsular polysaccharide is a polymer of polysialic acid, which is a self antigen in humans. To develop a vaccine against serogroup B, surface-exposed proteins contained in outer membrane vesicles (OMVs) have been used. These vaccines elicit serum bactericidal antibody responses and protect against disease, but they fail to induce cross-strain protection [1].

The complete genome sequence of serogroup B *N. meningitidis* has been published [2] and has been subjected to analysis in order to identify vaccine antigens [3]. The complete genome sequence of serogroup A *N. meningitidis* is also known [4], and the complete genome sequence of *Neisseria gonorrhoeae* strain FA1090 is available [5]. References 6 to 9 disclose proteins from *Neisseria meningitidis* and *Neisseria gonorrhoeae*, and approaches to expression of these proteins are disclosed in references 10 to 12.

It is an object of the invention to provide further and improved compositions for providing immunity against meningococcal disease and/or infection, particularly for serogroup B.

DISCLOSURE OF THE INVENTION

One of the ~2200 proteins disclosed in reference 2 is 'NMB1870'. The protein was originally disclosed as protein '741' from strain MC58 [SEQ IDs 2535 & 2536 in ref. 8; SEQ ID 1 herein], and has also been referred to as 'GNA1870' [following ref. 3] or as 'ORF2086' [13].

It has now been found that NMB1870 is an extremely effective antigen for eliciting anti-meningococcal antibody responses, and that it is expressed across all meningococcal serogroups. NMB1870 has been found in all meningococcal strains tested to date. Forty-two different meningococcal NMB1870 sequences have been identified, and it has been found that these sequences group into three variants. Furthermore, it has been found that serum raised against a given variant is bactericidal within the same variant group, but is not active against strains which express one of the other two variants i.e. there is intra-variant cross-protection, but not inter-variant cross-protection. For maximum cross-strain efficacy, therefore, more than one variant should be used for immunising a patient.

The invention therefore provides a composition comprising at least two of the following antigens:

(a) a first protein, comprising an amino acid sequence having at least a % sequence identity to SEQ ID 24 and/or comprising an amino acid sequence consisting of a fragment of at least x contiguous amino acids from SEQ ID 24;

(b) a second protein, comprising an amino acid sequence having at least b % sequence identity to SEQ ID 33 and/or comprising an amino acid sequence consisting of a fragment of at least y contiguous amino acids from SEQ ID 33; and (c) a third protein, comprising an amino acid sequence having at least c % sequence identity to SEQ ID 41 and/or comprising an amino acid sequence consisting of a fragment of at least z contiguous amino acids from SEQ ID 41.

The invention also provides the use of NMB1870 for providing immunity against multiple (e.g. 2, 3, 4, 5 or more) strains and/or serogroups of *N. meningitidis*.

Variability in and Between (a), (b) and (c)

The value of a is at least 85 e.g. 86, 87, 88, 89, 90, 91, 92, 93, 94, 95, 96, 97, 98, 99, 99.5, or more.

The value of b is at least 85 e.g. 86, 87, 88, 89, 90, 91, 92, 93, 94, 95, 96, 97, 98, 99, 99.5, or more.

The value of c is at least 85 e.g. 86, 87, 88, 89, 90, 91, 92, 93, 94, 95, 96, 97, 98, 99, 99.5, or more.

The values of a, b and c are not intrinsically related to each other.

The value of x is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250).

The value of y is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250).

The value of z is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250).

The values of x, y and z are not intrinsically related to each other.

It is preferred that any given amino acid sequence will not fall into more than one of categories (a), (b) and (c). Any given NMB1870 sequence will thus fall into only one of categories (a), (b) and (c). It is thus preferred that: protein (a) has less than i % sequence identity to protein (b); protein (a) has less than j % sequence identity to protein (c); and protein (b) has less than k % sequence identity to protein (c). The value of i is 60 or more (e.g. 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, etc.) and is at most a. The value of j is 60 or more (e.g. 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, etc.) and is at most b. The value of k is 60 or more (e.g. 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, etc.) and is at most c. The values of i, j and k are not intrinsically related to each other.

In an example two-protein embodiment of the invention, therefore, protein (a) might have >85% sequence identity to SEQ ID 24, protein (b) might have >85% sequence identity to SEQ ID 33, but protein (a) and (b) have less than 75% sequence identity to each other. Proteins (a) and (b) are therefore each closely related to their 'prototype' sequences, but they are not so closely related to each other.

In an example three-protein embodiment of the invention, therefore, protein (a) might have >85% sequence identity to SEQ ID 24, protein (b) might have >85% sequence identity to SEQ ID 33, protein (c) might have >85% sequence identity to SEQ ID 41, but protein (a) and (b) have less than 75% sequence identity to each other, protein (a) and (c) have less than 75% sequence identity to each other, and protein (b) and (c) have less than 75% sequence identity to each other.

The mixture of two or more of (a), (b) and (c) can preferably elicit an antibody response which is bactericidal against at least one N. meningitidis strain from each of at least two of the following three groups of strains:

(a) MC58, gb185 (=M01-240185), m4030, m2197, m2937, iss1001, NZ394/98, 67/00, 93/114, bz198, m1390, nge28, lnp17592, 00-241341, f6124, 205900, m198/172, bz133, gb149 (=M01-240149), nm008, nm092, 30/00, 39/99, 72/00, 95330, bz169, bz83, cu385, h44/76, m1590, m2934, m2969, m3370, m4215, m4318, n44/89, 14847.
(b) 961-5945, 2996, 96217, 312294, 11327, a22, gb013 (=M01-240013), e32, m1090, m4287, 860800, 599, 95N477, 90-18311, c11, m986, m2671, 1000, m1096, m3279, bz232, dk353, m3697, ngh38, L93/4286.
(c) M1239, 16889, gb355 (=M01-240355), m3369, m3813, ngp165.

For example, the mixture can elicit a bactericidal response effective against each of serogroup B N. meningitidis strains MC58, 961-5945 and M1239.

The mixture of two or more of (a), (b) and (c) can preferably elicit an antibody response which is bactericidal against at least 50% of clinically-relevant meningococcal serogroup B strains (e.g. at least 60%, 70%, 80%, 90%, 95% or more).

The mixture of two or more of (a), (b) and (c) can preferably elicit an antibody response which is bactericidal against strains of serogroup B N. meningitidis and strains of at least one (e.g. 1, 2, 3, 4) of serogroups A, C, W135 and Y.

The mixture of two or more of (a), (b) and (c) can preferably elicit an antibody response which is bactericidal against strains of N. gonococcus and/or N. cinerea.

The mixture of two or more of (a), (b) and (c) can preferably elicit an antibody response which is bactericidal against strains from at least two of the three main branches of the dendrogram shown in FIG. 9 (i.e. the dendrogram obtained by analysing SEQ IDs 1 to 23 by the Kimura & Jukes-Cantor algorithm).

The mixture of two or more of (a), (b) and (c) can preferably elicit an antibody response which is bactericidal against N. meningitidis strains in at least 2 (e.g. 2, 3, 4, 5, 6, 7) of hypervirulent lineages ET-37, ET-5, cluster A4, lineage 3, subgroup I, subgroup III, and subgroup IV-1 [14, 15].

Compositions of the invention may additionally induce bactericidal antibody responses against one or more hyperinvasive lineages.

The mixture of two or more of (a), (b) and (c) can preferably elicit an antibody response which is bactericidal against N. meningitidis strains in at least at least 2 (e.g. 2, 3, 4, 5, 6, 7) of the following multilocus sequence types: ST1, ST4, ST5, ST8, ST11, ST32 and ST41 [16]. The mixture may also elicit an antibody response which is bactericidal against ST44 strains.

Bactericidal antibody responses are conveniently measured in mice and are a standard indicator of vaccine efficacy [e.g. see end-note 14 of reference 3]. The composition need not induce bactericidal antibodies against each and every MenB strain within the specified lineages or MLST; rather, for any given group of four of more strains of serogroup B meningococcus within a particular hypervirulent lineage or MLST, the antibodies induced by the composition are bactericidal against at least 50% (e.g. 60%, 70%, 80%, 90% or more) of the group. Preferred groups of strains will include strains isolated in at least four of the following countries: GB, AU, CA, NO, IT, US, NZ, NL, BR, and CU. The serum preferably has a bactericidal titre of at least 1024 (e.g. $2^{10}$, $2^{11}, 2^{12}, 2^{13}, 2^{14}, 2^{15}, 2^{16}, 2^{17}, 2^{18}$ or higher, preferably at least $2^{14}$) i.e. the serum is able to kill at least 50% of test bacteria of a particular strain when diluted 1/1024 e.g. as described in end-note 14 of reference 3.

Lipoproteins

NMB1870 is naturally a lipoprotein in N. meningitidis. It has also been found to be lipidated when expressed in E. coli.

It is preferred that one or more (e.g. 1, 2, 3, 4, 5, 6, 7, 8, 9, 10) NMB1870 proteins included in compositions of the invention is a lipoprotein.

The invention provides a protein comprising an amino acid sequence having at least 50% (e.g. 60%, 70%, 80%, 85%, 90%, 95%, 96%, 97%, 98%, 99%, 99.5% or more) sequence identity to one or more of SEQ IDs 24 to 45, and/or comprising an amino acid sequence consisting of a fragment of at least 7 (e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250) contiguous amino acids from one or more of SEQ IDs 24 to 45 (preferably SEQ IDs 25 to 45), characterised in that the protein is a lipoprotein.

Preferably, the lipoprotein has a N-terminal cysteine residue, to which the lipid is covalently attached. To prepare the lipoprotein via bacterial expression generally requires a suitable N-terminal signal peptide to direct lipidation by diacylglyceryl transferase, followed by cleavage by lipoprotein-specific (type II) SPase. While the lipoprotein of the invention may have a N-terminal cysteine (e.g. SEQ IDs 24 to 45), therefore, it will be a product of post-translational modification of a nascent protein which has the usual N-terminal methionine (e.g. SEQ IDs 1 to 22).

The lipoprotein may be associated with a lipid bilayer and may be solubilised with detergent.

Sequences

NMB1870 proteins useful for the invention comprise an amino acid sequence having at least 50% (e.g. 60%, 70%, 80%, 85%, 90%, 95%, 96%, 97%, 98%, 99%, 99.5% or more)

sequence identity to one or more of SEQ ID NO$^S$ 1 to 23, and/or comprising an amino acid sequence consisting of a fragment of at least 7 (e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250) contiguous amino acids from one or more of SEQ ID NO$^S$ 1 to 23.

Preferred fragments include: (a) fragments which comprise an epitope, and preferably a bactericidal epitope; (b) fragments common to two or more of SEQ IDs 1 to 23; (c) SEQ IDs 1 to 23 with 1 or more (e.g. 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 60, 70, 80, 90, 100, 110, 120 or more, etc.) N-terminal residues deleted; (d) SEQ IDs 1 to 23 with 1 or more (e.g. 1, 2, 3, 4, 5, 6, 7, 8, 9, 10, 11, 12, 13, 14, 15, 16, 17, 18, 19, 20, 21, 22, 23, 24, 25, etc.) C-terminal residues deleted; and (e) SEQ IDs 1 to 23 without their signal peptides (e.g. SEQ IDs 24 to 45). These preferred fragments are not mutually exclusive e.g. a fragment could fall into category (a) and (b), or category (c) and (d), etc.

Further NMB1870 proteins useful for the invention comprise an amino acid sequence having at least 50% (e.g. 60%, 70%, 80%, 85%, 90%, 95%, 96%, 97%, 98%, 99%, 99.5% or more) sequence identity to one or more of SEQ ID NO$^S$ 123 to 141, and/or comprising an amino acid sequence consisting of a fragment of at least 7 (e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250) contiguous amino acids from one or more of SEQ ID NO$^S$ 123 to 141.

Further NMB1870 proteins useful for the invention comprise an amino acid sequence having at least 50% (e.g. 60%, 70%, 80%, 85%, 90%, 95%, 96%, 97%, 98%, 99%, 99.5% or more) sequence identity to one or more of SEQ ID NO$^S$ 1 to 252 of reference 13, and/or comprising an amino acid sequence consisting of a fragment of at least 7 (e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250) contiguous amino acids from one or more of SEQ ID NO$^S$ 1 to 252 of reference 13. SEQ ID NO$^S$ 300-302 of reference 13 provide consensus sequences, and SEQ ID NO$^S$ 254-299 are fragments. Preferred fragments include: (a) fragments which comprise an epitope, and preferably a bactericidal epitope; (b) fragments common to two or more of SEQ IDs 123 to 141; (c) SEQ IDs 123 to 141 with 1 or more (e.g. 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 60, 70, 80, 90, 100, 110, 120 or more, etc.) N-terminal residues deleted; (d) SEQ IDs 123 to 141 with 1 or more (e.g. 1, 2, 3, 4, 5, 6, 7, 8, 9, 10, 11, 12, 13, 14, 15, 16, 17, 18, 19, 20, 21, 22, 23, 24, 25, etc.) C-terminal residues deleted; and (e) SEQ IDs 123 to 141 without their signal peptides. These preferred fragments are not mutually exclusive e.g. a fragment could fall into category (a) and (b), or category (c) and (d), etc.

Preferred amino acid sequences with <100% identity to SEQ ID NO$^S$ 1 to 23 and 123 to 141 are allelic variants, homologs, orthologs, paralogs, mutants etc. thereof. It is preferred that one or more of the differences in allelic variants, homologs, orthologs, paralogs or mutants, compared to SEQ ID NO$^S$ 1 to 23 and 123 to 141, involves a conservative amino acid replacement i.e. replacement of one amino acid with another which has a related side chain. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity.

A preferred subset of proteins does not include the amino acid sequence TRSKP (SEQ ID NO: 70) or TRSKPV (SEQ ID NO: 71) within 10 amino acids of the protein's N-terminus. Another preferred subset of proteins does not include the amino acid sequence PSEPPFG (SEQ ID NO: 72) within 10 amino acids of the protein's N-terminus.

Another preferred subset of proteins for use with the invention includes the amino acid sequence (Gly)$_n$ where n is 1, 2, 3, 4 or more e.g. SEQ ID NO: 73.

A characteristic of preferred proteins of the invention is the ability to induce bactericidal anti-meningococcal antibodies after administration to a host animal.

Proteins can be prepared by various means e.g. by chemical synthesis (at least in part), by digesting longer polypeptides using proteases, by translation from RNA, by purification from cell culture (e.g. from recombinant expression or from *N. meningitidis* culture). etc. Heterologous expression in an *E. coli* host is a preferred expression route (e.g. strains DH5α, BL21(DE$_3$), BLR, etc.).

Proteins of the invention may be attached or immobilised to a solid support.

Proteins of the invention may comprise a detectable label e.g. a radioactive label, a fluorescent label, or a biotin label. This is particularly useful in immunoassay techniques.

Proteins can take various forms (e.g. native, fusions, glycosylated, non-glycosylated, lipidated, disulfide bridges, etc.). Proteins are preferably meningococcal proteins.

Proteins are preferably prepared in substantially pure or substantially isolated form (i.e. substantially free from other Neisserial or host cell proteins) or substantially isolated form. In general, the proteins are provided in a non-naturally occurring environment e.g. they are separated from their naturally-occurring environment. In certain embodiments, the subject protein is present in a composition that is enriched for the protein as compared to a control. As such, purified protein is provided, whereby purified is meant that the protein is present in a composition that is substantially free of other expressed proteins, where by substantially free is meant that less than 90%, usually less than 60% and more usually less than 50% of the composition is made up of other expressed proteins.

The term "protein" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, proteins containing one or more analogs of an amino acid (including, for example, unnatural amino acids, etc.), as well as other modifications known in the art. Proteins can occur as single chains or associated chains.

The invention also provides proteins comprising an amino acid sequence having at least 50% (e.g. 60%, 70%, 80%, 85%, 90%, 95%, 96%, 97%, 98%, 99%, 99.5% or more) sequence identity to one or more of SEQ ID NO$^S$ 77, 79, 82, 83, 85, 87, 88, 89, 90, 91, 92, 93 & 94, and/or comprising an amino acid sequence consisting of a fragment of at least 7 (e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250) contiguous amino acids from one or more of SEQ ID NO$^S$ 77, 79, 82, 83, 85, 87, 88, 89, 90, 91, 92, 93 & 94.

Where the invention relates to a single NMB1870 protein, the invention does not encompass a protein comprising an amino acid sequence as disclosed in any of SEQ ID NO$^S$: 1 to 302 of reference 13. However, such proteins can optionally be used where the invention relates to NMB1870 mixtures Hybrid and Tandem Proteins As mentioned above, NMB1870 may be used in the form of a fusion protein, although the proteins may also be expressed other than as a fusion protein (e.g. without GST, MBP, his-tag or similar).

Fusion proteins can have a C-terminus and/or N-terminus fusion partner. Where a N-terminus fusion partner is used with SEQ IDs 1 to 23, the skilled person will realise that the start codon will (if included) be expressed as a valine, because GTG is translated as valine except when it is used as a start codon, in which case it is translated as N-formyl-methionine.

Suitable N-terminus fusion partners include leader peptides from other proteins (particularly other lipoproteins), which may be substituted for the natural NMB1870 leader peptides (i.e. the sequence prior to the N-terminus cysteine may be replaced with another leader peptide of interest). Examples are sequences comprising SEQ ID 46, and the *H. influenzae* P4 lipoprotein leader sequence [e.g. 17].

A preferred type of fusion protein is disclosed in references 10, 11 & 12 in which two or more (e.g. 3, 4, 5, 6 or more) Neisserial proteins are joined such that they are translated as a single polypeptide chain. In general, such hybrid proteins can be represented by the formula:

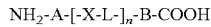

NH$_2$-A-[-X-L-]$_n$-B-COOH wherein X is an amino acid sequence comprising a Neisserial sequence, L is an optional linker amino acid sequence, A is an optional N-terminal amino acid sequence, B is an optional C-terminal amino acid sequence, and n is an integer greater than 1. The value of n is between 2 and x, and the value of x is typically 3, 4, 5, 6, 7, 8, 9 or 10. Preferably n is 2, 3 or 4; it is more preferably 2 or 3; most preferably, n=2.

According to the present invention, at least one of the -X- moieties is a NMB1870 sequence as defined above. In some hybrid proteins, referred to as 'tandem' proteins, at least one of the -X- moieties has sequence identity to at least one of the other X moieties e.g. X$_1$ is SEQ ID NO: 24 and X$_2$ is a SEQ ID NO: 25. Proteins in which two or three of the three NMB1870 variants are joined as a tandem protein are preferred.

For X moieties other than X$_1$, it is preferred that the native leader peptide should be omitted, particularly where X$_1$ is not a NMB1870 sequence. In one embodiment, the leader peptides will be deleted except for that of the -X- moiety located at the N-terminus of the hybrid protein i.e. the leader peptide of X$_1$ will be retained, but the leader peptides of X$_2$...X$_n$ will be omitted. This is equivalent to deleting all leader peptides and using the leader peptide of X$_1$ as moiety -A-.

Preferred NMB1870 sequences for use as -X- moieties are truncated up to and including the poly-glycine sequence found near the mature N-terminus e.g. the NMB1870 sequence will begin VAA . . . (or IAA . . . for strain m3813). Such NMB1870 sequences include SEQ ID NO$^S$: 80, 81 & 84.

For each n instances of [-X-L-], linker amino acid sequence -L- may be present or absent. For instance, when n=2 the hybrid may be NH$_2$—X$_1$-L$_1$-X$_2$-L$_2$-COOH, NH$_2$—X$_1$—X$_2$—COOH, NH$_2$—X$_1$-L$_1$-X$_2$—COOH, NH$_2$—X$_1$—X$_2$-L$_2$-COOH, etc. Linker amino acid sequence(s)-L- will typically be short (e.g. 20 or fewer amino acids i.e. 19, 18, 17, 16, 15, 14, 13, 12, 11, 10, 9, 8, 7, 6, 5, 4, 3, 2, 1). Examples include short peptide sequences which facilitate cloning, poly-glycine linkers (i.e. Gly$_n$ where n=2, 3, 4, 5, 6, 7, 8, 9, 10 or more), and histidine tags (i.e. His$_n$ where n=3, 4, 5, 6, 7, 8, 9, 10 or more). Other suitable linker amino acid sequences will be apparent to those skilled in the art. A useful linker is GSGGGG (SEQ ID NO: 144), with the Gly-Ser dipeptide being formed from a BamHI restriction site, thus aiding cloning and manipulation, and the Gly$_4$ tetrapeptide (SEQ ID NO: 73) is another typical poly-glycine linker. Another useful linker is SEQ ID NO: 78.

-A- is an optional N-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. His$_n$ where n=3, 4, 5, 6, 7, 8, 9, 10 or more). Other suitable N-terminal amino acid sequences will be apparent to those skilled in the art. If X$_1$ lacks its own N-terminus methionine, -A- may provide such a methionine residue in the translated protein (e.g. -A- is a single Met residue). A useful -A- moiety for expressing NMB1870 is SEQ ID NO: 86. In mature lipoproteins, -A- preferably provides a N-terminus cysteine (e.g. -A- is a single Cys residue).

-B- is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. His$_n$ where n=3, 4, 5, 6, 7, 8, 9, 10 or more), or sequences which enhance protein stability. Other suitable C-terminal amino acid sequences will be apparent to those skilled in the art.

In preferred hybrid proteins of the invention, one of the X moieties is a 'protein 936' sequence. For example, where n=2, A=Met, X$_1$ is a 936 sequence (e.g. SEQ ID NO: 76, which is the processed MC58 protein), L$_1$=a poly-glycine linker (e.g. SEQ ID NO: 144), X$_2$=a NMB1870 sequence in which the N-terminus has been deleted up to and including its own poly-glycine sequence, and L$_2$ and B may be omitted. An example of such a hybrid protein is SEQ ID NO: 77, in which truncated NMB1870 from strain m1239 is downstream of the processed 936 from strain MC58. Further examples of hybrid proteins of 936 (2996 strain) and truncated NMB1870 (strain 2996 or M1239) are SEQ ID NO$^S$: 91, 92, 93 & 94.

Preferred tandem proteins where n=3 may have all three NMB1870 variants in any order:

| X$_1$ | 1 | 1 | 2 | 2 | 3 | 3 |
| X$_2$ | 2 | 3 | 1 | 3 | 1 | 2 |
| X$_3$ | 3 | 2 | 3 | 1 | 2 | 1 |

Preferred tandem proteins where n=2 may have two different NMB variants:

| X$_1$ | 1 | 1 | 2 | 2 | 3 | 3 |
| X$_2$ | 2 | 3 | 1 | 3 | 1 | 2 |

Examples of tandem proteins where n=2 (two different NMB variants) are SEQ ID NO$^S$: 79, 82, 83, 85, 87, 88, 89 & 90, which use strains MC58 (variant 1), 2996 (variant 2) and M1239 (variant 3).

An example of a tandem protein where n=3 is given as SEQ ID NO: 142.

NadA

NadA protein is disclosed in references 191 and 192. These references disclose three distinct alleles of NadA, although some minor variations were found e.g. serogroup C strain ISS1024 has a variant of allele 2 with a single heptad repeat deletion, serogroup C strains ISS759 and 973-1720 both contain a variant of allele 3 with a single amino acid mutation in the leader peptide, and serogroup B strain 95330 contains a recombination of alleles 1 and 2.

In sequencing NadA from Haji strains of meningococcus, SEQ ID NO: 143 was identified. This protein is a recombinant of known alleles 2 and 3.

The invention provides a protein comprising an amino acid sequence having at least 50% (e.g. 60%, 70%, 80%, 85%, 90%, 95%, 96%, 97%, 98%, 99%, 99.5% or more e.g. 100%) sequence identity to SEQ ID NO: 143, and/or comprising an amino acid sequence consisting of a fragment of at least 7 (e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250) contiguous amino acids from SEQ ID NO: 143.

Preferred fragments include: (a) fragments which comprise an epitope, and preferably a bactericidal epitope; (b) fragments common to SEQ ID NO: 143 and at least one of the NadA sequences disclosed in references 191 and 192; (c) SEQ ID NO: 143 with 1 or more (e.g. 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 60, 70, 80, 90, 100, 110, 120 or more, etc.) N-terminal residues deleted; (d) SEQ ID NO: 143 with 1 or more (e.g. 1, 2, 3, 4, 5, 6, 7, 8, 9, 10, 11, 12, 13, 14, 15, 16, 17, 18, 19, 20, 21, 22, 23, 24, 25, etc.) C-terminal residues deleted; and (e) SEQ ID NO: 143 without its signal peptide. These preferred fragments are not mutually exclusive e.g. a fragment could fall into category (a) and (b), or category (c) and (d), etc.

Preferred amino acid sequences with <100% identity to SEQ ID NO: 143 are allelic variants, homologs, orthologs, paralogs, mutants etc. thereof. It is preferred that one or more of the differences in allelic variants, homologs, orthologs, paralogs or mutants, compared to SEQ ID NO: 143, involves a conservative amino acid replacement.

Nucleic Acids

The invention provides nucleic acid encoding a protein of the invention as defined above. The invention also provides nucleic acid comprising: (a) a fragment of at least n consecutive nucleotides from said nucleic acid, wherein n is 10 or more (e.g. 12, 14, 15, 18, 20, 25, 30, 35, 40, 50, 60, 70, 80, 90, 100, 150, 200, 500 or more); and/or (b) a sequence having at least 50% (e.g. 60%, 70%, 80%, 90%, 95%, 96%, 97%, 98%, 99% or more) sequence identity to said nucleic acid.

Furthermore, the invention provides nucleic acid which can hybridise to nucleic acid encoding a protein of the invention, preferably under "high stringency" conditions (e.g. 65° C. in a 0.1×SSC, 0.5% SDS solution).

Nucleic acids of the invention can be used in hybridisation reactions (e.g. Northern or Southern blots, or in nucleic acid microarrays or 'gene chips') and amplification reactions (e.g. PCR, SDA, SSSR, LCR, TMA, NASBA, etc.) and other nucleic acid techniques.

Nucleic acids of the invention can be prepared in many ways e.g. by chemical synthesis in whole or part, by digesting longer polynucleotides using nucleases (e.g. restriction enzymes), from genomic or cDNA libraries, from the bacterium itself, etc.

Nucleic acids of the invention can take various forms e.g. single-stranded, double-stranded, vectors, primers, probes, labelled, unlabelled, etc.

Nucleic acids of the invention are preferably in isolated or substantially isolated form.

The invention includes nucleic acid comprising sequences complementary to those described above e.g. for antisense or probing, or for use as primers.

The term "nucleic acid" includes DNA and RNA, and also their analogues, such as those containing modified backbones, and also peptide nucleic acids (PNA) etc.

Nucleic acid according to the invention may be labelled e.g. with a radioactive or fluorescent label. This is particularly useful where the nucleic acid is to be used in nucleic acid detection techniques e.g. where the nucleic acid is a primer or as a probe for use in techniques such as PCR, LCR, TMA, NASBA, etc.

The invention also provides vectors comprising nucleotide sequences of the invention (e.g. cloning or expression vectors, such as those suitable for nucleic acid immunisation) and host cells transformed with such vectors.

Further Antigenic Components

Compositions of the invention include a small number (e.g. fewer than t antigens, where t is 15, 14, 13, 12, 11, 10, 9, 8, 7, 6, 5, 4 or 3) of purified serogroup B antigens. It is particularly preferred that the composition should not include complex or undefined mixtures of antigens e.g. it is preferred not to include outer membrane vesicles in the composition. The antigens are preferably expressed recombinantly in a heterologous host and then purified.

The composition of the invention includes at least two different NMB1870 proteins. It may also include another neisserial antigen, as a vaccine which targets more than one antigen per bacterium decreases the possibility of selecting escape mutants. Neisserial antigens for inclusion in the compositions include proteins comprising:

(a) the 446 even SEQ IDs (i.e. 2, 4, 6, . . . , 890, 892) disclosed in reference 6.
(b) the 45 even SEQ IDs (i.e. 2, 4, 6, . . . , 88, 90) disclosed in reference 7;
(c) the 1674 even SEQ IDs 2-3020, even SEQ IDs 3040-3114, and all SEQ IDs 3115-3241, disclosed in reference 8;
(d) the 2160 amino acid sequences NMB0001 to NMB2160 from reference 2;
(e) an amino acid sequence disclosed in reference 10, 11 or 12;
(f) a variant, homolog, ortholog, paralog, mutant etc. of (a) to (e); or
(g) an outer membrane vesicle prepared from N. meningitidis [e.g. see ref. 139].

In addition to Neisserial antigens, the composition may include antigens for immunising against other diseases or infections. For example, the composition may include one or more of the following further antigens:

antigens from *Helicobacter pylori* such as CagA [18 to 21], VacA [22, 23], NAP [24, 25, 26], HopX [e.g. 27], HopY [e.g. 27] and/or urease.

a saccharide antigen from *N. meningitidis* serogroup A, C, W135 and/or Y, such as the oligosaccharide disclosed in ref. 28 from serogroup C [see also ref. 29] or the oligosaccharides of ref. 30.

a saccharide antigen from *Streptococcus pneumoniae* [e.g. 31, 32, 33].

an antigen from hepatitis A virus, such as inactivated virus [e.g. 34, 35].

an antigen from hepatitis B virus, such as the surface and/or core antigens [e.g. 35, 36].

a diphtheria antigen, such as a diphtheria toxoid [e.g. chapter 3 of ref. 37] e.g. the $CRM_{197}$ mutant [e.g. 38].

a tetanus antigen, such as a tetanus toxoid [e.g. chapter 4 of ref. 37].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 39 & 40].

a saccharide antigen from *Haemophilus influenzae* B [e.g. 29].

an antigen from hepatitis C virus [e.g. 41].

an antigen from *N. gonorrhoeae* [e.g. 6, 7, 8, 42].

an antigen from *Chlamydia pneumoniae* [e.g. refs. 43 to 49].

an antigen from *Chlamydia trachomatis* [e.g. 50].

an antigen from *Porphyromonas gingivalis* [e.g. 51].

polio antigen(s) [e.g. 52, 53] such as IPV.

rabies antigen(s) [e.g. 54] such as lyophilised inactivated virus [e.g. 55, RabAvert™].

measles, mumps and/or rubella antigens [e.g. chapters 9, 10 & 11 of ref. 37].

influenza antigen(s) [e.g. chapter 19 of ref. 37], such as the haemagglutinin and/or neuraminidase surface proteins.

an antigen from *Moraxella catarrhalis* [e.g. 56].

an protein antigen from *Streptococcus agalactiae* (group B *streptococcus*) [e.g. 57, 58].

a saccharide antigen from *Streptococcus agalactiae* (group B *streptococcus*).

an antigen from *Streptococcus pyogenes* (group A *streptococcus*) [e.g. 58, 59, 60].

an antigen from *Staphylococcus aureus* [e.g. 61].

an antigen from *Bacillus anthracis* [e.g. 62, 63, 64].

an antigen from a virus in the flaviviridae family (genus *flavivirus*), such as from yellow fever virus, Japanese encephalitis virus, four serotypes of Dengue viruses, tick-borne encephalitis virus, West Nile virus.

a pestivirus antigen, such as from classical porcine fever virus, bovine viral diarrhoea virus, and/or border disease virus.

a parvovirus antigen e.g. from parvovirus B19.

a prion protein (e.g. the CJD prion protein)

an amyloid protein, such as a beta peptide [65]

a cancer antigen, such as those listed in Table 1 of ref. 66 or in tables 3 & 4 of ref. 67.

The composition may comprise one or more of these further antigens.

Toxic protein antigens may be detoxified where necessary (e.g. detoxification of pertussis toxin by chemical and/or genetic means [40]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Saccharide antigens are preferably in the form of conjugates. Carrier proteins for the conjugates include the *N. meningitidis* outer membrane protein [68], synthetic peptides [69, 70], heat shock proteins [71, 72], pertussis proteins [73, 74], protein D from *H. influenzae* [75], cytokines [76], lymphokines [76], streptococcal proteins, hormones [76], growth factors [76], toxin A or B from *C. dificile* [77], iron-uptake proteins [78], etc. A preferred carrier protein is the CRM197 diphtheria toxoid [79].

Antigens in the composition will typically be present at a concentration of at least 1 µg/ml each. In general, the concentration of any given antigen will be sufficient to elicit an immune response against that antigen.

Immunogenic compositions of the invention may be used therapeutically (i.e. to treat an existing infection) or prophylactically (i.e. to prevent future infection).

As an alternative to using proteins antigens in the immunogenic compositions of the invention, nucleic acid (preferably DNA e.g. in the form of a plasmid) encoding the antigen may be used.

Particularly preferred compositions of the invention include one, two or three of: (a) saccharide antigens from meningococcus serogroups Y, W135, C and (optionally) A; (b) a saccharide antigen from *Haemophilus influenzae* type B; and/or (c) an antigen from *Streptococcus pneumoniae*.

Meningococcus Serogroups Y, W135, C and (Optionally) A

Polysaccharide vaccines against serogroups A, C, W135 & Y have been known for many years. These vaccines (MENCEVAX ACWY™ and MENOMUNE™) are based on the organisms' capsular polysaccharides and, although they are effective in adolescents and adults, they give a poor immune response and short duration of protection, and they cannot be used in infants.

In contrast to the unconjugated polysaccharide antigens in these vaccines, the recently-approved serogroup C vaccines (Menjugate™ [80, 28], Meningitec™ and NeisVac-C™) include conjugated saccharides. Menjugate™ and Meningitec™ have oligosaccharide antigens conjugated to a $CRM_{197}$ carrier, whereas NeisVac-C™ uses the complete polysaccharide (de-O-acetylated) conjugated to a tetanus toxoid carrier. The proposed MenActra™ vaccine contains conjugated capsular saccharide antigens from each of serogroups Y, W135, C and A.

Compositions of the present invention preferably include capsular saccharide antigens from one or more of meningococcus serogroups Y, W135, C and (optionally) A, wherein the antigens are conjugated to carrier protein(s) and/or are oligosaccharides. For example, the composition may include a capsular saccharide antigen from: serogroup C; serogroups A and C; serogroups A, C and W135; serogroups A, C and Y; serogroups C, W135 and Y; or from all four of serogroups A, C, W135 and Y.

A typical quantity of each meningococcal saccharide antigen per dose is between 1 µg and 20 µg e.g. about 1 µg, about 2.5 µg, about 4 µg, about 5 µg, or about 10 µg (expressed as saccharide).

Where a mixture comprises capsular saccharides from both serogroups A and C, the ratio (w/w) of MenA saccharide:MenC saccharide may be greater than 1 (e.g. 2:1, 3:1, 4:1, 5:1, 10:1 or higher). Where a mixture comprises capsular saccharides from serogroup Y and one or both of serogroups C and W135, the ratio (w/w) of MenY saccharide:MenW135 saccharide may be greater than 1 (e.g. 2:1, 3:1, 4:1, 5:1, 10:1 or higher) and/or that the ratio (w/w) of MenY saccharide:MenC saccharide may be less than 1 (e.g. 1:2, 1:3, 1:4, 1:5, or lower). Preferred ratios (w/w) for saccharides from serogroups A:C:W135:Y are: 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1. Preferred ratios (w/w) for saccharides from serogroups C:W135:Y are: 1:1:1; 1:1:2; 1:1:1; 2:1:1; 4:2:1; 2:1:2; 4:1:2; 2:2:1; and 2:1:1. Using a substantially equal mass of each saccharide is preferred.

Capsular saccharides will generally be used in the form of oligosaccharides. These are conveniently formed by fragmentation of purified capsular polysaccharide (e.g. by hydrolysis), which will usually be followed by purification of the fragments of the desired size.

Fragmentation of polysaccharides is preferably performed to give a final average degree of polymerisation (DP) in the oligosaccharide of less than 30 (e.g. between 10 and 20, preferably around 10 for serogroup A; between 15 and 25 for serogroups W135 and Y, preferably around 15-20; between 12 and 22 for serogroup C; etc.). DP can conveniently be measured by ion exchange chromatography or by colorimetric assays [81].

If hydrolysis is performed, the hydrolysate will generally be sized in order to remove short-length oligosaccharides [29]. This can be achieved in various ways, such as ultrafiltration followed by ion-exchange chromatography. Oligosaccharides with a degree of polymerisation of less than or equal to about 6 are preferably removed for serogroup A, and those less than around 4 are preferably removed for serogroups W135 and Y.

Preferred MenC saccharide antigens are disclosed in reference 80, as used in Menjugate™.

The saccharide antigen may be chemically modified. This is particularly useful for reducing hydrolysis for serogroup A [82; see below]. De-O-acetylation of meningococcal saccharides can be performed. For oligosaccharides, modification may take place before or after depolymerisation.

Where a composition of the invention includes a MenA saccharide antigen, the antigen is preferably a modified saccharide in which one or more of the hydroxyl groups on the native saccharide has/have been replaced by a blocking group [82]. This modification improves resistance to hydrolysis.

The number of monosaccharide units having blocking groups can vary. For example, all or substantially all the monosaccharide units may have blocking groups. Alternatively, at least 10%, 20%, 30%, 40%, 50%, 60%, 70%, 80% or 90% of the monosaccharide units may have blocking groups. At least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 monosaccharide units may have blocking groups.

Likewise, the number of blocking groups on a monosaccharide unit may vary. For example, the number of blocking groups on a monosaccharide unit may be 1 or 2. The blocking group will generally be at the 4 position and/or 3-position of the monosaccharide units.

The terminal monosaccharide unit may or may not have a blocking group instead of its native hydroxyl. It is preferred to retain a free anomeric hydroxyl group on a terminal monosaccharide unit in order to provide a handle for further reactions (e.g. conjugation). Anomeric hydroxyl groups can be converted to amino groups (—$NH_2$ or —NH-E, where E is a nitrogen protecting group) by reductive amination (using, for example, $NaBH_3CN/NH_4Cl$), and can then be regenerated after other hydroxyl groups have been converted to blocking groups.

Blocking groups to replace hydroxyl groups may be directly accessible via a derivatizing reaction of the hydroxyl group i.e. by replacing the hydrogen atom of the hydroxyl group with another group. Suitable derivatives of hydroxyl groups which act as blocking groups are, for example, carbamates, sulfonates, carbonates, esters, ethers (e.g. silyl ethers or alkyl ethers) and acetals. Some specific examples of such blocking groups are allyl, Aloc, benzyl, BOM, t-butyl, trityl, TBS, TBDPS, TES, TMS, TIPS, PMB, MEM, MOM, MTM, THP, etc. Other blocking groups that are not directly accessible and which completely replace the hydroxyl group include $C_{1-12}$ alkyl, $C_{3-12}$ alkyl, $C_{5-12}$ aryl, $C_{5-12}$ aryl-$C_{1-6}$ alkyl, $NR^1R^2$ ($R^1$ and $R^2$ are defined in the following paragraph), H, F, Cl, Br, $CO_2H$, $CO_2(C_{1-6}alkyl)$, CN, $CF_3$, $CCl_3$, etc. Preferred blocking groups are electron-withdrawing groups.

Preferred blocking groups are of the formula: —O—X—Y or —$OR^3$ wherein: X is C(O), S(O) or $SO_2$; Y is $C_{1-12}$ alkyl, $C_{1-12}$ alkoxy, $C_{3-12}$ cycloalkyl, $C_{5-12}$ aryl or $C_{5-12}$ aryl-$C_{1-6}$ alkyl, each of which may optionally be substituted with 1, 2 or 3 groups independently selected from F, Cl, Br, $CO_2H$, $CO_2$($C_{1-6}$ alkyl), CN, $CF_3$ or $CCl_3$; or Y is $NR^1R^2$; $R^1$ and $R^2$ are independently selected from H, $C_{1-12}$ alkyl, $C_{3-12}$ cycloalkyl, $C_{5-12}$ aryl, $C_{5-12}$ aryl-$C_{1-6}$ alkyl; or $R^1$ and $R^2$ may be joined to form a $C_{3-12}$ saturated heterocyclic group; $R^3$ is $C_{1-12}$ alkyl or $C_{3-12}$ cycloalkyl, each of which may optionally be substituted with 1, 2 or 3 groups independently selected from F, Cl, Br, $CO_2(C_{1-6}$ alkyl), CN, $CF_3$ or $CCl_3$; or $R^3$ is $C_{5-12}$ aryl or $C_{5-12}$ aryl-$C_{1-6}$ alkyl, each of which may optionally be substituted with 1, 2, 3, 4 or 5 groups selected from F, Cl, Br, $CO_2H$, $CO_2(C_{1-6}$ alkyl), CN, $CF_3$ or $CCl_3$. When $R^3$ is $C_{1-12}$ alkyl or $C_{3-12}$ cycloalkyl, it is typically substituted with 1, 2 or 3 groups as defined above. When $R^1$ and $R^2$ are joined to form a $C_{3-12}$ saturated heterocyclic group, it is meant that $R^1$ and $R^2$ together with the nitrogen atom form a saturated heterocyclic group containing any number of carbon atoms between 3 and 12 (e.g. $C_3$, $C_4$, $C_5$, $C_6$, $C_7$, $C_8$, $C_9$, $C_{10}$, $C_{11}$, $C_{12}$). The heterocyclic group may contain 1 or 2 heteroatoms (such as N, O or S) other than the nitrogen atom. Examples of $C_{3-12}$ saturated heterocyclic groups are pyrrolidinyl, piperidinyl, morpholinyl, piperazinyl, imidazolidinyl, azetidinyl and aziridinyl.

Blocking groups —O—X—Y and —$OR^3$ can be prepared from —OH groups by standard derivatizing procedures, such as reaction of the hydroxyl group with an acyl halide, alkyl halide, sulfonyl halide, etc. Hence, the oxygen atom in —O—X—Y is preferably the oxygen atom of the hydroxyl group, while the —X—Y group in —O—X—Y preferably replaces the hydrogen atom of the hydroxyl group.

Alternatively, the blocking groups may be accessible via a substitution reaction, such as a Mitsonobu-type substitution. These and other methods of preparing blocking groups from hydroxyl groups are well known.

More preferably, the blocking group is —$OC(O)CF_3$ [83], or a carbamate group —$OC(O)NR^1R^2$, where $R^1$ and $R^2$ are independently selected from $C_{1-6}$ alkyl. More preferably, $R^1$ and $R^2$ are both methyl i.e. the blocking group is —$OC(O)NMe_2$. Carbamate blocking groups have a stabilizing effect on the glycosidic bond and may be prepared under mild conditions.

Preferred modified MenA saccharides contain n monosaccharide units, where at least h % of the monosaccharide units do not have —OH groups at both of positions 3 and 4. The value of h is 24 or more (e.g. 25, 26, 27, 28, 29, 30, 35, 40, 45, 50, 55, 60, 65, 70, 75, 80, 85, 90, 95, 98, 99 or 100) and is preferably 50 or more. The absent —OH groups are preferably blocking groups as defined above.

Other preferred modified MenA saccharides comprise monosaccharide units, wherein at least s of the monosaccharide units do not have —OH at the 3 position and do not have —OH at the 4 position. The value of s is at least 1 (e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90). The absent —OH groups are preferably blocking groups as defined above.

Suitable modified MenA saccharides for use with the invention have the formula:

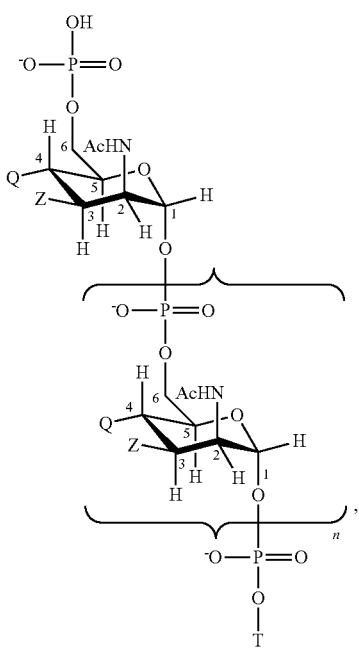

wherein
n is an integer from 1 to 100 (preferably an integer from 15 to 25);
T is of the formula (A) or (B):

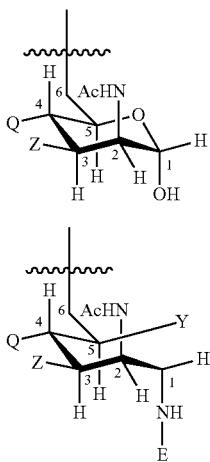

each Z group is independently selected from OH or a blocking group as defined above; and
each Q group is independently selected from OH or a blocking group as defined above;
Y is selected from OH or a blocking group as defined above;
E is H or a nitrogen protecting group;
and wherein more than about 7% (e.g. 8%, 9%, 10% or more) of the Q groups are blocking groups.

Each of the n+2 Z groups may be the same or different from each other. Likewise, each of the n+2 Q groups may be the same or different from each other. All the Z groups may be OH. Alternatively, at least 10%, 20, 30%, 40%, 50% or 60% of the Z groups may be OAc. Preferably, about 70% of the Z groups are OAc, with the remainder of the Z groups being OH or blocking groups as defined above. At least about 7% of Q groups are blocking groups. Preferably, at least 10%, 20%, 30%, 40%, 50%, 60%, 70%, 80%, 90% or even 100% of the Q groups are blocking groups.

Meningococcal capsular polysaccharides are typically prepared by a process comprising the steps of polysaccharide precipitation (e.g. using a cationic detergent), ethanol fractionation, cold phenol extraction (to remove protein) and ultracentrifugation (to remove LPS) [e.g. ref. 84]. A more preferred process [30], however, involves polysaccharide precipitation followed by solubilisation of the precipitated polysaccharide using a lower alcohol. Precipitation can be achieved using a cationic detergent such as tetrabutylammonium and cetyltrimethylammonium salts (e.g. the bromide salts), or hexadimethrine bromide and myristyltrimethylammonium salts. Cetyltrimethylammonium bromide ('CTAB') is particularly preferred [85]. Solubilisation of the precipitated material can be achieved using a lower alcohol such as methanol, propan-1-ol, propan-2-ol, butan-1-ol, butan-2-ol, 2-methyl-propan-1-ol, 2-methyl-propan-2-ol, diols, etc., but ethanol is particularly suitable for solubilising CTAB-polysaccharide complexes. Ethanol is preferably added to the precipitated polysaccharide to give a final concentration (based on total content of ethanol and water) of between 50% and 95%.

After re-solubilisation, the polysaccharide may be further treated to remove contaminants. This is particularly important in situations where even minor contamination is not acceptable (e.g. for human vaccine production). This will typically involve one or more steps of filtration e.g. depth filtration, filtration through activated carbon may be used, size filtration and/or ultrafiltration. Once filtered to remove contaminants, the polysaccharide may be precipitated for further treatment and/or processing. This can be conveniently achieved by exchanging cations (e.g. by the addition of calcium or sodium salts).

As an alternative to purification, capsular saccharides of the present invention may be obtained by total or partial synthesis e.g. Hib synthesis is disclosed in ref. 86, and MenA synthesis in ref. 87.

Compositions of the invention comprise capsular saccharides from at least two serogroups of N. meningitidis. The saccharides are preferably prepared separately (including any fragmentation, conjugation, modification, etc.) and then admixed to give a composition of the invention.

Where the composition comprises capsular saccharide from serogroup A, however, it is preferred that the serogroup A saccharide is not combined with the other saccharide(s) until shortly before use, in order to minimise the potential for hydrolysis. This can conveniently be achieved by having the serogroup A component (typically together with appropriate excipients) in lyophilised form and the other serogroup component(s) in liquid form (also with appropriate excipients), with the liquid components being used to reconstitute the lyophilised MenA component when ready for use. Where an aluminium salt adjuvant is used, it is preferred to include the adjuvant in the vial containing the with the liquid vaccine, and to lyophilise the MenA component without adjuvant.

A composition of the invention may thus be prepared from a kit comprising: (a) capsular saccharide from *N. meningitidis* serogroup A, in lyophilised form; and (b) the further antigens from the composition, in liquid form. The invention also provides a method for preparing a composition of the invention, comprising mixing a lyophilised capsular saccharide from *N. meningitidis* serogroup A with the further antigens, wherein said further antigens are in liquid form.

The invention also provides a kit comprising: (a) a first container containing capsular saccharides from two or more of *N. meningitidis* serogroups C, W135 and Y, all in lyophilised form; and (b) a second container containing in liquid form (i) a composition which, after administration to a subject, is able to induce an antibody response in that subject, wherein the antibody response is bactericidal against two or more (e.g. 2 or 3) of hypervirulent lineages A4, ET-5 and lineage 3 of *N. meningitidis* serogroup B, (ii) capsular saccharides from none or one of *N. meningitidis* serogroups C, W135 and Y, and optionally (iii) further antigens (see below) that do not include meningococcal capsular saccharides, wherein, reconstitution of the contents of container (a) by the contents of container (b) provides a composition of the invention.

Within each dose, the amount of an individual saccharide antigen will generally be between 1-50 µg (measured as mass of saccharide), with about 2.5 µg, 5 µg or 10 µg of each being preferred. With A:C:W135:Y weight ratios of 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1, therefore, the amount represented by the number 1 is preferably about 2.5 µg, 5 µg or 10 µg. For a 1:1:1:1 ratio A:C:W:Y composition and a 10 µg per saccharide, therefore, 40 µg saccharide is administered per dose. Preferred compositions have about the following µg saccharide per dose:

| A | 10 | 0 | 0 | 0 | 10 | 5 | 2.5 |
|---|----|----|----|-----|----|----|-----|
| C | 10 | 10 | 5 | 2.5 | 5 | 5 | 2.5 |
| W135 | 10 | 10 | 5 | 2.5 | 5 | 5 | 2.5 |
| Y | 10 | 10 | 5 | 2.5 | 5 | 5 | 2.5 |

Preferred compositions of the invention comprise less than 50 µg meningococcal saccharide per dose. Other preferred compositions comprise ≤40 µg meningococcal saccharide per dose. Other preferred compositions comprise ≤30 µg meningococcal saccharide per dose. Other preferred compositions comprise ≤5 µg meningococcal saccharide per dose. Other preferred compositions comprise ≤0 µg meningococcal saccharide per dose. Other preferred compositions comprise ≤10 µg meningococcal saccharide per dose but, ideally, compositions of the invention comprise at least 10 µg meningococcal saccharide per dose.

The Menjugate™ and NeisVac™ MenC conjugates use a hydroxide adjuvant, whereas Meningitec™ uses a phosphate. It is possible in compositions of the invention to adsorb some antigens to an aluminium hydroxide but to have other antigens in association with an aluminium phosphate. For tetravalent serogroup combinations, for example, the following permutations are available:

| Serogroup | Aluminium salt (H = a hydroxide; P = a phosphate) | | | | | | | | | | | | | | |
|---|---|---|---|---|---|---|---|---|---|---|---|---|---|---|---|
| A | P | H | P | H | H | H | P | P | P | H | H | H | P | P | P | H |
| C | P | H | H | P | H | H | P | H | H | P | P | H | P | H | P | P |
| W135 | P | H | H | H | P | H | H | P | H | H | P | P | P | P | H | P |
| Y | P | H | H | H | H | P | H | H | P | P | H | P | H | P | P | P |

For trivalent *N. meningitidis* serogroup combinations, the following permutations are available:

| Serogroup | Aluminium salt (H = a hydroxide; P = a phosphate) | | | | | | | |
|---|---|---|---|---|---|---|---|---|
| C | P | H | H | H | P | P | P | H |
| W135 | P | H | H | P | H | P | H | P |
| Y | P | H | P | H | H | H | P | P |

*Haemophilus influenzae* Type B

Where the composition includes a *H. influenzae* type B antigen, it will typically be a Hib capsular saccharide antigen. Saccharide antigens from *H. influenzae* b are well known.

Advantageously, the Hib saccharide is covalently conjugated to a carrier protein, in order to enhance its immunogenicity, especially in children. The preparation of polysaccharide conjugates in general, and of the Hib capsular polysaccharide in particular, is well documented [e.g. references 88 to 96 etc.]. The invention may use any suitable Hib conjugate. Suitable carrier proteins are described below, and preferred carriers for Hib saccharides are $CRM_{197}$ ('HbOC'), tetanus toxoid ('PRP-T') and the outer membrane complex of *N. meningitidis* ('PRP-OMP').

The saccharide moiety of the conjugate may be a polysaccharide (e.g. full-length polyribosylribitol phosphate (PRP)), but it is preferred to hydrolyse polysaccharides to form oligosaccharides (e.g. MW from ~1 to ~5 kDa).

A preferred conjugate comprises a Hib oligosaccharide covalently linked to $CRM_{197}$ via an adipic acid linker [97, 98]. Tetanus toxoid is also a preferred carrier.

Compositions of the invention may comprise more than one Hib antigen.

Where a composition includes a Hib saccharide antigen, it is preferred that it does not also include an aluminium hydroxide adjuvant. If the composition includes an aluminium phosphate adjuvant then the Hib antigen may be adsorbed to the adjuvant [99] or it may be non-adsorbed [100].

Hib antigens may be lyophilised e.g. together with meningococcal antigens.

*Streptococcus pneumoniae*

Where the composition includes a *S. pneumoniae* antigen, it will typically be a capsular saccharide antigen which is preferably conjugated to a carrier protein [e.g. refs. 31-33]. It is preferred to include saccharides from more than one serotype of *S. pneumoniae*. For example, mixtures of polysaccharides from 23 different serotype are widely used, as are conjugate vaccines with polysaccharides from between 5 and 11 different serotypes [101]. For example, PrevNar™ [102] contains antigens from seven serotypes (4, 6B, 9V, 14, 18C, 19F, and 23F) with each saccharide individually conjugated to $CRM_{197}$ by reductive amination, with 2 µg of each saccharide per 0.5 ml dose (4 µg of serotype 6B), and with conjugates adsorbed on an aluminium phosphate adjuvant. Compositions of the invention preferably include at least serotypes 6B, 14, 19F and 23F. Conjugates may be adsorbed onto an aluminium phosphate.

As an alternative to using saccharide antigens from pneumococcus, the composition may include one or more polypeptide antigens. Genome sequences for several strains of pneumococcus are available [103, 104] and can be subjected to reverse vaccinology [105-108] to identify suitable polypeptide antigens [109, 110]. For example, the composition may include one or more of the following antigens: PhtA, PhtD, PhtB, PhtE, SpsA, LytB, LytC, LytA, Sp125, Sp101, Sp128 and Sp130, as defined in reference 111.

In some embodiments, the composition may include both saccharide and polypeptide antigens from pneumococcus. These may be used in simple admixture, or the pneumococcal saccharide antigen may be conjugated to a pneumococcal protein. Suitable carrier proteins for such embodiments include the antigens listed in the previous paragraph [111].

Pneumococcal antigens may be lyophilised e.g. together with meningococcal and/or Hib antigens.

Covalent Conjugation

Capsular saccharides in compositions of the invention will usually be conjugated to carrier protein(s). In general, conjugation enhances the immunogenicity of saccharides as it converts them from T-independent antigens to T-dependent antigens, thus allowing priming for immunological memory. Conjugation is particularly useful for paediatric vaccines and is a well known technique [e.g. reviewed in refs. 112 and 88-96].

Preferred carrier proteins are bacterial toxins or toxoids, such as diphtheria toxoid or tetanus toxoid. The $CRM_{197}$ mutant diphtheria toxin [79, 113, 114] is particularly preferred. Other suitable carrier proteins include the *N. meningitidis* outer membrane protein [68], synthetic peptides [69, 70], heat shock proteins [71, 72], pertussis proteins [73, 74], cytokines [76], lymphokines [76], hormones [76], growth factors [76], artificial proteins comprising multiple human $CD4^+$ T cell epitopes from various pathogen-derived antigens [115], protein D from *H. influenzae* [75, 116], pneumococcal surface protein PspA [117], iron-uptake proteins [78], toxin A or B from *C. difficile* [77], etc. Preferred carriers are diphtheria toxoid, tetanus toxoid, *H. influenzae* protein D, and $CRM_{197}$.

Within a composition of the invention, it is possible to use more than one carrier protein e.g. to reduce the risk of carrier suppression. Thus different carrier proteins can be used for different serogroups e.g. serogroup A saccharides might be conjugated to $CRM_{197}$ while serogroup C saccharides might be conjugated to tetanus toxoid. It is also possible to use more than one carrier protein for a particular saccharide antigen e.g. serogroup A saccharides might be in two groups, with some conjugated to $CRM_{197}$ and others conjugated to tetanus toxoid. In general, however, it is preferred to use the same carrier protein for all saccharides.

A single carrier protein might carry more than one saccharide antigen [118]. For example, a single carrier protein might have conjugated to it saccharides from serogroups A and C. To achieve this goal, saccharides can be mixed prior to the conjugation reaction. In general, however, it is preferred to have separate conjugates for each serogroup.

Conjugates with a saccharide:protein ratio (w/w) of between 1:5 (i.e. excess protein) and 5:1 (i.e. excess saccharide) are preferred. Ratios between 1:2 and 5:1 are preferred, as are ratios between 1:1.25 and 1:2.5 are more preferred. Excess carrier protein is preferred for MenA and MenC.

Conjugates may be used in conjunction with free carrier protein [119]. When a given carrier protein is present in both free and conjugated form in a composition of the invention, the unconjugated form is preferably no more than 5% of the total amount of the carrier protein in the composition as a whole, and more preferably present at less than 2% by weight.

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [120, 121, etc.]). Other suitable techniques use carbodiimides, hydrazides, active esters, norborane, p-nitrobenzoic acid, N-hydroxysuccinimide, S-NHS, EDC, TSTU; see also the introduction to reference 94).

Linkages via a linker group may be made using any known procedure, for example, the procedures described in references 122 and 123. One type of linkage involves reductive amination of the polysaccharide, coupling the resulting amino group with one end of an adipic acid linker group, and then coupling a protein to the other end of the adipic acid linker group [92, 124, 125]. Other linkers include B-propionamido [126], nitrophenyl-ethylamine [127], haloacyl halides [128], glycosidic linkages [129], 6-aminocaproic acid [130], ADH [131], $C_4$ to $C_{12}$ moieties [132] etc. As an alternative to using a linker, direct linkage can be used. Direct linkages to the protein may comprise oxidation of the polysaccharide followed by reductive amination with the protein, as described in, for example, references 133 and 134.

A process involving the introduction of amino groups into the saccharide (e.g. by replacing terminal =O groups with $—NH_2$) followed by derivatisation with an adipic diester (e.g. adipic acid N-hydroxysuccinimido diester) and reaction with carrier protein is preferred. Another preferred reaction uses CDAP activation with a protein D carrier e.g. for MenA or MenC.

After conjugation, free and conjugated saccharides can be separated. There are many suitable methods, including hydrophobic chromatography, tangential ultrafiltration, diafiltration etc. [see also refs. 135 & 136, etc.].

Where the composition of the invention includes a conjugated oligosaccharide, it is preferred that oligosaccharide preparation precedes conjugation.

Outer Membrane Vesicles

It is preferred that compositions of the invention should not include complex or undefined mixtures of antigens, which are typical characteristics of OMVs. However, one way in which the invention can be applied to OMVs is where OMVs are to be administered in a multiple dose schedule.

Where more than one OMV dose is to be administered, each dose may be supplemented (either by adding the purified protein or by expression of the protein within the bacteria from which the OMVs are derived) by one of the first protein, second protein or third protein as defined above. Preferably different doses are supplemented with different NMB1870 variants. In a three dose OMV schedule, for example, each dose could contain a different one of the first protein, second protein and third protein such that, after receiving three doses of OMVs, all three variants have been received. In a two dose OMV schedule, one variant could be used per OMV dose (thus omitting one variant), or one or both OMV doses could be supplemented with more than one variant in order to give coverage with all three variants. In preferred embodiments, there are three OMV doses, and each of the three OMV doses contains three different genetically-engineered vesicle populations each displaying three subtypes, thereby giving nine different subtypes in all.

This approach may be used in general to improve preparations of *N. meningitidis* serogroup B microvesicles [137], 'native OMVs' [138], blebs or outer membrane vesicles [e.g. refs. 139 to 144, etc.]. These may be prepared from bacteria which have been genetically manipulated [145-148] e.g. to increase immunogenicity (e.g. hyper-express immunogens), to reduce toxicity, to inhibit capsular polysaccharide synthesis, to down-regulate PorA expression, etc. They may be prepared from hyperblebbing strains [149-152]. Vesicles from a non-pathogenic *Neisseria* may be included [153]. OMVs may be prepared without the use of detergents [154, 155]. They may express non-Neisserial proteins on their surface [156]. They may be LPS-depleted. They may be mixed with recombinant antigens [139, 157]. Vesicles from bacteria with different class I outer membrane protein subtypes may be used e.g. six different subtypes [158, 159] using two different genetically-engineered vesicle populations each displaying three subtypes, or nine different subtypes using three different genetically-engineered vesicle populations each displaying three subtypes, etc. Useful subtypes include: P1.7, 16; P1.5-1,2-2; P1,19,15-1; P1.5-2,10; P1.12-1,13; P1.7-2,4; P1.22,14; P1.7-1,1; P1.18-1,3,6.

It is also possible, of course, to supplement vesicle preparations with two or three different variants.

Immunisation

The composition of the invention is preferably an immunogenic composition, and the invention provides an immunogenic composition of the invention for use as a medicament.

The invention also provides a method for raising an antibody response in a mammal, comprising administering an immunogenic composition of the invention to the mammal. The antibody response is preferably a protective and/or bactericidal antibody response.

The invention also provides a method for protecting a mammal against a Neisserial (e.g. meningococcal) infection, comprising administering to the mammal an immunogenic composition of the invention.

The invention also provides the use of at least two of antigens (a), (b) and (c) as defined above in the manufacture of a medicament for preventing Neisserial (e.g. meningococcal) infection in a mammal.

The mammal is preferably a human. The human may be an adult or, preferably, a child.

Immunogenic compositions of the invention may be used therapeutically (i.e. to treat an existing infection) or prophylactically (i.e. to prevent future infection).

The uses and methods are particularly useful for preventing/treating diseases including, but not limited to, meningitis (particularly bacterial meningitis) and bacteremia.

Efficacy of therapeutic treatment can be tested by monitoring Neisserial infection after administration of the composition of the invention. Efficacy of prophylactic treatment can be tested by monitoring immune responses against NMB1870 after administration of the composition. Immunogenicity of compositions of the invention can be determined by administering them to test subjects (e.g. children 12-16 months age, or animal models [160]) and then determining standard parameters including serum bactericidal antibodies (SBA) and ELISA titres (GMT) of total and high-avidity anti-capsule IgG. These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

The immunogenic composition of the invention will generally include a pharmaceutically acceptable carrier, which can be any substance that does not itself induce the production of antibodies harmful to the patient receiving the composition, and which can be administered without undue toxicity. Suitable carriers can be large, slowly-metabolised macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers can include liquids such as water, saline, glycerol and ethanol. Auxiliary substances, such as wetting or emulsifying agents, pH buffering substances, and the like, can also be present in such vehicles. Liposomes are suitable carriers. A thorough discussion of pharmaceutical carriers is available in ref. 161.

Neisserial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops.

The composition is preferably sterile. It is preferably pyrogen-free. It is preferably buffered e.g. at between pH 6 and pH 8, generally around pH 7. Where a composition comprises an aluminium hydroxide salt, it is preferred to use a histidine buffer [162]. Compositions of the invention may be isotonic with respect to humans.

Immunogenic compositions comprise an immunologically effective amount of immunogen, as well as any other of other specified components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses). The composition may be administered in conjunction with other immunoregulatory agents.

An immunogenic composition will generally include an adjuvant. Preferred adjuvants to enhance effectiveness of the composition include, but are not limited to: (A) MF59 (5% Squalene, 0.5% Tween 80, and 0.5% Span 85, formulated into submicron particles using a microfluidizer) [see Chapter 10 of ref. 163; see also ref. 164]; (B) microparticles (i.e. a particle of ~100 nm to ~154 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone etc.), with poly(lactide-co-glycolide) being preferred ('PLG'), optionally having a charged surface (e.g. by adding a cationic, anionic, or nonionic detergent such as SDS (negative) or CTAB (positive) [e.g. refs. 165 & 166]); (C) liposomes [see Chapters 13 and 14 of ref. 163]; (D) ISCOMs [see Chapter 23 of ref. 163], which may be devoid of additional detergent [167]; (E) SAF, containing 10% Squalane, 0.4% Tween 80, 5% pluronic-block polymer L121, and thr-MDP, either microfluidized into a submicron emulsion or vortexed to generate a larger particle size emulsion [see Chapter 12 of ref. 163]; (F) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (G) saponin adjuvants, such as QuilA or QS21 [see Chapter 22 of ref. 163], also known as Stimulon™; (H) chitosan [e.g. 168]; (I) complete Freund's adjuvant (CFA) and incomplete Freund's adjuvant (IFA); (J) cytokines, such as interleukins (e.g. IL-1, IL-2, IL-4, IL-5, IL-6, IL-7, IL-12, etc.), interferons (e.g. interferon-γ), macrophage colony stimulating factor, tumor necrosis factor, etc. [see Chapters 27 & 28 of ref. 163], RC529; (K) a saponin (e.g. QS21)+3dMPL+IL-12 (optionally+a sterol) [169]; (L) monophosphoryl lipid A (MPL) or 3-O-deacylated MPL (3dMPL) [e.g. chapter 21 of ref. 163]; (M) combinations of 3dMPL with, for example, QS21 and/or oil-in-water emulsions [170]; (N) oligonucleotides comprising CpG motifs [171] i.e. containing at least one CG dinucleotide, with 5-methylcytosine optionally being used in place of cytosine; (O) a polyoxyethylene ether or a polyoxyethylene ester [172]; (P) a polyoxyethylene sorbitan ester surfactant in combination with an octoxynol [173] or a polyoxyethylene alkyl ether or ester surfactant in combination with at least one additional non-ionic surfactant such as an octoxynol [174]; (O) an immunostimulatory oligonucleotide (e.g. a CpG oligonucleotide) and a saponin [175]; (R) an immunostimulant and a particle of metal salt [176]; (S) a saponin and an oil-in-water emulsion [177]; (T) $E.\ coli$ heat-labile enterotoxin ("LT"), or detoxified mutants thereof, such as the K63 or R72 mutants [e.g. Chapter 5 of ref. 38]; (U) cholera toxin ("CT"), or detoxified mutants thereof [e.g. Chapter 5 of ref. 38]; (V) double-stranded RNA; (W) aluminium salts, such as aluminium hydroxides (including oxyhydroxides), aluminium phosphates (including hydroxyphosphates), aluminium sulfate, etc [Chapters 8 & 9 in ref. 163] or calcium salts, such as calcium phosphate; and (X) other substances that act as immunostimulating agents to enhance the effectiveness of the composition [e.g. see Chapter 7 of ref. 163]. Aluminium salts (aluminium phosphates and particularly hydroxyphosphates, and/or hydroxides and particularly oxyhydroxide) and MF59 are preferred adjuvants for parenteral immunisation. Toxin mutants are preferred mucosal adjuvants. QS21 is another useful adjuvant for NMB1870, which may be used alone or in combination with any of (A) to (X) e.g. with an aluminium salt.

Muramyl peptides include N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine MTP-PE), etc.

Protein Expression

Bacterial expression techniques are known in the art. A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in $Escherichia\ coli$ ($E.\ coli$) [Raibaud et al. (1984) $Annu.\ Rev.\ Genet.$ 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) $Nature$ 198:1056], and maltose. Additional examples include promoter sequences derived from biosynthetic enzymes such as tryptophan (trp) [Goeddel et al. (1980) $Nuc.\ Acids\ Res.$ 8:4057; Yelverton et al. (1981) $Nucl.\ Acids\ Res.$ 9:731; U.S. Pat. No. 4,738,921; EP-A-0036776 and EP-A-0121775]. The β-lactamase (bla) promoter system [Weissmann (1981) "The cloning of interferon and other mistakes." In $Interferon$ 3 (ed. I. Gresser)], bacteriophage lambda PL [Shimatake et al. (1981) $Nature$ 292:128] and T5 [U.S. Pat. No. 4,689,406] promoter systems also provide useful promoter sequences. Another promoter of interest is an inducible arabinose promoter (pBAD).

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21] Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *Proc Natl. Acad. Sci.* 82:1074]. In addition, a hybrid promoter can also be comprised of a bacteriophage promoter and an *E. coli* operator region (EPO-A-0 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli*." In *Molecular Cloning: A Laboratory Manual*].

A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EP-A-0219237).

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (e.g. plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (EP-A-0127328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia, the following bacteria: *Bacillus subtilis* [Palva et al. (1982) *Proc. Natl. Acad. Sci. USA* 79:5582; EP-A-0 036 259 and EP-A-0 063 953; WO 84/04541], *Escherichia coli* [Shimatake et al. (1981) *Nature* 292:128; Amann et al. (1985) *Gene* 40:183; Studier et al. (1986) *J. Mol. Biol.* 189:113; EP-A-0 036 776, EP-A-0 136 829 and EP-A-0 136 907], *Streptococcus cremoris* [Powell et al. (1988) *Appl. Environ. Microbiol.* 54:655]; *Streptococcus lividans* [Powell et al. (1988) *Appl. Environ. Microbiol.* 54:655], *Streptomyces lividans* [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g. [Masson et al. (1989) *FEMS Microbiol. Lett.* 60:273; Palva et al. (1982) *Proc. Natl. Acad. Sci. USA* 79:5582; EP-A-0 036 259 and EP-A-0 063 953; WO 84/04541, *Bacillus*], [Miller et al. (1988) *Proc. Natl. Acad. Sci* 85:856; Wang et al. (1990) *J. Bacterial.* 172:949, *Campylobacter*], [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318; *Escherichia*], [Chassy et al. (1987) *FEMS Microbiol. Lett.* 44:173 *Lactobacillus*]; [Fiedler et al. (1988) *Anal. Biochem* 170:38, *Pseudomonas*]; [Augustin et al. (1990) *FEMS Microbiol. Lett.* 66:203, *Staphylococcus*], [Barany et al. (1980) *J. Bacteriol.* 144:698; Harlander (1987)

"Transformation of *Streptococcus* lactis by electroporation, in: *Streptococcal Genetics* (ed. J. Ferretti and R. Curtiss III); Perry et al. (1981) *Infect. Immun.* 32:1295; Powell et al. (1988) *Appl. Environ. Microbiol.* 54:655; Somkuti et al. (1987) *Proc. 4th Evr. Cong. Biotechnology* 1:412, *Streptococcus].*

Disclaimers

The invention preferably excludes: (a) amino acid and nucleic acid sequences available in public sequence databases (e.g. GenBank or GENESEQ) prior to 22 Nov. 2002; (b) amino acid and nucleic acid sequences disclosed in patent applications having a filing date or, where applicable, a priority date prior to 22 Nov. 2002. In particular, SEQ ID entries in the any of the references cited herein may be excluded e.g. reference 13.

General

The term "comprising" means "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

'Sequence identity' is preferably determined by the Smith-Waterman homology search algorithm as implemented in the MPSRCH program (Oxford Molecular), using an affine gap search with parameters gap open penalty=12 and gap extension penalty=1.

After serogroup, meningococcal classification includes serotype, serosubtype and then immunotype, and the standard nomenclature lists serogroup, serotype, serosubtype, and immunotype, each separated by a colon e.g. B:4:P1.15:L3,7, 9. Within serogroup B, some lineages cause disease often (hyperinvasive), some lineages cause more severe forms of disease than others (hypervirulent), and others rarely cause disease at all. Seven hypervirulent lineages are recognised, namely subgroups I, III and IV-1, ET-5 complex, ET-37 complex, A4 cluster and lineage 3. These have been defined by multilocus enzyme electrophoresis (MLEE), but multilocus sequence typing (MLST) has also been used to classify meningococci [ref. 16]. The four main hypervirulent clusters are ST32, ST44, ST8 and ST11 complexes.

The term "alkyl" refers to alkyl groups in both straight and branched forms, The alkyl group may be interrupted with 1, 2 or 3 heteroatoms selected from —O—, —NH— or —S—. The alkyl group may also be interrupted with 1, 2 or 3 double and/or triple bonds. However, the term "alkyl" usually refers to alkyl groups having no heteroatom interruptions or double or triple bond interruptions. Where reference is made to $C_{1-12}$ alkyl, it is meant the alkyl group may contain any number of carbon atoms between 1 and 12 (e.g. $C_1$, $C_2$, $C_3$, $C_4$, $C_5$, $C_6$, $C_7$, $C_8$, $C_9$, $C_{10}$, $C_{11}$, $C_{12}$). Similarly, where reference is made to $C_{1-6}$ alkyl, it is meant the alkyl group may contain any number of carbon atoms between 1 and 6 (e.g. $C_1$, $C_2$, $C_3$, $C_4$, $C_5$, $C_6$).

The term "cycloalkyl" includes cycloalkyl, polycycloalkyl, and cycloalkenyl groups, as well as combinations of these with alkyl groups, such as cycloalkylalkyl groups. The cycloalkyl group may be interrupted with 1, 2 or 3 heteroatoms selected from —O—, —NH— or —S—. However, the term "cycloalkyl" usually refers to cycloalkyl groups having no heteroatom interruptions Examples of cycloalkyl groups include cyclopentyl, cyclohexyl, cyclohexenyl, cyclohexylmethyl and adamantyl groups. Where reference is made to $C_{3-12}$ cycloalkyl, it is meant that the cycloalkyl group may contain any number of carbon atoms between 3 and 12 (e.g. $C_3$, $C_4$, $C_5$, $C_6$, $C_7$, $C_8$, $C_9$, $C_{10}$, $C_{11}$, $C_{12}$).

The term "aryl" refers to an aromatic group, such as phenyl or naphthyl. Where reference is made to $C_{5-12}$ aryl, it is meant that the aryl group may contain any number of carbon atoms between 5 and 12 (e.g. $C_5$, $C_6$, $C_7$, $C_8$, $C_9$, $C_{10}$, $C_{11}$, $C_{12}$).

The term "$C_{5-12}$ aryl-$C_{1-6}$ alkyl" refers to groups such as benzyl, phenylethyl and naphthylmethyl.

Nitrogen protecting groups include silyl groups (such as TMS, TES, TBS, TIPS), acyl derivatives (such as phthalimides, trifluoroacetamides, methoxycarbonyl, ethoxycarbonyl, t-butoxycarbonyl (Boc), benzyloxycarbonyl (Z or Cbz), 9-fluorenylmethoxycarbonyl (Fmoc), 2-(trimethylsilyl) ethoxy carbonyl, 2,2,2-trichloroethoxycarbonyl (Troc)), sulfonyl derivatives (such as β-trimethylsilylethanesulfonyl (SES)), sulfenyl derivatives, $C_{1-12}$ alkyl, benzyl, benzhydryl, trityl, 9-phenylfluorenyl etc. A preferred nitrogen protecting group is Fmoc.

BRIEF DESCRIPTION OF DRAWINGS

FIG. 10 is a sequence alignment of variant 1 (MC58), variant 2 (961-5945), and variant 3 (M1239). Amino acid numbers initiate from the cysteine predicted to be the first amino acid of the mature protein. Grey and black backgrounds indicate conserved and identical residues, respectively.

FIG. 11 shows FACS analysis of sera against variant 1 (first row), variant 2 (second row), and variant 3 (third row), using the type strain of variant 1 (MC58), variant 2 (961-5945) and variant 3 (M1239). Control sera against the capsular polysaccharide is shown in row 4 (monoclonal antibody Seam3). Control serum against a cytoplasmic protein is shown in row 5 (anti-NMB1380). Row 6 contains the knock out mutants (KO) of each type strain, probed with the homologous antiserum.

MODES FOR CARRYING OUT THE INVENTION

NMB1870 in Serogroup B Strain MC58—Identification of the Start Codon

The NMB1870 gene was identified in the genome sequences of MenB and MenA published by The Institute for Genomic Research (TIGR) and Sanger Center, respectively [2, 4; NMB1870 and NMA0586]. However, there is a discrepancy over the position of the ATG start codon as the MenB start codon is 120 bp upstream of the MenA start codon. In contrast to both prior art annotations, the present invention places the start codon as a GTG codon which is downstream of the prior art start codons (18 bp downstream for MenA, 138 bp for MenB) and agrees with reference 8.

Figure 1:
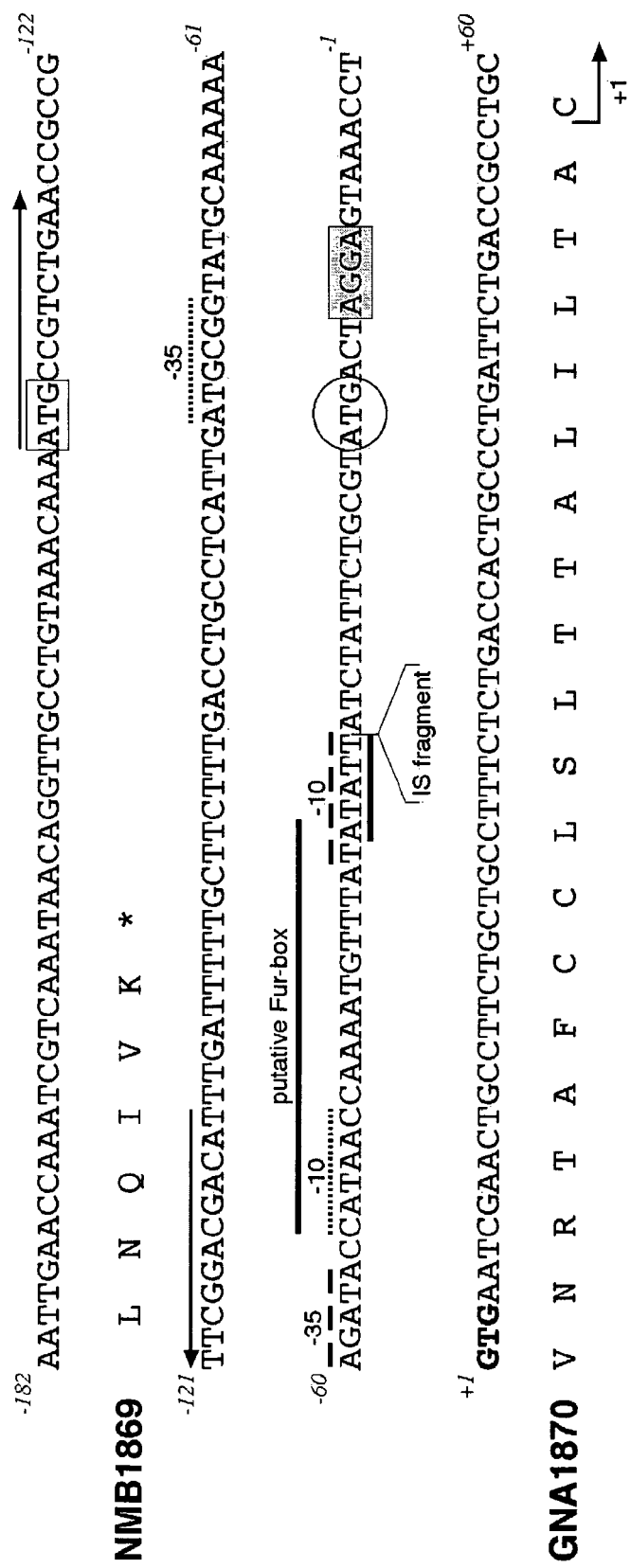
FIG. 1 shows the nucleotide sequence of the upstream region of NMB1870.

As shown in FIG. 1, the GTG start (+1) is consistent with the presence of a correctly spaced ribosome-binding site and with the prediction of the lipoprotein signature. The prior art TIGR MenB start codon is shown in a box, and the Sanger MenA start codon is in a circle. Inverted repeats are shown by horizontal arrows.

NMB1870 is a monocistronic gene located 157 bases downstream the stop codon of the fructose-bisphosphate aldolase gene nmb1869. In MenA Z2491 the overall organisation is similar, but 31 base pairs upstream from the GTG starting codon there is an insertion of 186 nucleotides which are homologous to an internal repeat region of IS1106 and are flanked by two 16 base pairs inverted repeats. A putative ribosome binding site (shaded) is present 8 bp upstream from the GTG starting codon. A fur box (11/19 matches with the *E. coli* fur box consensus [178]; SEQ ID NO$^S$: 74 & 75) is located 35 bp upstream of the start codon, as predicted by GCG FindPatterns starting from SEQ ID NO: 75 and allowing a maximum of nine mismatches. Putative promoter sequences were also detected.

The GCG Wisconsin Package suite (version 10.0) was used for computer sequence analysis of gene and protein sequences. The PSORT program [179] was used for localisation prediction. NMB1870 has the typical signature of a surface-exposed lipoprotein, characterised by a signal peptide with a lipo-box motif of the type -Leu-X-X-Cys-, where the Cysteine was followed by a Serine, an amino acid generally associated with outer membrane localisation of lipoproteins [180]. The lipo-box is lost in gonococcus due to a frame-shifting single base (G) insertion after MC58 nucleotide 36, with the correct reading frame being re-established by a 8 bp insertion after position 73.

The mature MC58 protein is predicted to be a lipoprotein with a molecular weight of 26,964 Dal and a pI of 7.96, and is characterised by the presence of four glycines downstream of the Lipo-box motif.

Secondary structure prediction analysis using the Predict-Protein software [181] indicates that NMB1870 is a globular protein mostly composed of beta sheets.

Sequence Analysis

Figure 2:
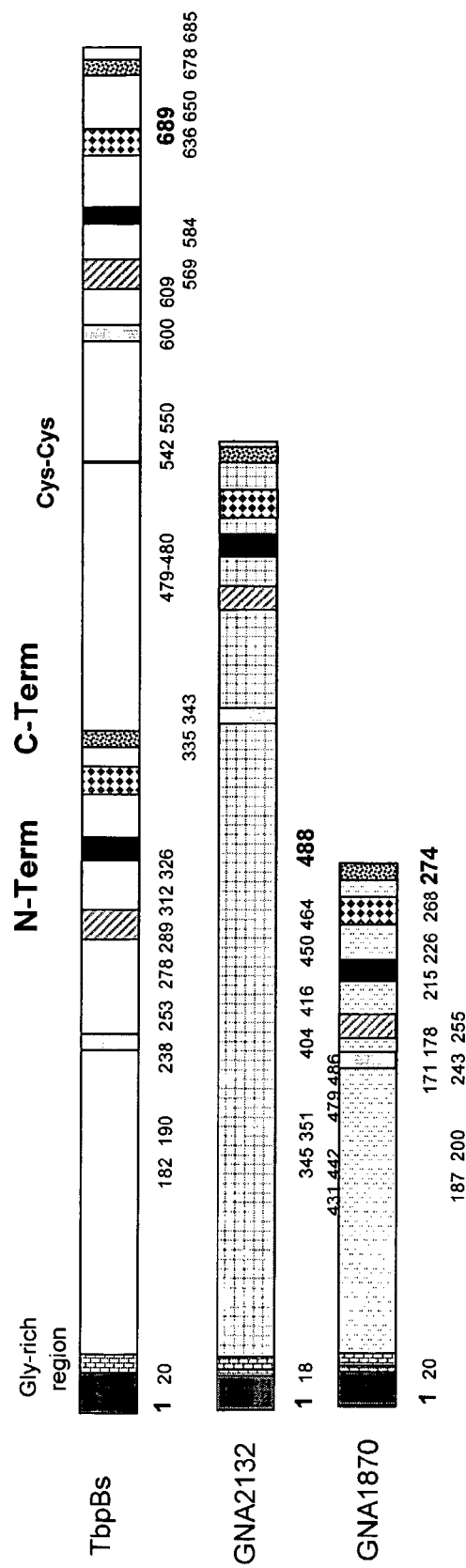
FIG. 2 is a schematic representation of the structure of TbpB proteins and of antigens NMB2132 and NMB1870. The leader peptides and proximal glycine-rich regions are indicated. Five conserved boxes are indicated by different motifs and their positions are mapped on the protein sequence.

The PSI-BLAST algorithm was used for homology searches [182] using the non-redundant protein database. No homologous proteins were found by searching existing non-redundant prokaryotic and eukaryotic protein databases maintained at the NCBI site, including the human genome, suggesting that NMB1870 is specific for *Neisseria*. However, a domain with some homology (28% identity over 146 amino acids) was found with the C-terminal portion of the transferrin-binding protein TfbA of *Actinobacillus pleuropneumoniae* [183] (FIG. 2). A closer look at this domain revealed homologies also with the transferrin-binding proteins from *N. meningitidis* [184], *H. influenzae* [185], *Moraxella catarrhalis* [186] and with the *N. meningitidis* surface antigen NMB2132, previously annotated as TbpB homologue [3].

To see if this sequence homology reflects a functional homology, recombinant NMB1870 (see below), human transferrin hTF (Sigma T-4132) and the mix of the two (final concentration of 7 µM) were dialysed O/N in PBS at 4° C. Following dialysis 20 µl of each protein and the mixture of them were loaded on a HPLC Superdex 200 PC 3.2/30 gel filtration column (Amersham) using PBS as running buffer [187]. Blue Dextran 2000 and the molecular weight standards ribonuclease A, chymotrypsin A, ovalbumin A, bovine serum albumin (Amersham) were used to calibrate the column. Gel filtration was performed using a Smart system with a flow rate of 0.04 ml/min and the eluted material monitored at 214 nm and 280 nm. (The NMB1870 retention volume was 1.68 ml and 1.47 ml for htf.) Fractions of 40 µl were collected and analysed by SDS-PAGE. The MC58 recombinant transferrin-binding protein 2 (Tbp2) was used as positive control.

The recombinant protein failed to bind human transferrin in vitro.

The Fur box in the promoter suggests that the expression of NMB1870 may be regulated by iron. However, expression of the protein does not seem to increase in low iron conditions.

An interesting feature of the protein is the presence of a stretch of four glycines downstream from the lipidated cysteine. Three or more consecutive glycines downstream from a lipidated cysteine are present also in other five lipoproteins in *N. meningitidis*, namely the transferrin-binding protein B (TbpB), the outer membrane component of an ABC transporter NMB0623, the hypothetical protein NMB1047, the TbpB homologue NMB2132, and the AspA lipoprotein [188]. In none of these proteins the poly-glycine stretch is encoded by a poly-G tract, suggesting that this feature is not used to generate antigenic modulation.

A search for lipoproteins with a glycine-rich region was carried out on 22 complete genomic sequences retrieved at the NCBI site [189] using FindPatterns. The search retrieved 29 lipoproteins in some but not all bacterial species. The organisms with this type of lipoproteins include both Gram-negative and Gram-positive bacteria, including *Haemophilus influenzae, Enterococcus fetalis, Mycobacterium tuberculosis, Lysteria monocytogenes* and *Staphylococcus aureus*, while others such as *E. coli, Bacillus subtilis, Helicobacter pylori, Streptococcus pneumoniae, S. pyogenes* and *Vibrio cholerae* have none. Most of the lipoproteins with this signature belong to ABC transporters, followed by proteins of unknown function. Although this common feature in the primary structure suggests a common role for the glycine repeats, so far, the function is unknown. However, it may serve to guide the lipoproteins to a specific pathway of secretion and surface localisation [190].

Sequencing for Other Strains 70 strains representative of the genetic and geographic diversity of the *N. meningitidis* population were selected for further investigation of NMB1870. Strains derive from 19 different countries, 73% belong to serogroup B, and 32 were isolated in the last five years. The strain panel mostly includes serogroup B strains, a few strains of serogroups A, C, Y, W-135 and Z, and one strain each of *N. gonorrhoeae* and *N. cinerea*. Strains are disclosed in more detail in references 191 & 192. Some strains are available from the ATCC (e.g. strain MC58 is available under reference BAA-335).

The NMB1870 gene was amplified using primers external to the coding sequence (A1, SEQ ID 55; and B2, SEQ ID 56). About 10 ng of chromosomal DNA was used as template for the amplification. PCR conditions were: 30 cycles, 94° C. for 40" 58° C. for 40" 68° C. for 40". PCR fragment were purified by the Qiagen QIAquick PCR Purification Kit, and submitted to sequence analysis, which was performed using an ABI 377 Automatic Sequencer. Sequencing was performed using primers A1, B2, 22 (SEQ ID 57) and 32 (SEQ ID 58).

The gene was detected by PCR in all 70 *Neisseria* strains. In *N. lactamica* a band could be detected by Western blotting, but the gene could not be amplified.

Figure 9:
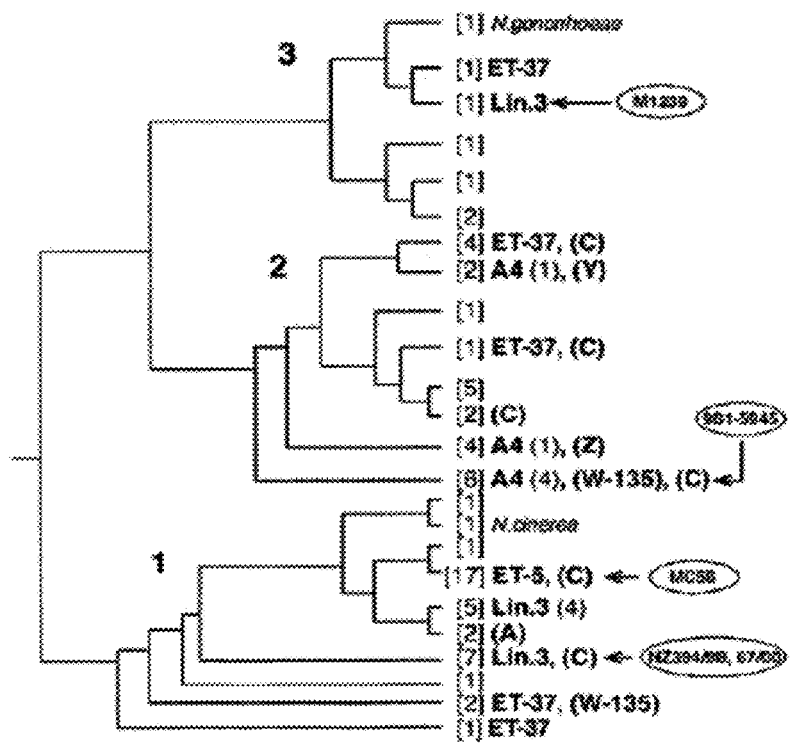
FIG. 9 is a dendrogram showing the strain clustering according to NMB1870 protein distances. The labels '1', '2' and '3' indicate the three variants. Numbers in square brackets indicate the number of strains with identical sequence present in each branch of the dendrogram. Hypervirulent lineages are indicated, followed by the number of strains when this is different from the total number. Serogroups other than B are also shown. The three type strains (MC58, 961-5965 and M1239) and the other strains used in the serological analysis are within circles.

The nucleotide sequence of the gene was determined in all 70 strains. A total of 23 different protein sequences were encoded (SEQ ID NO$^S$ 1 to 23). Computer analysis of these 23 sequences, using Kimura and Jukes-Cantor algorithm, divided them into three variants (FIG. 9). The dendrogram was obtained starting from the multiple sequence alignment of NMB1870 protein sequences (PileUP) using the Protein Sequence Parsimony Method (ProtPars), a program available within the Phylogeny Inference Package (Phylip), and confirmed by the GCG program Distances, using the Kimura and Jukes-Cantor algorithms.

The NMB1870 sequences from 100 further strains were determined. Many of these were identical to one of SEQ ID NO$^S$ 1 to 23, but 19 further unique sequences are given as SEQ ID NO$^S$ 140 to 158.

Figure 12:
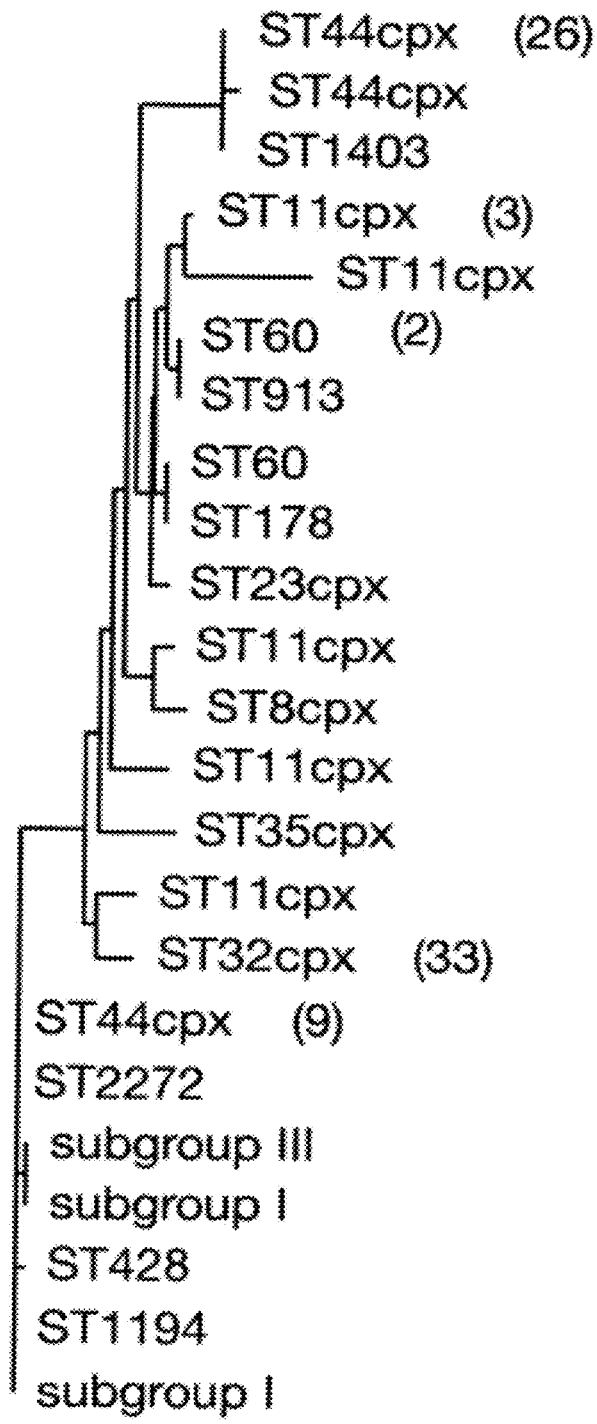
FIGS. 12 (variant 1), 13 (variant 2) and 14 (variant 3) show dendrograms for the three separate variants of NMB1870, classified by multilocus sequence types (ST).
Figure 13:
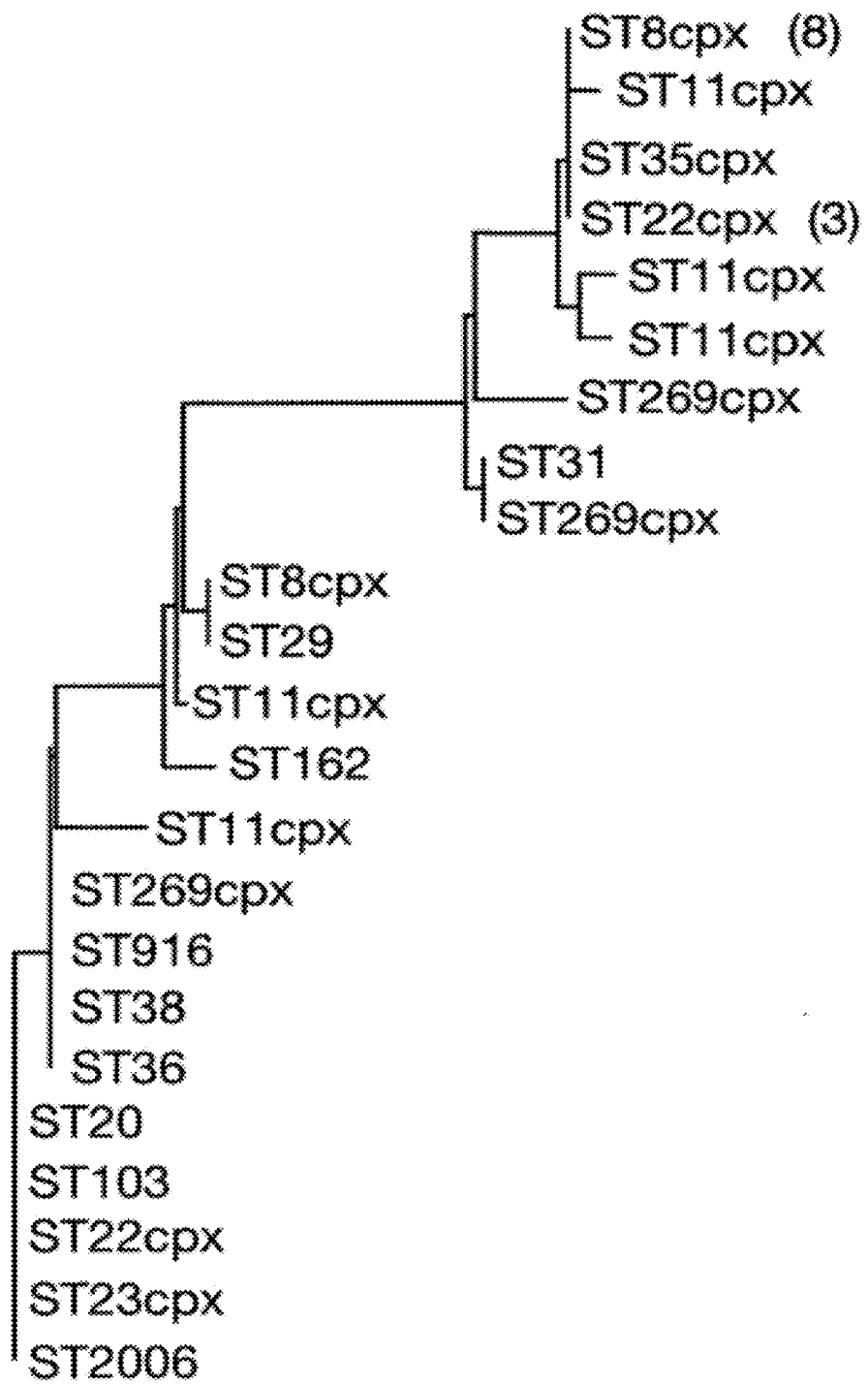
Figure 14:
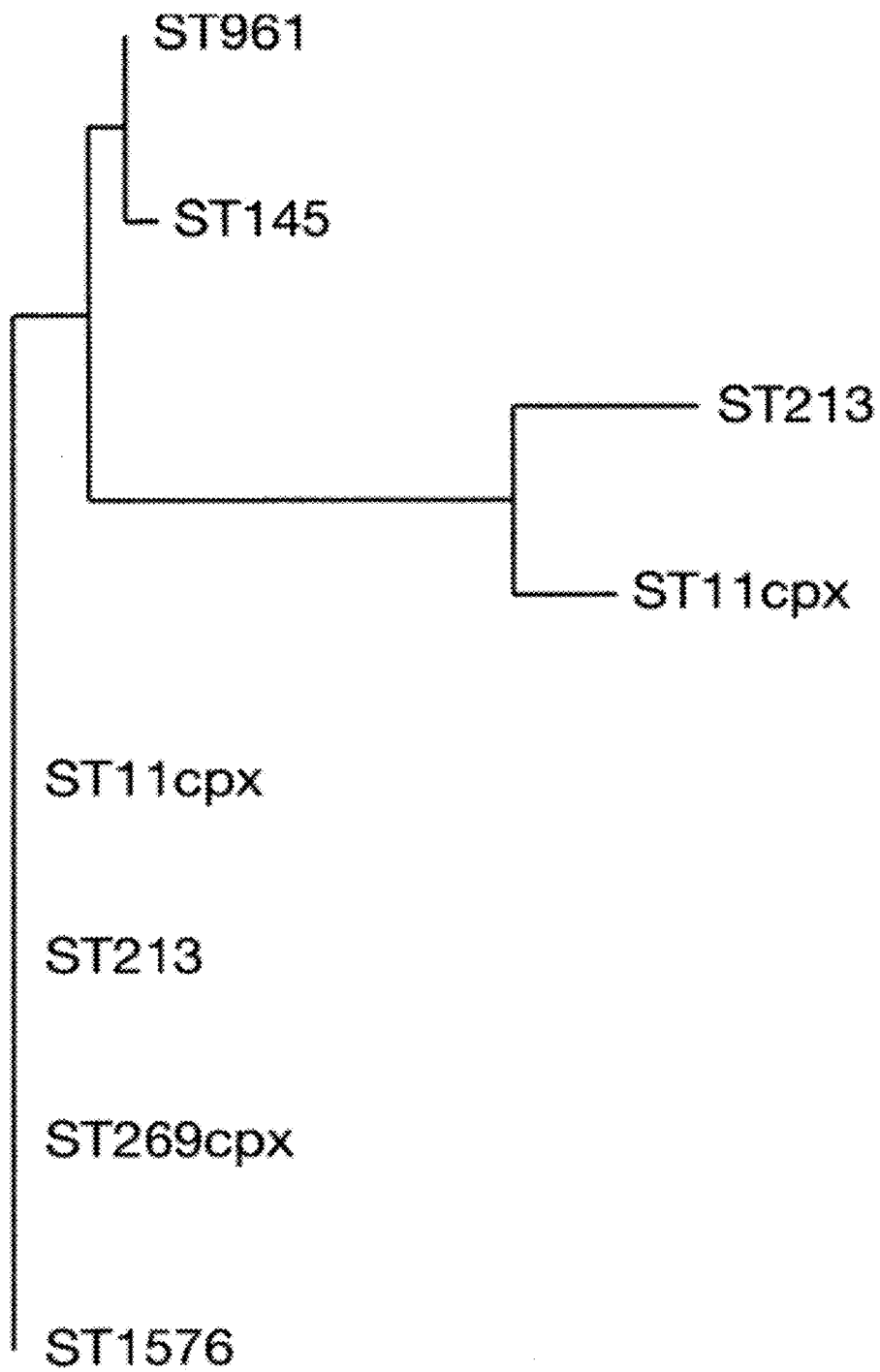

FIGS. 12-14 show dendrograms of the various sequences, classified by ST multilocus sequence types. Within variant 1 (FIG. 12) the reference strain is MC58, with the lowest sequence identity to the reference being 89.4% against an average of 93.7%. Within variant 2 (FIG. 13) the reference strain is 2996 and sequences extend down to 93.4% identity (average 96.3%). Within variant 3 (FIG. 14) the lowest identity to reference strain M1239 is 94.7% (average 95.8%). ST32 cpx is the most homogeneous hypervirulent cluster, harbouring only one NMB8170 sequence from variant I (also also only one form of NMB1343 and of NadA). Most ST44 cpx strains harbour variant 1 (several different sequences) of NMB1870, with some having variant 3 (single sequence). These data suggest that ST32 cpx is closer to ST44 cpx, as compared to other clusters, which matches data based on porA genotype (class III). ST11 and ST8 complexes are mostly represented by different sequences within variant 2 of NMB1870, suggesting that these complexes are closer together, as compared to other clusters, and matching the porA genotype (class II). ST11cpx harbours all three variants, indicating that it is the most diverse hypervirulent cluster out of the four.

Strains MC58, 961-5945 and M1239 were arbitrarily selected as type strains for variants 1, 2 and 3, respectively. The sequence diversity between the three type strains is shown in FIG. 10. Amino acid identity was 74.1% between variant 1 and variant 2, 62.8% between variant 1 and variant 3, and 84.7% between variant 2 and variant 3. Sequences within each variant were well-conserved, the most distant showing 91.6%, 93.4% and 93.2% identity to their type strains, respectively. *N. cinerea* belongs to variant 1, and shares 96.7% homology with MC58. As shown in FIG. 9, variant 1 harbours all strains from hypervirulent lineages ET-5, most lineage 3 strains, the serogroup A strains, two recent isolates of W-135 and one ET-37. Variant 2 harbours all strains from the hypervirulent complex A4, from serogroups Y and Z, one old W-135 isolate and five ET-37 strains. Variant 3 harbours four unique ST strains, one ET-37 strain, one lineage 3 strain and gonococcus.

The strains in each variant group, and their NMB1870 sequences, are as follows:

| | |
|---|---|
| 1 | gb185 (sequence shared with ES14784, M.00.0243291) |
| | m4030 (sequence shared with M3812) |
| | m2197 |
| | m2937 |
| | iss1001 (sequence shared with NZ394/98, 67/00, 93/114, bz198, m1390, nge28, 14996, 65/96, ISS1120, S59058, ISS1017, ISS1043, ISS1026, ISS1102, ISS1106, ISS656, ISS678, ISS740, ISS749, ISS995, ISS845, ISS1167, ISS1157, ISS1182, M4717, M6094, D8273) |
| | lnp17592 (sequence shared with 00-241341, 00-241357, 2ND80. 2ND221, ISS1142) |
| | f6124 (sequence shared with 205900) |
| | m198/172 (sequence shared with bz133, gb149, nm008, nm092, ES14963, FN131218, S5902, S90307, M4105, ISS1180, FN131345) |
| | mc58 (sequence shared with 30/00, 39/99, 72/00, 95330, bz169, bz83, cu385, h44/76, m1590, m2934, m2969, m3370, m4215, m4318, n44/89, 14847, ES14898, lnp15709, lnp17391, lnp17503, FN131654, M3985, S590104, S9029, S9097, D8346, FN131682, ISS832, ISS648, ISS1067, ISS1071, ISS1159) |
| | FN131217 |
| | ES14933 |
| | GB0993 |
| | M6190 |
| | F19324 |
| | ISS1113 |
| | gb0345 (sequence shared with M1820, ISS1082) |
| | M0445 |
| | 17 sequences, 98 strains |
| 2 | L93/4286 |
| | m2671 |
| | 961-6945 (sequence shared with 2996, 96217, 312294, 11327, a22, ISS1141, ISS1173, ISS759, ISS743, ISS866, F17094, NMB, SWZ107) |
| | gb013 (sequence shared with e32, m1090, m4287, 66094, M3153, M4407, NGH36) |
| | 860800 (sequence shared with 599) |
| | 95N477 (sequence shared with 90-18311, c11, m986, F370/85, M.00.0243143, ISS838, ISS839, ISS1092, M1569) |
| | 1000 (sequence shared with m1096, M2552, M4458, M5149, M6208) |
| | m3279 (sequence shared with bz232, dk353, m3697, ngh38, M5258, D8221) |
| | MK82 |
| | 8047 |
| | C4678 |
| | ISS1133 |
| | NG6/88 |
| | M0579 |
| | F16325 |
| | 15 sequences, 56 strains |
| 3 | 16889 |
| | m3813 |
| | m1239 |
| | ngp165 |
| | gb355 (sequence shared with m3369, D8300, gb0364, M2441) |
| | gb988 |
| | [fa1090 gonococcus] |
| | 7 sequences, 11 strains |

NB: the abbreviation "gb" at the beginning of a strain name means "M.01.0240".

SEQ ID NO$^S$ 139 (strain 2201731), 140 (strains gb101 & ISS908) and 141 (strain nge31) are distant from these three variants (as is, to a lesser degree, strain m3813).

Within variant 1, the strain lnp17592 sequence (also seen in strains 00-241341, 00-241357, 2ND80. 2ND221 & ISS1142)

is seen in the W-135 Haji serogroup. Within the Haji strains, the NadA sequence (SEQ ID NO: 143) is a recombination between alleles 2 and 3 [191, 192].

Cloning, Expression & Purification in *E. coli*

NMB1870 genes were amplified by PCR from the genome of *N. meningitidis* MC58, 961-5945 and M1239 strains. Forward and reverse primers were designed in order to amplify the nmb1870 coding sequence devoid of the sequence coding for the putative leader peptide. M1239 and 961-5945 variants were found not to be expressible in *E. coli*. They were therefore expressed by adding to the N-terminal the sequence SEQ ID NO: 46 that is present in the gonococcus protein but absent in the meningococcus counterpart. Oligonucleotides used for the amplification were as follows:

| Strain | Forward | Reverse |
| --- | --- | --- |
| MC58 | CGCGGATCCCATATGGTCGCCGCCGACATCG ('For1'; SEQ ID 47) | CCCGCTCGAGTTGCTTGGCGGCAAGGC ('Rev1'; SEQ ID 48) |
| 961/5945 | CGCGGATCCCATATGGGCCCTGATTCTGACCGCCTGCAGCAGC GGAGGGTCGCCGCCGACATCGG ('For2'; SEQ ID 49) | CCCGCTCGAGCTGTTTGCCGGCGATGCC ('Rev2'; SEQ ID 50) |
| M1239 | CGCGGATCCCATATGGGCCCTGATTCTGACCGCC TGCAGCAGCGGAGGGGAGGGGGTGGTGTCGC ('For3'; SEQ ID 51) | GCCCAAGCTTCTGTTTGCCGGCGATGCC ('Rev3'; SEQ ID 52) |

Restriction sites, corresponding to NdeI for the forward primers and XhoI (HindIII for M1239) for the reverse primers, are underlined. For the 961-5945 and M1239 forward primers, the gonococcus sequence moiety is reported in italics, and the meningococcal NMB1870 matching sequences are reported in bold.

PCR conditions in the case of primer combination For1/Rev1 were: denaturation at 94° C. for 30", annealing at 57° C. for 30", elongation at 68° C. for 1 min (5 cycles), denaturation at 94° C. for 30", annealing at 68° C. for 30", elongation at 68° C. for 1 min (30 cycles). In the case of primer combinations: For2/Rev2 and For3/Rev2 and For3/Rev3: 94° C. for 30", 56° C. for 30", 68° C. for 1 min (5 cycles), 94° C. for 30", 71° C. for 30", 68° C. for 1 min (30 cycles).

Full-length nmb1870 gene was amplified from the MC58 genome using the following primers: f-1For (CGCGGATCC CATATGAATCGAACTGCCTTCTGCTGCC; SEQ ID 53) and f-1Rev (CCCG CTCGAGTTATTGCTTGGCGGCAAGGC; SEQ ID 54) and the following conditions: 94° C. for 30", 58° C. for 30", 72° C. for 1 min (30 cycles).

PCR were performed on approx. 10 ng of chromosomal DNA using High Fidelity Taq DNA Polymerase (Invitrogen). The PCR products were digested with NdeI and XhoI and cloned into the NdeI/XhoI sites of the pET-21b+ expression vector (Novagen).

Recombinant proteins were expressed as His-tag fusions in *E. coli* and purified by MCAC (Metal Chelating Affinity Chromatography), as previously described [3], and used to immunise mice to obtain antisera. *E. coli* DH5α was used for cloning work, and BL21(DE$_3$) was used for expression.

nmb1870 and siaD Isogenic Mutants

Isogenic knockout mutants in which the nmb1870 gene was truncated and replaced with an erythromycin antibiotic cassette, was prepared by transforming strains MC58, 961-5945 and M1239 with the plasmid pBSΔnmb1870ERM. This plasmid contains the erythromycin resistance gene within the nmb1870 upstream and downstream flanking regions of 500 bp. These regions were amplified from MC58 genome using the following oligonucleotides Ufor GC TCTAGACCAGCCAGGCGCATAC (SEQ ID 59, XbaI site underlined); URev TCC CCCGGGGACGGCATTTTGTTTACAGG (SEQ ID 60, SmaI underlined); DFor TCC CCCGGGCGCCAAGCAATAACCATTG (SEQ ID 61, SmaI underlined) and Drev CCCG CTCGAGCAGCGTATCGAACCATGC (SEQ ID 62, XhoI underlined). A capsule deficient mutant was generated using the same approach. The siaD gene was deleted and replaced with ermC using the plasmid pBSΔCapERM. The upstream and downstream flanking regions of 1000 bp and 1056 bp, respectively, were amplified from MC58 genome using the following primers: UCapFor GC TCTAGATTCTTTCCCAAGAACTCTC (SEQ ID 63, XbaI underlined); UcapRev TCC CCCGGGCCCGTATCATCCACCAC (SEQ ID 64, SmaI underlined); DCapFor TCC CCCGGGATCCACGCAAATACCCC (SEQ ID 65, SmaI underlined) and DCapRev CCCG CTCGAGATATAAGTGGAAGACGGA (SEQ ID 66, XhoI underlined). Amplified fragments were cloned into pBluescript and transformed into naturally competent *N. meningitidis* strain MC58. The mixture was spotted onto a GC agar plate, incubated for 6 hrs at 37° C., 5% CO$_2$ then diluted in PBS and spread on GC agar plates containing 5 µg/ml erythromycin. The deletion of the nmb1870 gene in the MC58Δnmb1870, 961-5945Δnmb1870 and M1239Δnmb1870 strains was confirmed by PCR; lack of NMB1870 expression was confirmed by Western blot analysis. The deletion of the siaD gene and the lack of capsule expression in the MC58ΔsiaD strain were confirmed by PCR and FACS, respectively.

Lipoproteins

To investigate lipidation of NMB1870, palmitate incorporation of recombinant *E. coli* BL21(DE$_3$) strain carrying the full-length nmb1870 gene was tested as described in reference 193.

Meningococcal strains MC58 and MC58Δnmb1870 were grown in GC medium and labeled with [9,10-$^3$H]-palmitic acid (Amersham). Cells from 5 ml culture were lysed by boiling for 10 min and centrifuged at 13,000 rpm. The supernatants were precipitated with TCA and washed twice with cold acetone. Proteins were suspended in 50 µl of 1.0% SDS and 15 µl analyzed by SDS-PAGE, stained with Coomassie brilliant blue, fixed and soaked for 15 min in Amplify solution (Amersham). Gels were exposed to Hyperfilm MP (Amersham) at −80° C. for three days.

A radioactive band of the appropriate molecular weight was detected in MC58, but not in the Δnmb1870 knockout mutant.

Recombinant *E. coli* grown in the presence of [9,10-$^3$H]-palmitic acid also produce a radioactive band at the expected molecular weight, confirming that *E. coli* recognises the lipoprotein motif and adds a lipid tail to the recombinant protein.

Protein Detection

MC58 strain was grown at 37° C. with 5% $CO_2$ in GC medium at stationary phase. Samples were collected during growth ($OD_{620nm}$ 0.05-0.9). MC58Δnmb1870 was grown until $OD_{620nm}$ 0.5. Bacterial cells were collected by centrifugation, washed once with PBS, resuspended in various volumes of PBS in order to standardise the OD values. Culture supernatant was filtered using a 0.2 μm filter and 1 ml precipitated by the addition of 250 μl of 50% trichloroacetic acid (TCA). The sample was incubated on ice for 2 hr, centrifuged for 40 min at 4° C. and the pellet washed with 70% ice cold ethanol, and resuspended in PBS. 3 μl of each sample (corresponding to an $OD_{620}$ 0.03) was then loaded on a 12% polyacrylamide gels and electrotransferred onto nitrocellulose membranes.

Western blot analysis were performed according to standard procedures, using polyclonal antibodies raised against protein expressed in *E. coli*, at a 1:1000 dilution, followed by a 1/2000 dilution of HPR-labeled anti-human IgG (Sigma). Scanning was performed using a LabScan (Pharmacia) and Imagemaster software (Pharmacia).

Figure 3:
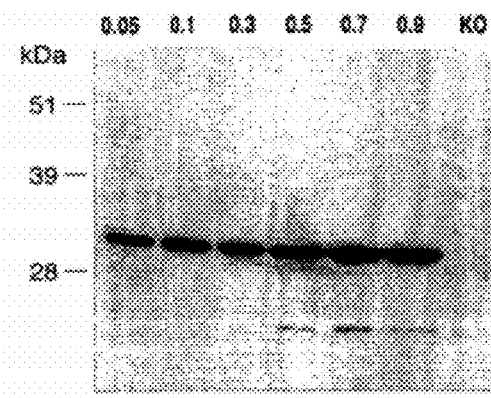
FIG. 3 shows the increase in NMB1870 levels in *N. meningitidis* MC58 during the growth curve.
Figure 4:
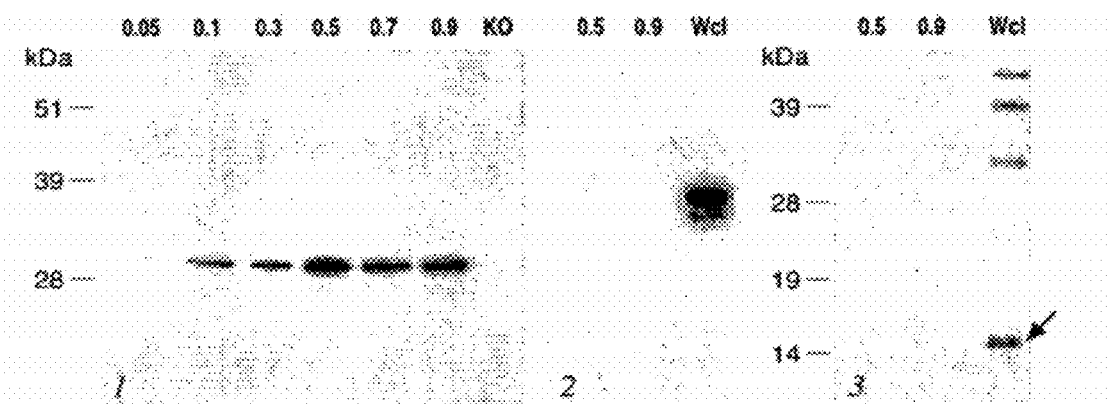
FIG. 4 shows the increase in NMB1870 levels in the supernatant over the same period. PorA levels and NMB1380 levels do not increase. Numbers above lanes refer to $OD_{620nm}$ of the culture. KO indicates a NMB1870 knockout mutant of MC58, and Wcl stands for the whole cell lysate control.

As shown in FIG. 3, a protein of ~29.5 kDa was detected in the total cell extracts of *N. meningitidis*. The amount of the protein in the whole cell lysate approximately doubled during the growth curve, while the optical density of the culture increased from 0.05 to 0.9 $OD_{620nm}$. A band of the same size was also detected in the culture supernatant. The protein was not detected in the supernatant of the freshly inoculated culture ($OD_{620nm}$ 0.05), and increased approximately four times during the growth from 0.1 to 0.9 $OD_{620nm}$ (FIG. 4, left-hand panel). The genuine nature of the expression in the supernatant was confirmed by testing the same samples for membrane blebs and cytoplasmic proteins. As shown in the middle panel of FIG. 4, the absence of PorA in the supernatant preparations of PorA rules out a possible contamination with membrane blebs, while the absence in the supernatant of cytoplasmic protein NMB1380 confirmed that the supernatant samples do not result from cell lysis (right-hand panel).

The MC58Δnmb1870 knockout strain shows no protein in either whole cell lysate or culture supernatant (lanes 'KO' in FIGS. 3 & 4).

Figure 5:
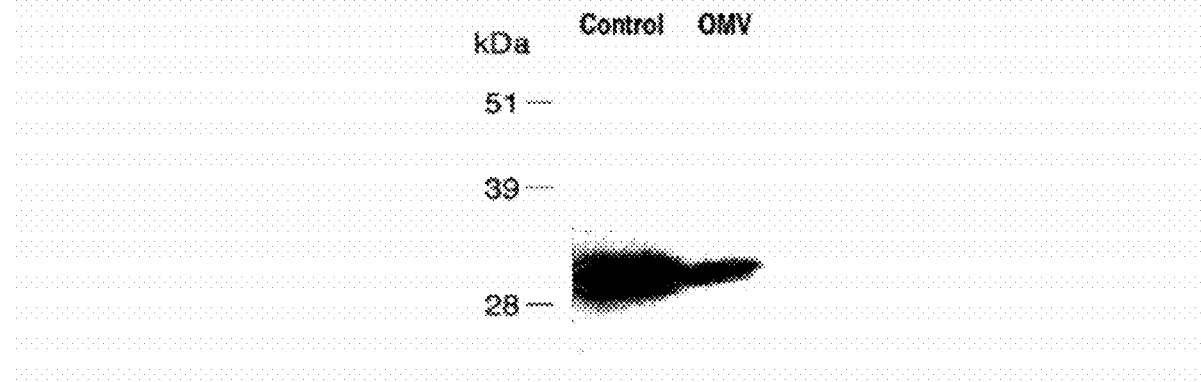
FIG. 5 shows OMVs probed with anti-NMB1870.

NMB1870 was detected by western blotting in outer membrane vesicles, confirming that the protein segregates with the membrane fractions of *N. meningitidis* (FIG. 5). However, sera from mice immunised with the OMVs did not recognise recombinant NMB1870 in western blotting, suggesting that the protein is not immunogenic in OMV preparations.

Figure 6:
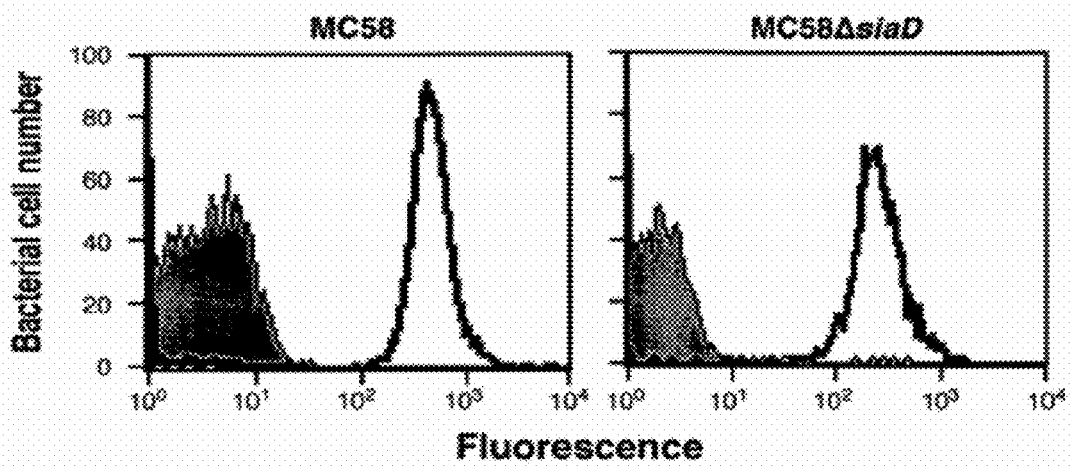
FIG. 6 shows FACS analysis of encapsulated MC58 or a non-encapsulated mutant MC58 using anti-NMB1870.

FACS analysis using the anti-NMB1870 antibodies confirmed that the protein is surface-exposed and accessible to antibodies both in encapsulated and non-encapsulated *N. meningitidis* strains (FIG. 6). FACS analysis used a FACSScan flow cytometer, with antibody binding detected using a secondary antibody anti-mouse (whole molecule) FITC-conjugated (Sigma). The positive FACS control used SEAM3, a mAb specific for the meningococcus B capsular polysaccharide [194]; the negative control consisted of a mouse polyclonal antiserum against the cytoplasmic protein NMB1380 [195].

Figure 7:
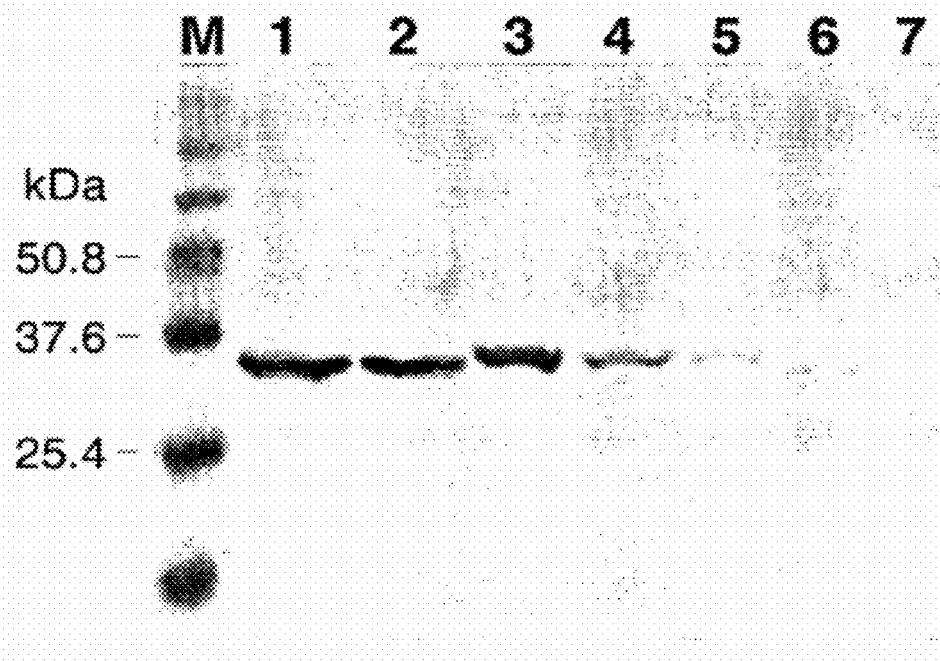
FIG. 7 is a western blot of a gradient SDS-PAGE gel loaded with total cell lysates of high (lanes 1 & 2), intermediate (3 & 4) and low (5 & 6) NMB1870 expressers. Lane 7 contains a MC58 NMB1870 knockout. Lanes are: (1) MC58; (2) H44/76; (3) NZ394/98; (4) 961-5945; (5) 67/00; (6) M1239; (7) MC58Δnmb1870.

Western blotting analysis of 43 strains showed that NMB1870 is expressed by all strains tested. As shown in FIG. 7, however, the levels of expression varied considerably from strain to strain. The strains tested could be broadly classified as high, intermediate and low expressers:

| Strains | High | Intermediate | Low |
|---|---|---|---|
| ET5 | 9/9 | 0/9 | 0/9 |
| Lineage 3 | 7/9 | 1/9 | 1/9 |
| ET37 | 2/3 | 1/3 | 0/3 |
| A4 | 0/4 | 2/4 | 2/4 |
| Other | 6/15 | 7/15 | 2/15 |
| *N. gonorrhoeae* | 0/1 | 0/1 | 1/1 |
| *N. cinerea* | 0/1 | 0/1 | 1/1 |
| *N. lactamica* | 1/1 | 0/1 | 0/1 |
| Total | 25/43 (58%) | 11/43 (25.5%) | 7/43 (16.5%) |

Most of the strains from hypervirulent lineages (ET-5, lineage 3, ET-37) expressed high levels of the protein, with the exception of A4 where two strains expressed intermediate levels and two expressed low levels. Interestingly, the protein was expressed at high level by strains that have been classically used as OMV vaccine strains. No obvious genetic patterns were found to predict the amount of protein expressed by each strain. Even the presence of the IS element in the promoter region, which was found in 8/70 strains (one from serogroup A, three from lineage 3, and four from those classified as others), did not show any correlation with the expression of the protein.

Scanning of the Western blots showed that the difference in expression between high and intermediate, intermediate and low or high and low could be two-, five- and nine-fold, respectively. There is no immediately-apparent reason for the different expression levels, and analysis of the DNA sequences upstream from the gene did not show any feature that correlates with expression.

Antibody Responses

Sera from healthy and convalescent subjects were analysed for anti-NMB1870 antibodies by Western blot. Purified NMB1870 (1 μg/lane) was loaded onto 12.5% SDS-polyacrylamide gels and transferred to a nitrocellulose membrane. The bound protein was detected with 1/200 dilution of sera, followed by a 1/2000 dilution of HPR-labeled anti-human IgG (Sigma). While only 2/10 of sera from healthy people recognised NMB1870, 21/40 convalescent sera recognised the protein, leading to the conclusion that NMB1870 is immunogenic in vivo during infection. Antisera from mice immunised with recombinant NMB1870 were therefore investigated further.

To prepare antisera, 20 μg of variant 1, variant 2 and variant 3 NMB1870 recombinant proteins were used to immunise six-week-old CD1 female mice (Charles River). Four to six mice per group were used. The recombinant proteins were given i.p., together with complete Freund's adjuvant (CFA) for the first dose and incomplete Freund's adjuvant (IFA) for the second (day 21) and third (day 35) booster doses. The same immunization schedule were performed using aluminium hydroxide adjuvant (3 mg/ml) instead of Freund's adjuvant. Blood samples for analysis were taken on day 49.

The antisera were tested for their ability to induce complement-mediated killing of capsulated *N. meningitidis* strains, as previously described [3, 196] using pooled baby rabbit serum (CedarLane) used as complement source. Serum from a healthy human adult (with no intrinsic bactericidal activity when tested at a final concentration of 25 or 50%) was also used as complement source. Serum bactericidal titers were defined as the serum dilution resulting in 50% decrease in colony forming units (CFU) per ml after 60 mins. incubation of bacteria with reaction mixture, compared to control CFU per ml at time 0. Typically, bacteria incubated with the negative control antibody in the presence of complement showed a 150 to 200% increase in CFU/ml during the 60 min incubation.

Figure 8:
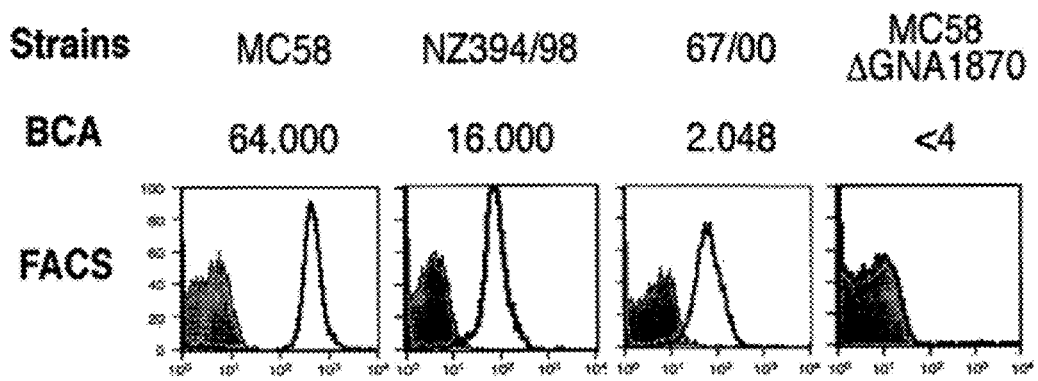
FIG. 8 shows FACS and bactericidal titres for each of a high, intermediate and low expresser, and also for the NMB1870 knockout. The intermediate and low expresser have identical NMB1870 amino acid sequences, with a 91.6% match to MC58.

Representative strains from the high, intermediate and low expressors were selected for the assay. The differential expression of the protein on the surface of the selected strains was confirmed by FACS analysis (FIG. 8)—MC58, a representative of the high expresser strains was killed with high efficiency by the serum diluted up to 1/64,000; NZ394/98 (originally NZ98/254), a representative of the intermediate expressers was also killed with high efficiency, by the serum diluted up to 1/16,000 and even strain 67/00, a representative of the low expresser strains was killed by the antiserum diluted up to 1/2,048. Control strains, where the nmb1870 gene had been knocked out, was not killed by the same antiserum.

To confirm whether the sera were also able to confer protection in vivo, they were tested for ability to induce passive protection in the infant rat model. Five-day-old infant rats were pre-treated i.p. with anti-NMB1870 antisera or with anti-PorA monoclonal antibody at time 0 and challenged two hours later i.p. with $5 \times 10^3$ CFU/rat of MenC 4243 (OAc-positive) or MenB NZ394/98. Quantitative blood cultures were obtained 24 hours later. Bacterial counts in the blood cultures (CFU/ml, geometric means) were obtained by plating blood on chocolate agar plates. Positive control serum was anti-PorA(P1.2) for MenC and SEAM3 for MenB. Results of the experiments were as follows:

| Pre-treatment | Challenge Strain 4243 | | Challenge Strain NZ394/98 | |
|---|---|---|---|---|
| | Positives | CFU/ml × $10^3$ | Positives | CFU/ml × $10^3$ |
| PBS | 5/5 | 450 | — | — |
| Negative control serum | 5/5 | 500 | 9/14 | 1260 |
| Positive control serum | 1/5 | 0.003 | 0/7 | <0.001 |
| Anti-NMB1870 | 0/9 | <0.001 | 0/14 | <0.001 |

Therefore no bacterial colonies were recovered from the blood of the rats passively immunised with anti-NMB1870 serum, while most of the negative control animals were bacteremic.

Bactericidal Activity is Variant-Specific

Each type variant was expressed in *E. coli* as a His-tagged protein and used to immunise mice. The sera were used to test the immunological cross-reactivity between strains of the three variants by FACS and bactericidal assay. As shown in FIG. 11, by FACS analysis, all strains were recognised by each serum, although the degree of recognition varied considerably, usually reflecting the amino acid homology between the proteins.

On closer analysis, the anti-variant-1 serum (FIG. 11, first row) recognised MC58 strain very well (as expected), to a lower extent the 961-5945 strain (74.1% identity) and, to a lesser extent, the M1239 strain (62.8% identity). A similar trend was found for antisera against variants 2 and 3 (rows 2 and 3 of FIG. 11), although with the anti-variant-2 serum the differences were not as striking.

A monoclonal antibody against the capsule recognised all three strains equally well the (row 4), while a serum against the cytoplasmic protein NMB1380 used as negative control did not recognise any (row 5). Similarly, the nmb1870 knockout mutants were not recognised by any sera (row 6).

The differences in immunorecognition between the variants were more evident by bactericidal assay:

| Sera | MC58 (variant 1) | 961/5945 (variant 2) | M1239 (variant 3) |
|---|---|---|---|
| Anti-variant 1 | 64000 | 256 | <4 |
| Anti-variant 2 | <4 | 16000 | 128 |
| Anti-variant 3 | <4 | 2048 | 16000 |

The data show that the serum against each variant was able to induce an efficient complement-mediated killing of the homologous strain (titers ranging between 16,000 and 64,000), while the activity was low (128-2,048) or absent (<4) against strains of the other variants. As predicted from the close amino acid homology, the cross-bactericidal titers between variants 2 and 3 were higher than the others. When human complement was used, bactericidal titers of 4,096, 256 and 512 were obtained with variants 1, 2 and 3, respectively, using the homologous type strains. No titers were detected against the heterologous strains.

Hybrid and Tandem Proteins

Hybrid and tandem proteins can be represented by the formula: $NH_2$-A-[-X-L-]$_n$-B-COOH. Genes encoding various proteins of this type were constructed, where n=2, the N-termini of $X_1$ and $X_2$ are deleted up to the end of their poly-glycine regions, and -$L_2$- and -B- are absent (or else B is a poly-histidine tag used for purification). The following table shows the components of these proteins in their mature forms, and gives the SEQ ID NO$^S$ of the full polypeptide and the SEQ ID NO$^S$ and strains for the component sequences A, $X_1$, $L_1$ and $X_2$:

| | SEQ ID | A | $X_1$ | $L_1$ | $X_2$ | pI |
|---|---|---|---|---|---|---|
| (1) | 79 | — | MC58 (SEQ ID 80) | SEQ ID 78 | 2996 (SEQ ID 81) | 6.74 |
| (2) | 82 | — | MC58 (SEQ ID 80) | SEQ ID 144 | 2996 (SEQ ID 81) | 6.63 |
| (3) | 83 | — | MC58 (SEQ ID 80) | SEQ ID 78 | M1239 (SEQ ID 84) | |
| (4) | 85 | — | MC58 (SEQ ID 80) | SEQ ID 144 | M1239 (SEQ ID 84) | |
| (5) | 87 | SEQ ID 86 | 2996 (SEQ ID 81) | SEQ ID 78 | M1239 (SEQ ID 84) | 6.44 |
| (6) | 88 | SEQ ID 86 | 2996 (SEQ ID 81) | SEQ ID 144 | M1239 (SEQ ID 84) | 6.35 |
| (7) | 89 | SEQ ID 86 | M1239 (SEQ ID 84) | SEQ ID 78 | 2996 (SEQ ID 81) | |
| (8) | 90 | SEQ ID 86 | M1239 (SEQ ID 84) | SEQ ID 144 | 2996 (SEQ ID 81) | |
| (9) | 91 | Cys | '936' (SEQ ID 76) | SEQ ID 78 | 2996 (SEQ ID 81) | |
| (10) | 92 | Cys | '936' (SEQ ID 76) | SEQ ID 144 | 2996 (SEQ ID 81) | |
| (11) | 93 | Cys | '936' (SEQ ID 76) | SEQ ID 78 | M1239 (SEQ ID 84) | |
| (12) | 94 | Cys | '936' (SEQ ID 76) | SEQ ID 144 | M1239 (SEQ ID 84) | |

Of these twelve proteins, therefore, eight are tandem NMB1870 proteins (MW~55 kDa) and four are hybrid proteins with '936$_{2996}$' at the N-terminus (MW~49 kDa). Two linkers were used: (a) SEQ ID NO: 78, which is derived from the gonococcal NMB1870 homolog (SEQ ID NO: 46); and (b) a glycine-rich linker (SEQ ID NO: 144). SEQ ID NO: 78 was also used at the N-terminus of mature proteins, without its two N-terminus BamHI residues (Gly-Ser) i.e. SEQ ID NO: 86.

All twelve proteins were soluble when expressed in *E. coli* and, after purification, were used to immunise mice. Serum bactericidal antibody (SBA) responses were assessed against up to four meningococcal strains, ensuring one from each of the three NMB1870 variants 1 to 3 (shown as superscripts). The adjuvant was either CFA (top) or an aluminium hydroxide (bottom):

| Protein | SBA | | | |
|---|---|---|---|---|
| | 2996[2] | MC58[1] | M1239[3] | 961/5945[2] |
| (1) | 4096 | 262144 | 2048 | 32768 |
| | 1024 | 32768 | 128 | 2048 |
| (2) | 8192 | 262144 | 2048 | 32768 |
| | 1024 | 16384 | 512 | 1024 |
| (3) | — | 131072 | 32768 | 4096 |
| | — | 32768 | 4096 | 1024 |
| (4) | — | 262144 | 32768 | 8192 |
| | — | 32768 | 1024 | 512 |
| (5) | 512 | <4 | 4096 | 32768 |
| | 1024 | 16 | 4096 | 8192 |
| (6) | 4096 | <4 | 32768 | 32768 |
| | 2048 | 16 | 4096 | 16384 |
| (7) | — | 4 | 4096 | 32768 |
| | — | 16 | 4096 | 8192 |
| (8) | 2048 | 32 | 32768 | 32768 |
| | 1024 | 32 | 8192 | 16384 |
| (9) | 2048 | <4 | <4 | 32768 |
| | 4096 | <4 | 512 | 16384 |
| (10) | 4096 | <4 | 256 | 131072 |
| | 512 | <4 | <4 | 2048 |
| (11) | 256 | <4 | >32768 | 2048 |
| | 4 | 4 | 4096 | 128 |
| (12) | 2048 | <4 | >32768 | 4096 |
| | 16 | 256 | 4096 | 256 |

These results clearly show the variant-specific nature of the immune reactions. For example, proteins (1) and (2) include sequences from NMB1870 variants 1 and 2, and the best SBA results are seen against these two variants. Similarly, the best results are seen against variants 1 and 3 when using proteins (3) and (4). Good activity is seen using NMB1870 from variants 2 and 3, in either order from N-terminus to C-terminus, using proteins (5) to (8), with little activity against variant 1. The variant-specific nature of the NMB1870 response is also apparent when using the hybrid proteins, with some anti-2996 activity being provided by the '936' moiety.

The following oligonucleotide primers were using during the construction of the 12 proteins:

| Protein | Primer SEQ ID NO$^S$ (Fwd & Rev) | Restriction sites |
|---|---|---|
| (1) | 95 & 96 | BamHI & XhoI |
| (2) | 97 & 98 | BamHI & XhoI |
| (3) | 99 & 100 | BamHI & HindIII |
| (4) | 101 & 102 | BamHI & HindIII |
| (5) | 103 & 104 | BamHI & HindIII |
| (6) | 105 & 106 | BamHI & HindIII |
| (7) | 107 & 108 | BamHI & XhoI |
| (8) | 109 & 110 | BamHI & XhoI |
| (9) | 111 & 112 | BamHI & XhoI |
| (10) | 113 & 114 | BamHI & XhoI |
| (11) | 115 & 116 | BamHI & HindIII |
| (12) | 117 & 118 | BamHI & HindIII |
| NMB1870$_{M1239}$ | 119 & 120 | NdeI & BamHI |
| NMB1870$_{2996}$ | 121 & 122 | NdeI & BamHI |

Triple Tandem Protein

A "triple tandem" protein, where n=3, was constructed based on strains (1) MC58, (2) 2996 and (3) m1239. The 757mer triple tandem protein NH$_2$-A-X$_1$-L$_1$-X$_2$-L$_2$-X$_3$-L$_3$-B-COOH has amino acid sequence SEQ ID NO: 142:

| Moiety | A | X$_1$ | L$_1$ | X$_2$ | L$_2$ | X$_3$ | L$_3$ | B |
|---|---|---|---|---|---|---|---|---|
| Detail | — | NMB1870$_{MC58}$ | Gly-rich linker | NMB1870$_{2996}$ | Gly-rich linker | NMB1870$_{m1239}$ | — | — |
| SEQ ID | — | 80 | 144 | 81 | 144 | 84 | — | — |
| Variant | — | 1 | — | 2 | — | 3 | — | — |

X$_2$ and X$_3$ both lack the N-terminus up to their poly-glycine regions (i.e. they are ΔG sequences).

Bactericidal SBA Titres

Mice were immunised with nine different proteins and the bactericidal activity of the resulting sera were tested against different strains of meningococcus, including both strains which match those from which the immunising proteins were derived and strains which are different from the immunising proteins. The nine proteins were:

(A), (B) & (C) Hybrid proteins of 936 and NMB1870
- (A) $NMB1870_{MC58}$=variant 1 [12]
- (B) $NMB1870_{2996}$=variant 2 e.g. SEQ ID NO$^S$: 91 & 92
- (C) $NMB1870_{M1239}$=variant 3 e.g. SEQ ID NO$^S$: 91 & 92

(D), (E) & (F) NMB1870 from single strains
- (D) $NMB1870_{MC58}$=variant 1 e.g. SEQ ID NO: 80
- (E) $NMB1870_{2996}$=variant 2 e.g. SEQ ID NO: 81
- (F) $NMB1870_{M1239}$=variant 3 e.g. SEQ ID NO: 84

(G), (H) & (I) NMB1870 tandem proteins
- (G) $NMB1870_{MC58}$-$NMB1870_{2996}$=variants 1 & 2 e.g. SEQ ID NO$^S$: 79 & 82
- (H) $NMB1870_{2996}$-$NMB1870_{M1239}$=variants 2 & 3 e.g. SEQ ID NO$^S$: 87 & 88
- (I) $NMB1870_{MC58}$-$NMB1870_{M1239}$=variants 1 & 3 e.g. SEQ ID NO$^S$: 83 & 85

Bactericidal responses were measured against up to 20 strains which possess variant 1 of NMB1870, against up to 22 strains with variant 2 of NMB1870 and against up to 5 strains with variant 3.

The bactericidal efficacy of sera raised against proteins (A) to (C) matched the genotype of the test strains e.g. using CFA as adjuvant for the immunisations, the SBA titres against strain MC58 (variant 1) were: (A) 262144; (B) <4; (C) <4. Similarly, when sera were tested against strain 961-5945 (variant 2) the SBA were: (A) 256; (B) 32768; (C) 4096. Finally, against strain M1239 (variant 3) titres were: (A) <4; (B) 512; (C) 32768.

Using CFA or aluminium hydroxide as adjuvant, protein (A) gave SBA titres of ≥512 against the following strains: M01-240185, M2197, LPN17592, M6190 (all ET37); MC58, BZ83, CU385, N44/89, 44/76, M2934, M4215 (all ET5); BZ133; M1390, ISS1026, ISS1106, ISS1102 (lin. 3); F6124 (sIII); and M2937 (other). These strains cover serogroups A, B, C and W135; no serogroup Y strains were tested.

Using CFA or aluminium hydroxide as adjuvant, protein (B) gave SBA titres ≥512 against strains: 2996, 961-5945, 96217 (cluster A4); M01-240013, C11, NGH38, M3279, M4287, BZ232 (other). These strains cover serogroups B and C; no serogroup A, W135 or Y strains were tested.

Using CFA or aluminium hydroxide as adjuvant, protein (C) gave SBA titres≥512 against strains: M01-0240364, NGP165 (ET37); M1239 (lin. 3); M01-240355, M3369 (other). These strains are in serogroup B, and no serogroup A, C, W135 or Y strains were tested.

The SBA patterns seen with proteins (A) to (C) were also seen with proteins (D) to (F). Against strain MC58, serum obtained using protein (D) and aluminium hydroxide adjuvant gave a SBA titre of 16384, whereas sera obtained using protein (E) or (F) and the same adjuvant gave SBA titres <4. Against strain 961-5945, protein (D) and (F) sera gave lower titres than those obtained using (E). Against, strain M1239, SBA titres were: (D) <4; (E) 128; (F) 16384.

With tandem proteins, SBA efficacy was broadened. Sera obtained using protein (G) were bactericidal against strain MC58 and 961-5945, as well as other strains which possess variant 1 or variant 2 of NMB1870. Sera raised against protein (H) gave low titres against strains which possess variant 1 of NMB1870, but high titres against other strains e.g. 16384 against strain 961-5945 (variant 2) and 32768 against strain M3369 (variant 3).

Sera obtained by immunisation with CFA-adjuvanted protein (H) gave SBA titres≥512 against: LNP17094, 96217, 961-5945, 2996, 5/99 (cluster A4); C4678, M01-0240364, NGP165 (ET37); M1239 (lin. 3); M2552, BZ232, M3279, M4287, 1000, NGH38, C11, M01-240013, M01-240355, M3369 (other). These strains cover serogroups B and C; activity against serogroups A, W135 or Y strains was not tested with protein (H).

Sera obtained by immunisation with CFA-adjuvanted protein (I) gave SBA titres≥512 against: M01-0240364, 14784, M6190, MC58, LPN17592, M2197 (ET37); 44/76 (ET5); M1239, ISS1102, ISS1106, ISS1026, 394/98 (lin. 3); M2937 (other). These strains cover serogroups B, C and W135; activity against serogroups A or Y strains was not tested with protein (I).

After immunisation with proteins containing variant 1 of NMB1870, sera tested against up to 20 strains which have a NMB1870 in variant 1 gave SBA titres as follows:

| | Protein | | | | | | | |
|---|---|---|---|---|---|---|---|---|
| | (A) | (A) | (D) | (D) | (G) | (G) | (I) | (I) |
| | Adjuvant | | | | | | | |
| | CFA | Alum | CFA | Alum | CFA | Alum | CFA | Alum |
| N° strains tested | 18 | 20 | 20 | 20 | 13 | 13 | 11 | 11 |
| SBA <128 | 1 | 7 | 4 | 3 | 0 | 5 | 0 | 2 |
| SBA 128-512 | 2 | 4 | 0 | 4 | 0 | 3 | 0 | 3 |
| SBA >512 | 15 | 9 | 16 | 13 | 13 | 5 | 11 | 6 |

After immunisation with proteins containing variant 2 of NMB1870, sera tested against up to 22 strains which have a NMB1870 in variant 2 gave SBA titres as follows:

| | Protein | | | | | | | | |
|---|---|---|---|---|---|---|---|---|---|
| | (B) | (B) | (E) | (G) | (G) | (H) | (H) | (I) | (I) |
| | Adjuvant | | | | | | | | |
| | CFA | Alum | Alum | CFA | Alum | CFA | Alum | CFA | Alum |
| N° strains tested | 16 | 19 | 22 | 16 | 15 | 22 | 22 | 7 | 6 |
| SBA <128 | 6 | 14 | 13 | 6 | 10 | 7 | 8 | 3 | 5 |
| SBA 128-512 | 0 | 2 | 7 | 3 | 3 | 1 | 6 | 0 | 1 |
| SBA >512 | 10 | 3 | 2 | 7 | 2 | 14 | 8 | 4 | 0 |

After immunisation with proteins containing variant 3 of NMB1870, sera tested against up to 5 strains which have a NMB1870 in variant 3 gave SBA titres as follows:

| | Protein | | | | | | | | |
|---|---|---|---|---|---|---|---|---|---|
| | (C) | (C) | (F) | (G) | (G) | (H) | (H) | (I) | (I) |
| | | | | | Adjuvant | | | | |
| | CFA | Alum | Alum | CFA | Alum | CFA | Alum | CFA | Alum |
| N° strains tested | 5 | 5 | 5 | 5 | 5 | 5 | 5 | 3 | 3 |
| SBA <128 | 0 | 1 | 1 | 1 | 1 | 0 | 0 | 1 | 1 |
| SBA 128-512 | 0 | 0 | 0 | 0 | 2 | 0 | 0 | 0 | 1 |
| SBA >512 | 5 | 4 | 4 | 4 | 2 | 5 | 5 | 2 | 1 |

CONCLUSIONS

At first, NMB1870 appears not to be a useful antigen for broad immunisation—its expression levels vary between strains, there is significant sequence variability, and there is no cross-protection between the different variants. However, it has been shown that even those strains which express very low levels of this antigen are susceptible to anti-NMB1870 sera. Furthermore, sequence diversity is limited to three variant forms such that broad immunity can be achieved without the need for a large number of antigens. In addition, it seems that these three proteins may offer immunity against more than just serogroup B meningococcus.

The different variants of NMB1870 can be expressed together as fusion proteins in order to give single polypeptide chains which are active against more than one variant.

NMB1870 is immunogenic during infection, is able to induce bactericidal antibodies, and protects infant rats from bacterial challenge.

Further experimental information on NMB1870 can be found in reference 197.

It will be understood that the invention is described above by way of example only and modifications may be made whilst remaining within the scope and spirit of the invention.

BRIEF DESCRIPTION OF THE SEQUENCE LISTING

| SEQ ID NO: | Description |
|---|---|
| 1-23 | 23 different NMB1870 sequences, full-length |
| 24-45 | 22 different NMB1870 sequences, with N-terminus cysteines |
| 46 | N-terminal amino acid sequence used for expression |
| 47-66 | PCR primers |
| 67-69 | Partial sequences from FIG. 1 |
| 70-73 & 86 | Sequence motifs for retention or omission from proteins of the invention |
| 74-75 | Fur boxes |
| 76 | '936' from MC58, with leader peptide processed |
| 77 | Example of a $936_{MC58}$-ΔG-$NMB1870_{M1239}$ hybrid |
| 78 | Gonococcus-derived sequence used for chimeric expression |
| 79, 82, 83, 85, 87, 88, 89, 90 | Tandem NMB1870 proteins |
| 80, 81, 84 | Truncated NMB1870 sequences |
| 91-94 | Hybrid proteins of '936' and NMB1870 |
| 95-122 | PCR primers |
| 123-141 | Full-length NMB1870 sequences |
| 142 | Triple tandem NMB1870 sequence |

-continued

| SEQ ID NO: | Description |
|---|---|
| 143 | Haji NadA sequence |
| 144 | Glycine linker |

REFERENCES

The Contents of which are Hereby Incorporated in Full by Reference

[1] Jodar et al. (2002) *Lancet* 359(9316):1499-1508.
[2] Tettelin et al. (2000) *Science* 287:1809-1815.
[3] Pizza et al. (2000) *Science* 287:1816-1820.
[4] Parkhill et al. (2000) *Nature* 404:502-506.
[5] http://dna1.chem.ou.edu/gono.html
[6] WO99/24578.
[7] WO99/36544.
[8] WO99/57280.
[9] WO00/22430.
[10] WO01/64920.
[11] WO01/64922.
[12] WO03/020756.
[13] WO03/063766.
[14] Achtman (1995) *Global epidemiology of meningococcal disease*. Pages 159-175 of *Meningococcal disease* (ed. Cartwight). ISBN: 0-471-95259-1.
[15] Caugant (1998) *APMIS* 106:505-525.
[16] Maiden et al. (1998) *Proc. Natl. Acad. Sci. USA* 95:3140-3145.
[17] Reilly & Smith (1999) *Protein Expr Purif* 17:401-409.
[18] Covacci & Rappuoli (2000) *J. Exp. Med.* 19:587-592.
[19] WO93/18150.
[20] Covacci et al. (1993) *Proc. Natl. Acad. Sci. USA* 90:5791-5795.
[21] Tummuru et al. (1994) *Infect. Immun.* 61:1799-1809.
[22] Marchetti et al. (1998) *Vaccine* 16:33-37.
[23] Telford et al. (1994) *J. Exp. Med.* 179:1653-1658.
[24] Evans et al. (1995) *Gene* 153:123-127.
[25] WO96/01272 & WO96/01273, especially SEQ ID NO:6.
[26] WO97/25429.
[27] WO98/04702.
[28] Costantino et al. (1992) *Vaccine* 10:691-698.
[29] Costantino et al. (1999) *Vaccine* 17:1251-1263.
[30] International patent application WO03/007985.
[31] Watson (2000) *Pediatr Infect Dis J* 19:331-332.
[32] Rubin (2000) *Pediatr Clin North Am* 47:269-285, v.
[33] Jedrzejas (2001) *Microbiol Mol Biol Rev* 65:187-207.

[34] Bell (2000) *Pediatr Infect Dis J* 19:1187-1188.
[35] Iwarson (1995) *APMIS* 103:321-326.
[36] Gerlich et al. (1990) *Vaccine* 8 Suppl:S63-68 & 79-80.
[37] *Vaccines* (1988) eds. Plotkin & Mortimer. ISBN 0-7216-1946-0.
[38] Del Guidice et al. (1998) *Molecular Aspects of Medicine* 19:1-70.
[39] Gustafsson et al. (1996) *N. Engl. J. Med.* 334:349-355.
[40] Rappuoli et al. (1991) *TIBTECH* 9:232-238.
[41] Hsu et al. (1999) *Clin Liver Dis* 3:901-915.
[42] WO02/079243.
[43] International patent application WO02/02606.
[44] Kalman et al. (1999) *Nature Genetics* 21:385-389.
[45] Read et al. (2000) *Nucleic Acids Res* 28:1397-406.
[46] Shirai et al. (2000) *J. Infect. Dis.* 181 (Suppl 3):S524-S527.
[47] International patent application WO99/27105.
[48] International patent application WO00/27994.
[49] International patent application WO00/37494.
[50] International patent application WO99/28475.
[51] Ross et al. (2001) *Vaccine* 19:4135-4142.
[52] Sutter et al. (2000) *Pediatr Clin North Am* 47:287-308.
[53] Zimmerman & Spann (1999) *Am Fam Physician* 59:113-118, 125-126.
[54] Dreesen (1997) *Vaccine* 15 Suppl:S2-6.
[55] *MMWR Morb Mortal Wkly Rep* 1998 Jan. 16; 47(1):12, 19.
[56] McMichael (2000) *Vaccine* 19 Suppl 1:S101-107.
[57] Schuchat (1999) *Lancet* 353(9146):51-6.
[58] International patent application WO02/34771.
[59] Dale (1999) *Infect Dis Clin North Am* 13:227-43, viii.
[60] Ferretti et al. (2001) *PNAS USA* 98: 4658-4663.
[61] Kuroda et al. (2001) *Lancet* 357(9264):1225-1240; see also pages 1218-1219.
[62] *J Toxicol Clin Toxicol* (2001) 39:85-100.
[63] Demicheli et al. (1998) *Vaccine* 16:880-884.
[64] Stepanov et al. (1996) *J Biotechnol* 44:155-160.
[65] Ingram (2001) *Trends Neurosci* 24:305-307.
[66] Rosenberg (2001) *Nature* 411:380-384.
[67] Moingeon (2001) *Vaccine* 19:1305-1326.
[68] EP-A-0372501
[69] EP-A-0378881
[70] EP-A-0427347
[71] WO93/17712
[72] WO94/03208
[73] WO98/58668
[74] EP-A-0471177
[75] WO00/56360
[76] WO91/01146
[77] WO00/61761
[78] WO01/72337
[79] *Research Disclosure,* 453077 (January 2002)
[80] Jones (2001) *Curr Opin Investig Drugs* 2:47-49.
[81] Ravenscroft et al. (1999) *Vaccine* 17:2802-2816.
[82] International patent application WO03/080678.
[83] Nilsson & Svensson (1979) *Carbohydrate Research* 69:292-296)
[84] Frash (1990) p. 123-145 of *Advances in Biotechnological Processes* vol. 13 (eds. Mizrahi & Van Wezel)
[85] Inzana (1987) *Infect. Immun.* 55:1573-1579.
[86] Kandil et al. (1997) *Glycoconj J* 14:13-17.
[87] Berkin et al. (2002) *Chemistry* 8:4424-4433.
[88] Lindberg (1999) *Vaccine* 17 Suppl 2:S28-36.
[89] Buttery & Moxon (2000) *J R Coll Physicians Lond* 34:163-168.
[90] Ahmad & Chapnick (1999) *Infect Dis Clin North Am* 13:113-33, vii.
[91] Goldblatt (1998) *J. Med. Microbiol.* 47:563-567.
[92] European patent 0477508.
[93] U.S. Pat. No. 5,306,492.
[94] WO98/42721.
[95] Dick et al. in *Conjugate Vaccines* (eds. Cruse et al.) Karger, Basel, 1989, 10:48-114.
[96] Hermanson *Bioconjugate Techniques*, Academic Press, San Diego (1996) ISBN: 0123423368.
[97] Kanra et al. (1999) *The Turkish Journal of Paediatrics* 42:421-427.
[98] Ravenscroft et al. (2000) *Dev Biol* (Basel) 103: 35-47.
[99] WO97/00697.
[100] WO02/00249.
[101] Zielen et al. (2000) *Infect. Immun.* 68:1435-1440.
[102] Darkes & Plosker (2002) *Paediatr Drugs* 4:609-630.
[103] Tettelin et al. (2001) *Science* 293:498-506.
[104] Hoskins et al (2001) *J Bacteriol* 183:5709-5717.
[105] Rappuoli (2000) *Curr Opin Microbiol* 3:445-450
[106] Rappuoli (2001) *Vaccine* 19:2688-2691.
[107] Masignani et al. (2002) *Expert Opin Biol Ther* 2:895-905.
[108] Mora et al. (2003) *Drug Discov Today* 8:459-464.
[109] Wizemann et al. (2001) *Infect Immun* 69:1593-1598.
[110] Rigden et al. (2003) *Crit. Rev Biochem Mol Biol* 38:143-168.
[111] WO02/22167.
[112] Ramsay et al. (2001) *Lancet* 357(9251):195-196.
[113] Anderson (1983) *Infect Immun* 39(1):233-238.
[114] Anderson et al. (1985) *J Clin Invest* 76(1):52-59.
[115] Falugi et al. (2001) *Eur J Immunol* 31:3816-3824.
[116] EP-A-0594610.
[117] WO02/091998.
[118] WO99/42130
[119] WO96/40242
[120] Lees et al. (1996) *Vaccine* 14:190-198.
[121] WO95/08348.
[122] U.S. Pat. No. 4,882,317
[123] U.S. Pat. No. 4,695,624
[124] Porro et al. (1985) *Mol Immunol* 22:907-919.s
[125] EP-A-0208375
[126] WO00/10599
[127] Gever et al. *Med. Microbiol. Immunol,* 165: 171-288 (1979).
[128] U.S. Pat. No. 4,057,685.
[129] U.S. Pat. Nos. 4,673,574; 4,761,283; 4,808,700.
[130] U.S. Pat. No. 4,459,286.
[131] U.S. Pat. No. 4,965,338
[132] U.S. Pat. No. 4,663,160.
[133] U.S. Pat. No. 4,761,283
[134] U.S. Pat. No. 4,356,170
[135] Lei et al. (2000) *Dev Biol* (Basel) 103:259-264.
[136] WO00/38711; U.S. Pat. No. 6,146,902.
[137] WO02/09643.
[138] Katial et al. (2002) *Infect Immun* 70:702-707.
[139] WO01/52885.
[140] European patent 0301992.
[141] Bjune et al. (1991) *Lancet* 338(8775):1093-1096.
[142] Fukasawa et al. (1999) *Vaccine* 17:2951-2958.
[143] WO02/09746.
[144] Rosenqvist et al. (1998) *Dev. Biol. Stand.* 92:323-333.
[145] WO01/09350.
[146] European patent 0449958.
[147] EP-A-0996712.
[148] EP-A-0680512.
[149] WO02/062378.

[150] WO99/59625.
[151] U.S. Pat. No. 6,180,111.
[152] WO01/34642.
[153] WO03/051379.
[154] U.S. Pat. No. 6,558,677
[155] PCT/IB03/04293.
[156] WO02/062380.
[157] WO00/25811.
[158] Peeters et al. (1996) *Vaccine* 14:1008-1015.
[159] Vermont et al. (2003) *Infect Immun* 71:1650-1655.
[160] WO01/30390.
[161] Gennaro (2000) *Remington: The Science and Practice of Pharmacy*. 20th edition, ISBN: 0683306472.
[162] WO03/009869.
[163] *Vaccine design: the subunit and adjuvant approach*, eds. Powell & Newman, Plenum Press 1995 (ISBN 0-306-44867-X).
[164] WO90/14837.
[165] WO02/26212.
[166] WO98/33487.
[167] WO00/07621.
[168] WO99/27960.
[169] WO98/57659.
[170] European patent applications 0835318, 0735898 and 0761231.
[171] Krieg (2000) *Vaccine* 19:618-622; Krieg (2001) *Curr opin Mol Ther* 2001 3:15-24; WO96/02555, WO98/16247, WO98/18810, WO98/40100, WO98/55495, WO98/37919 and WO98/52581 etc.
[172] WO99/52549.
[173] WO01/21207.
[174] WO01/21152.
[175] WO00/62800.
[176] WO00/23105.
[177] WO99/11241.
[178] de Lorenzo et al. (1987) *J. Bacteriol.* 169:2624-2630.
[179] Nakai & Kanehisa (1991) *Proteins* 11:95-110.
[180] Yamaguchi et al. (1988) *Cell* 53:423-432.
[181] http://cubic.bioc.columbia.edu/predictprotein/
[182] http://www.ncbi.nlm.nih.gov/blast
[183] Strutzberg et al. (1995) *Infect. Immun.* 63:3846-3850.
[184] Legrain et al. (1993) *Gene* 130:73-80.
[185] Loosmore et al. (1996) *Mol Microbiol* 19:575-586.
[186] Myers et al. (1998) *Infect. Immun.* 66:4183-4192.
[187] Schlegel et al. (2992) *J. Bacteriol.* 184:3069-3077.
[188] Turner et al. (2002) *Infect. Immun.* 70:4447-4461.
[189] http://www.ncbi.nlm.nih.gov/PMGifs/Genomes/micr.html
[190] Voulhoux et al. Thirteeth International Pathogenic *Neisseria* Conference. NIPH, Oslo, page 31.
[191] Comanducci et al. (2002) *J. Exp. Med.* 195: 1445-1454.
[192] WO 03/010194.
[193] Jennings et al. (2002) *Eur. J. Biochem.* 269:3722-3731.
[194] Granoff et al. (1998) *J. Immunol.* 160:5028-5036.
[195] Grifantini et al. (2002) *Nat. Biotechnol.* 20:914-921.
[196] Peeters et al. (1999) *Vaccine* 17:2702-2712.
[197] Masignani et al. (2003) *J Exp Med* 197:789-799.

What is claimed is:

1. A composition comprising an aluminum salt adjuvant, a histidine buffer, and at least two of the following isolated antigens:
   (a) a first isolated protein, comprising an amino acid sequence having at least 85% sequence identity to SEQ ID NO: 24;
   (b) a second isolated protein, comprising an amino acid sequence having at least 85% sequence identity to SEQ ID NO: 33; and
   (c) a third isolated protein, comprising an amino acid sequence having at least 85% identity to SEQ ID NO: 41, wherein: isolated protein (a) has less than 70% sequence identity to isolated protein (b); isolated protein (a) has less than 70% sequence identity to isolated protein (c); and isolated protein (b) has less than 70% sequence identity to isolated protein (c).

2. The composition of claim 1, wherein one or more of the proteins is a lipoprotein.

3. The composition of claim 1, wherein at least one of the proteins does not include the amino acid sequence TRSKP (SEQ ID NO: 70) or TRSKPV (SEQ ID NO: 71) within 10 amino acids of its N-terminus.

4. The composition of claim 1, wherein at least one of the proteins does not include the amino acid sequence PSEPPFG (SEQ ID NO: 72) within 10 amino acids of its N-terminus.

5. The composition of claim 1, wherein at least one of the proteins includes the amino acid sequence GGGG (SEQ ID NO: 73).

6. The composition of claim 1, wherein at least one of the proteins is used in the form of a fusion protein.

7. The composition of claim 6, wherein the fusion protein includes SEQ ID NO: 46 or the *Haemophilus influenzae* P4 lipoprotein leader sequence.

8. The composition of claim 1, comprising a Neisserial antigen other than a NMB1870 protein.

9. The composition of claim 1, comprising a vesicle prepared from *Neisseria meningitidis*.

10. The composition of claim 1, comprising a saccharide antigen from *Neisseria meningitidis* serogroup A, C, W135 or Y.

11. The composition of claim 10, comprising a saccharide antigen from *Neisseria meningitidis* serogroups A, C, W135 and Y.

12. The composition of claim 1, comprising a saccharide antigen from *Haemophilus influenzae* type B.

13. The composition of claim 10, wherein the saccharide antigen is conjugated to a carrier protein.

14. The composition of claim 10, wherein the saccharide antigen is an oligosaccharide.

15. The composition of claim 1, further comprising an antigen from *Streptococcus pneumoniae*.

16. The composition of claim 11, wherein the serogroup A saccharide antigen is a modified saccharide in which one or more of the hydroxyl groups on the native saccharide has/have been replaced by a blocking group.

17. The composition of claim 11, wherein the serogroup A saccharide antigen contains n monosaccharide units, wherein at least 50% of the monosaccharide units do not have —OH groups at both of positions 3 and 4.

18. The composition of claim 13, wherein the carrier protein is a diphtheria toxoid, a tetanus toxoid, CRM197, a *Neisseria meningitidis* outer membrane protein, protein D from *Haemophilus influenzae*, or pneumococcal surface protein PspA.

19. A composition comprising an aluminum salt adjuvant, a histidine buffer, and at least two of the following isolated antigens:
(a) a first isolated protein comprising an amino acid sequence consisting of a fragment of at least 20 contiguous amino acids from SEQ ID NO: 24;
(b) a second isolated protein comprising an amino acid sequence consisting of a fragment of at least 20 contiguous amino acids from SEQ ID NO: 33; and
(c) a third isolated protein comprising an amino acid sequence consisting of a fragment of at least 20 contiguous amino acids from SEQ ID NO: 41, wherein: isolated protein (a) has less than 70% sequence identity across its full length to isolated protein (b); isolated protein (a) has less than 70% sequence identity across its full length to isolated protein (c); and isolated protein (b) has less than 70% sequence identity across its full length to isolated protein (c).

20. The composition of claim 19, wherein one or more of the proteins is a lipoprotein.

21. The composition of claim 19, wherein at least one of the proteins does not include the amino acid sequence TRSKP (SEQ ID NO: 70) or TRSKPV (SEQ ID NO: 71) within 10 amino acids of its N-terminus.

22. The composition of claim 19, wherein at least one of the proteins does not include the amino acid sequence PSEPPFG (SEQ ID NO: 72) within 10 amino acids of its N-terminus.

23. The composition of claim 19, wherein at least one of the proteins includes the amino acid sequence GGGG (SEQ ID NO: 73).

24. The composition of claim 19, wherein at least one of the proteins is used in the form of a fusion protein.

25. The composition of claim 24, wherein the fusion protein includes SEQ ID NO: 46 or the *Haemophilus influenzae* P4 lipoprotein leader sequence.

26. A composition comprising an aluminum hydroxyphosphate adjuvant and at least two of the following isolated antigens:
(a) a first isolated protein, comprising an amino acid sequence having at least 85% sequence identity to SEQ ID NO: 24;
(b) a second isolated protein, comprising an amino acid sequence having at least 85% sequence identity to SEQ ID NO: 33; and
(c) a third isolated protein, comprising an amino acid sequence having at least 85% identity to SEQ ID NO: 41, wherein: isolated protein (a) has less than 70% sequence identity to isolated protein (b); isolated protein (a) has less than 70% sequence identity to isolated protein (c); and isolated protein (b) has less than 70% sequence identity to isolated protein (c).

27. The composition of claim 26, wherein one or more of the proteins is a lipoprotein.

28. The composition of claim 26, wherein at least one of the proteins does not include the amino acid sequence TRSKP (SEQ ID NO: 70) or TRSKPV (SEQ ID NO: 71) within 10 amino acids of its N-terminus.

29. The composition of claim 26, wherein at least one of the proteins does not include the amino acid sequence PSEPPFG (SEQ ID NO: 72) within 10 amino acids of its N-terminus.

30. The composition of claim 26, wherein at least one of the proteins includes the amino acid sequence GGGG (SEQ ID NO: 73).

31. The composition of claim 26, wherein at least one of the proteins is used in the form of a fusion protein.

32. The composition of claim 31, wherein the fusion protein includes SEQ ID NO: 46 or the *Haemophilus influenzae* P4 lipoprotein leader sequence.

33. The composition of claim 26, wherein the composition further comprises a histidine buffer.

34. A composition comprising an aluminum salt adjuvant and at least two of the following isolated antigens:
(a) a first isolated protein, comprising an amino acid sequence having at least 85% sequence identity to SEQ ID NO: 24;
(b) a second isolated protein, comprising an amino acid sequence having at least 85% sequence identity to SEQ ID NO: 33; and
(c) a third isolated protein, comprising an amino acid sequence having at least 85% identity to SEQ ID NO: 41, wherein: isolated protein (a) has less than 70% sequence identity to isolated protein (b); isolated protein (a) has less than 70% sequence identity to isolated protein (c); and isolated protein (b) has less than 70% sequence identity to isolated protein (c), wherein at least one the at least two isolated antigens is adsorbed to the aluminum salt adjuvant.

35. The composition of claim 34, wherein one or more of the proteins is a lipoprotein.

36. The composition of claim 34, wherein at least one of the proteins does not include the amino acid sequence TRSKP (SEQ ID NO: 70) or TRSKPV (SEQ ID NO: 71) within 10 amino acids of its N-terminus.

37. The composition of claim 34, wherein at least one of the proteins does not include the amino acid sequence PSEPPFG (SEQ ID NO: 72) within 10 amino acids of its N-terminus.

38. The composition of claim 34, wherein at least one of the proteins includes the amino acid sequence GGGG (SEQ ID NO: 73).

39. The composition of claim 34, wherein at least one of the proteins is used in the form of a fusion protein.

40. The composition of claim 39, wherein the fusion protein includes SEQ ID NO: 46 or the *Haemophilus influenzae* P4 lipoprotein leader sequence.

41. The composition of claim 34, wherein the composition further comprises a histidine buffer.

* * * * *